(12) United States Patent
Moll et al.

(10) Patent No.: US 9,358,076 B2
(45) Date of Patent: Jun. 7, 2016

(54) SYSTEM AND METHOD FOR ENDOLUMINAL AND TRANSLUMENAL THERAPY

(71) Applicant: Hansen Medical, Inc., Mountain View, CA (US)

(72) Inventors: Frederic H. Moll, San Francisco, CA (US); Randall L. Schlesinger, San Mateo, CA (US); Farzad Soleimani, Houston, TX (US); Daniel T. Wallace, Santa Cruz, CA (US)

(73) Assignee: HANSEN MEDICAL, INC., Mountain View, CA (US)

( * ) Notice: Subject to any disclaimer, the term of this patent is extended or adjusted under 35 U.S.C. 154(b) by 0 days.

(21) Appl. No.: 14/685,089

(22) Filed: Apr. 13, 2015

(65) Prior Publication Data
US 2015/0209112 A1 Jul. 30, 2015

Related U.S. Application Data

(63) Continuation of application No. 13/355,321, filed on Jan. 20, 2012, now abandoned.

(60) Provisional application No. 61/434,797, filed on Jan. 20, 2011.

(51) Int. Cl.
*A61B 18/14* (2006.01)
*A61B 19/00* (2006.01)
(Continued)

(52) U.S. Cl.
CPC ........... *A61B 19/2203* (2013.01); *A61B 5/0066* (2013.01); *A61B 5/0084* (2013.01);
(Continued)

(58) Field of Classification Search
CPC ........... A61B 19/5244; A61B 18/1492; A61B 2018/00839; A61B 19/2203; A61B 2018/00267; A61B 2018/00285; A61B 2018/00577; A61B 2019/2211; A61B 1/307; A61B 2018/00404; A61B 2018/00511; A61B 2018/00517; A61B 2018/0212; A61B 2018/1861; A61B 2019/2219; A61B 2019/505; A61B 2019/5289; A61B 18/24; A61B 19/50; A61B 2017/00053; A61B 2017/00292; A61B 2017/003; A61B 2018/00434; A61B 5/0084; A61B 5/201; A61B 2018/0022; A61B 19/56; A61B 2017/00743; A61B 5/6853; A61B 5/6858; A61B 19/5212; A61B 2019/507; A61B 2019/5278; A61B 8/12; A61N 1/05; A61M 25/0147; A61M 2025/0681; A61M 25/0133; A61M 25/04; A61M 25/10; A61M 25/0105; G01R 33/285

See application file for complete search history.

(56) References Cited

U.S. PATENT DOCUMENTS 3,807,390 A 4/1974 Ostrowski et al.
4,443,698 A 4/1984 Schiffner
(Continued)

FOREIGN PATENT DOCUMENTS

CA 2285342 A1 10/1998
EP 1103223 A2 5/2001
(Continued)

OTHER PUBLICATIONS

Papers from file history for U.S. Appl. No. 12/507,727 (15 pages).
(Continued)

*Primary Examiner* — Deborah Malamud
(74) *Attorney, Agent, or Firm* — Dorsey & Whitney LLP; Scott M. Smith

(57) ABSTRACT

A system for conducting denervation of the neural plexus adjacent the renal artery, comprises a pre-shaped ablative element operatively coupled to an elongate deployment member configured to be navigated into the renal artery, the pre-shaped ablative element comprising one or more RF electrodes disposed in an arcuate pattern; and an energy source operatively coupled to the one or more RF electrodes and being configured to cause current to flow from the pre-shaped ablative element and cause localized heating sufficient to denervate nearby neural tissue.

10 Claims, 51 Drawing Sheets

(51) Int. Cl.

| | | |
|---|---|---|
| *A61B 5/00* | (2006.01) | |
| *A61B 5/02* | (2006.01) | |
| *A61B 5/20* | (2006.01) | |
| A61B 1/307 | (2006.01) | |
| A61B 5/06 | (2006.01) | |
| A61B 5/145 | (2006.01) | |
| A61B 18/24 | (2006.01) | |
| A61B 17/00 | (2006.01) | |
| A61B 18/00 | (2006.01) | |
| A61B 18/02 | (2006.01) | |
| A61B 18/18 | (2006.01) | |

(52) U.S. Cl.
CPC .............. *A61B5/02007* (2013.01); *A61B 5/201* (2013.01); *A61B 18/1492* (2013.01); *A61B 19/50* (2013.01); A61B 1/307 (2013.01); A61B 5/062 (2013.01); A61B 5/065 (2013.01); A61B 5/14546 (2013.01); A61B 18/24 (2013.01); A61B 2017/00053 (2013.01); A61B 2017/00256 (2013.01); A61B 2017/00292 (2013.01); A61B 2018/00267 (2013.01); A61B 2018/00285 (2013.01); A61B 2018/00404 (2013.01); A61B 2018/00434 (2013.01); A61B 2018/00511 (2013.01); A61B 2018/00517 (2013.01); A61B 2018/00577 (2013.01); A61B 2018/00839 (2013.01); A61B 2018/0212 (2013.01); A61B 2018/1405 (2013.01); A61B 2018/1475 (2013.01); A61B 2018/1861 (2013.01); A61B 2019/2211 (2013.01); A61B 2019/505 (2013.01)

(56) References Cited

U.S. PATENT DOCUMENTS

| | | |
|---|---|---|
| 4,761,073 A | 8/1988 | Meltz et al. |
| 4,945,305 A | 7/1990 | Blood |
| 4,960,410 A | 10/1990 | Pinchuk |
| 4,996,419 A | 2/1991 | Morey |
| 5,003,982 A | 4/1991 | Halperin |
| 5,007,705 A | 4/1991 | Morey et al. |
| 5,066,133 A | 11/1991 | Brienza |
| 5,067,346 A | 11/1991 | Field |
| 5,078,714 A | 1/1992 | Katims |
| 5,086,401 A | 2/1992 | Glassman et al. |
| 5,118,931 A | 6/1992 | Udd et al. |
| 5,144,960 A | 9/1992 | Mehra et al. |
| 5,267,339 A | 11/1993 | Yamauchi et al. |
| 5,339,799 A | 8/1994 | Kami et al. |
| 5,341,807 A | 8/1994 | Nardella |
| 5,368,015 A | 11/1994 | Wilk |
| 5,380,995 A | 1/1995 | Udd et al. |
| 5,382,885 A | 1/1995 | Salcudean et al. |
| 5,394,875 A | 3/1995 | Lewis et al. |
| 5,397,443 A | 3/1995 | Michaels |
| 5,397,891 A | 3/1995 | Udd et al. |
| 5,398,691 A | 3/1995 | Martin et al. |
| 5,401,956 A | 3/1995 | Dunphy et al. |
| 5,408,409 A | 4/1995 | Glassman et al. |
| 5,433,215 A | 7/1995 | Athanasiou et al. |
| 5,447,529 A | 9/1995 | Marchlinski et al. |
| 5,469,857 A | 11/1995 | Laurent et al. |
| 5,477,856 A | 12/1995 | Lundquist |
| 5,492,131 A | 2/1996 | Galel |
| 5,563,967 A | 10/1996 | Haake |
| 5,591,965 A | 1/1997 | Udd |
| 5,600,330 A | 2/1997 | Blood |
| 5,627,927 A | 5/1997 | Udd |
| 5,630,783 A | 5/1997 | Steinberg |
| 5,631,973 A | 5/1997 | Green |
| 5,662,108 A | 9/1997 | Budd et al. |
| 5,673,704 A | 10/1997 | Marchlinski et al. |
| 5,697,377 A | 12/1997 | Wittkampf |
| 5,713,946 A | 2/1998 | Ben-Haim |
| 5,722,959 A | 3/1998 | Bierman |
| 5,738,096 A | 4/1998 | Ben-Haim |
| 5,749,362 A | 5/1998 | Funda et al. |
| 5,754,741 A | 5/1998 | Wang et al. |
| 5,762,458 A | 6/1998 | Wang et al. |
| 5,784,542 A | 7/1998 | Ohm et al. |
| 5,798,521 A | 8/1998 | Froggatt |
| 5,799,055 A | 8/1998 | Peshkin et al. |
| 5,810,716 A | 9/1998 | Mukherjee et al. |
| 5,815,640 A | 9/1998 | Wang et al. |
| 5,825,982 A | 10/1998 | Wright et al. |
| 5,828,059 A | 10/1998 | Udd |
| 5,833,608 A | 11/1998 | Acker |
| 5,836,869 A | 11/1998 | Kudo et al. |
| 5,836,874 A | 11/1998 | Swanson et al. |
| 5,836,990 A | 11/1998 | Li |
| 5,843,076 A | 12/1998 | Webster, Jr. et al. |
| 5,845,646 A | 12/1998 | Lemelson |
| 5,876,325 A | 3/1999 | Mizuno et al. |
| 5,878,193 A | 3/1999 | Wang et al. |
| 5,891,095 A | 4/1999 | Eggers et al. |
| 5,911,694 A | 6/1999 | Ikeda et al. |
| 5,917,978 A | 6/1999 | Rutterman |
| 5,921,924 A | 7/1999 | Avitall |
| 5,935,079 A | 8/1999 | Swanson et al. |
| 5,950,629 A | 9/1999 | Taylor et al. |
| 5,953,683 A | 9/1999 | Hansen et al. |
| 5,983,126 A | 11/1999 | Wittkampf |
| 6,004,271 A | 12/1999 | Moore |
| 6,035,082 A | 3/2000 | Murphy et al. |
| 6,061,587 A | 5/2000 | Kucharczyk et al. |
| 6,063,022 A | 5/2000 | Ben-Haim |
| 6,063,082 A | 5/2000 | Devore et al. |
| 6,063,095 A | 5/2000 | Wang et al. |
| 6,068,604 A | 5/2000 | Krause et al. |
| 6,069,420 A | 5/2000 | Mizzi et al. |
| 6,080,181 A | 6/2000 | Jensen et al. |
| 6,083,170 A | 7/2000 | Ben-Haim |
| 6,096,004 A | 8/2000 | Meglan et al. |
| 6,102,850 A | 8/2000 | Wang et al. |
| 6,106,511 A | 8/2000 | Jensen |
| 6,129,668 A | 10/2000 | Haynor et al. |
| 6,132,368 A | 10/2000 | Cooper |
| 6,144,026 A | 11/2000 | Udd et al. |
| 6,161,032 A | 12/2000 | Acker |
| 6,172,499 B1 | 1/2001 | Ashe |
| 6,201,984 B1 | 3/2001 | Funda et al. |
| 6,203,493 B1 | 3/2001 | Ben-Haim |
| 6,215,943 B1 | 4/2001 | Crotts et al. |
| 6,226,543 B1 | 5/2001 | Gilboa et al. |
| 6,228,028 B1 | 5/2001 | Klein et al. |
| 6,233,476 B1 | 5/2001 | Strommer et al. |
| 6,233,491 B1 | 5/2001 | Kordis et al. |
| 6,233,504 B1 | 5/2001 | Das et al. |
| 6,246,200 B1 | 6/2001 | Blumenkranz et al. |
| 6,256,090 B1 | 7/2001 | Chen et al. |
| 6,266,551 B1 | 7/2001 | Osadchy et al. |
| 6,272,371 B1 | 8/2001 | Shlomo |
| 6,275,511 B1 | 8/2001 | Pan et al. |
| 6,275,628 B1 | 8/2001 | Jones et al. |
| 6,301,420 B1 | 10/2001 | Greenaway et al. |
| 6,301,496 B1 | 10/2001 | Reisfeld |
| 6,309,397 B1 | 10/2001 | Julian et al. |
| 6,310,828 B1 | 10/2001 | Mumm et al. |
| 6,312,435 B1 | 11/2001 | Wallace et al. |
| 6,331,181 B1 | 12/2001 | Tierney et al. |
| 6,364,888 B1 | 4/2002 | Niemeyer et al. |
| 6,366,722 B1 | 4/2002 | Murphy et al. |
| 6,370,411 B1 | 4/2002 | Osadchy et al. |
| 6,371,952 B1 | 4/2002 | Madhani et al. |
| 6,375,471 B1 | 4/2002 | Wendlandt et al. |
| 6,380,732 B1 | 4/2002 | Gilboa |
| 6,384,483 B1 | 5/2002 | Igarashi et al. |
| 6,389,187 B1 | 5/2002 | Greenaway et al. |
| 6,393,340 B2 | 5/2002 | Funda et al. |
| 6,398,731 B1 | 6/2002 | Mumm et al. |
| 6,400,979 B1 | 6/2002 | Stoianovici et al. |

(56) References Cited

U.S. PATENT DOCUMENTS

| | | |
|---|---|---|
| 6,404,956 B1 | 6/2002 | Brennan, III et al. |
| 6,415,171 B1 | 7/2002 | Gueziec et al. |
| 6,424,885 B1 | 7/2002 | Niemeyer et al. |
| 6,426,796 B1 | 7/2002 | Pulliam et al. |
| 6,470,205 B2 | 10/2002 | Bosselmann et al. |
| 6,471,710 B1 | 10/2002 | Bucholtz |
| 6,491,701 B2 | 12/2002 | Tierney et al. |
| 6,493,573 B1 | 12/2002 | Martinelli et al. |
| 6,493,608 B1 | 12/2002 | Niemeyer |
| 6,530,913 B1 | 3/2003 | Giba et al. |
| 6,544,230 B1 | 4/2003 | Flaherty et al. |
| 6,545,760 B1 | 4/2003 | Froggatt et al. |
| 6,550,342 B2 | 4/2003 | Croteau et al. |
| 6,551,273 B1 | 4/2003 | Olson et al. |
| 6,563,107 B2 | 5/2003 | Danisch et al. |
| 6,565,554 B1 | 5/2003 | Niemeyer |
| 6,571,639 B1 | 6/2003 | May et al. |
| 6,574,355 B2 | 6/2003 | Green |
| 6,580,938 B1 | 6/2003 | Acker |
| 6,587,750 B2 | 7/2003 | Gerbi et al. |
| 6,594,552 B1 | 7/2003 | Nowlin et al. |
| 6,610,007 B2 | 8/2003 | Belson et al. |
| 6,611,700 B1 | 8/2003 | Vilsmeier et al. |
| 6,615,155 B2 | 9/2003 | Gilboa |
| 6,618,612 B1 | 9/2003 | Acker et al. |
| 6,620,173 B2 | 9/2003 | Gerbi et al. |
| 6,626,899 B2 | 9/2003 | Houser et al. |
| 6,626,902 B1 | 9/2003 | Kucharczyk et al. |
| 6,659,939 B2 | 12/2003 | Moll et al. |
| 6,669,709 B1 | 12/2003 | Cohn et al. |
| 6,671,055 B1 | 12/2003 | Wavering et al. |
| 6,685,698 B2 | 2/2004 | Morley et al. |
| 6,697,664 B2 | 2/2004 | Kienzle, III et al. |
| 6,699,235 B2 | 3/2004 | Wallace et al. |
| 6,716,166 B2 | 4/2004 | Govari |
| 6,716,178 B1 | 4/2004 | Lee et al. |
| 6,726,675 B1 | 4/2004 | Beyar |
| 6,726,699 B1 | 4/2004 | Wright et al. |
| 6,741,883 B2 | 5/2004 | Gildenberg |
| 6,774,624 B2 | 8/2004 | Anderson et al. |
| 6,783,524 B2 | 8/2004 | Anderson et al. |
| 6,796,963 B2 | 9/2004 | Carpenter et al. |
| 6,799,065 B1 | 9/2004 | Niemeyer |
| 6,817,973 B2 | 11/2004 | Merril et al. |
| 6,817,974 B2 | 11/2004 | Cooper et al. |
| 6,817,981 B2 | 11/2004 | Luce |
| 6,826,343 B2 | 11/2004 | Davis et al. |
| 6,850,817 B1 | 2/2005 | Green |
| 6,852,107 B2 | 2/2005 | Wang et al. |
| 6,858,003 B2 | 2/2005 | Evans et al. |
| 6,868,195 B2 | 3/2005 | Fujita |
| 6,876,786 B2 | 4/2005 | Chliaguine et al. |
| 6,888,623 B2 | 5/2005 | Clements |
| 6,892,090 B2 | 5/2005 | Verard et al. |
| 6,898,337 B2 | 5/2005 | Averett et al. |
| 6,905,460 B2 | 6/2005 | Wang et al. |
| 6,923,048 B2 | 8/2005 | Willsch et al. |
| 6,950,570 B1 | 9/2005 | Novotny |
| 6,963,792 B1 | 11/2005 | Green |
| 6,965,708 B2 | 11/2005 | Luo et al. |
| 6,974,455 B2 | 12/2005 | Garabedian et al. |
| 6,987,897 B2 | 1/2006 | Elster et al. |
| 7,010,182 B2 | 3/2006 | Pennington |
| 7,021,173 B2 | 4/2006 | Stoianovici et al. |
| 7,038,190 B2 | 5/2006 | Udd et al. |
| 7,042,573 B2 | 5/2006 | Froggatt |
| 7,046,866 B2 | 5/2006 | Sahlgren et al. |
| 7,074,179 B2 | 7/2006 | Wang et al. |
| 7,087,049 B2 | 8/2006 | Nowlin et al. |
| 7,154,081 B1 | 12/2006 | Friedersdorf et al. |
| 7,169,141 B2 | 1/2007 | Brock et al. |
| 7,225,012 B1 | 5/2007 | Susil et al. |
| 7,280,863 B2 | 10/2007 | Shachar |
| 7,297,142 B2 | 11/2007 | Brock |
| 7,320,700 B2 | 1/2008 | Cooper et al. |
| 7,330,245 B2 | 2/2008 | Froggatt |
| 7,331,967 B2 | 2/2008 | Lee et al. |
| 7,343,195 B2 | 3/2008 | Strommer et al. |
| 7,371,210 B2 | 5/2008 | Brock et al. |
| 7,404,824 B1 | 7/2008 | Webler et al. |
| 7,494,494 B2 | 2/2009 | Stoianovici et al. |
| 7,538,883 B2 | 5/2009 | Froggatt |
| 7,540,866 B2 | 6/2009 | Viswanathan et al. |
| 7,561,276 B2 | 7/2009 | Boyd |
| 7,742,805 B2 | 6/2010 | Furnish et al. |
| 7,772,541 B2 | 8/2010 | Froggatt et al. |
| 7,781,724 B2 | 8/2010 | Childers et al. |
| 7,789,875 B2 | 9/2010 | Brock et al. |
| 7,850,642 B2 | 12/2010 | Moll et al. |
| 7,972,298 B2 | 7/2011 | Wallace et al. |
| 8,050,523 B2 | 11/2011 | Younge et al. |
| 8,052,636 B2 | 11/2011 | Moll et al. |
| 8,092,397 B2 | 1/2012 | Wallace et al. |
| 8,190,238 B2 | 5/2012 | Moll et al. |
| 8,219,178 B2 | 7/2012 | Smith et al. |
| 8,498,691 B2 | 7/2013 | Moll et al. |
| 8,780,339 B2 | 7/2014 | Udd |
| 2001/0009976 A1 | 7/2001 | Panescu et al. |
| 2001/0021843 A1 | 9/2001 | Bosselmann et al. |
| 2001/0029366 A1 | 10/2001 | Swanson et al. |
| 2002/0064330 A1 | 5/2002 | Croteau et al. |
| 2002/0087169 A1 | 7/2002 | Brock et al. |
| 2002/0138009 A1 | 9/2002 | Brockway et al. |
| 2002/0156369 A1 | 10/2002 | Chakeres |
| 2002/0177789 A1 | 11/2002 | Ferry et al. |
| 2003/0016898 A1 | 1/2003 | Baruch et al. |
| 2003/0050649 A1 | 3/2003 | Brock et al. |
| 2003/0055360 A1 | 3/2003 | Zeleznik et al. |
| 2003/0073908 A1 | 4/2003 | Desai |
| 2003/0074011 A1 | 4/2003 | Gilboa et al. |
| 2003/0109780 A1 | 6/2003 | Coste-Maniere et al. |
| 2003/0135204 A1 | 7/2003 | Lee et al. |
| 2003/0158545 A1 | 8/2003 | Hovda et al. |
| 2003/0188585 A1 | 10/2003 | Esser et al. |
| 2003/0195502 A1 | 10/2003 | Garabedian et al. |
| 2004/0034282 A1 | 2/2004 | Quaid, III |
| 2004/0034300 A1 | 2/2004 | Verard et al. |
| 2004/0034365 A1 | 2/2004 | Lentz et al. |
| 2004/0152972 A1 | 8/2004 | Hunter |
| 2004/0165810 A1 | 8/2004 | Fujita |
| 2004/0171929 A1 | 9/2004 | Leitner et al. |
| 2004/0176751 A1 | 9/2004 | Weitzner et al. |
| 2004/0193146 A1 | 9/2004 | Lee et al. |
| 2004/0208413 A1 | 10/2004 | Scandale et al. |
| 2004/0220588 A1 | 11/2004 | Kermode et al. |
| 2005/0027397 A1 | 2/2005 | Niemeyer |
| 2005/0036140 A1 | 2/2005 | Elster et al. |
| 2005/0054934 A1 | 3/2005 | Furnish et al. |
| 2005/0059960 A1 | 3/2005 | Simaan et al. |
| 2005/0085728 A1 | 4/2005 | Fukuda |
| 2005/0131460 A1 | 6/2005 | Gifford, III et al. |
| 2005/0159789 A1 | 7/2005 | Brockway et al. |
| 2005/0165276 A1 | 7/2005 | Belson et al. |
| 2005/0182295 A1 | 8/2005 | Soper et al. |
| 2005/0182330 A1 | 8/2005 | Brockway et al. |
| 2005/0200324 A1 | 9/2005 | Guthart et al. |
| 2005/0201664 A1 | 9/2005 | Udd et al. |
| 2005/0203382 A1 | 9/2005 | Govari et al. |
| 2005/0222554 A1 | 10/2005 | Wallace et al. |
| 2005/0254575 A1 | 11/2005 | Hannuksela et al. |
| 2006/0013523 A1 | 1/2006 | Childers et al. |
| 2006/0025679 A1 | 2/2006 | Viswanathan et al. |
| 2006/0036164 A1 | 2/2006 | Wilson et al. |
| 2006/0036213 A1 | 2/2006 | Viswanathan et al. |
| 2006/0058647 A1 | 3/2006 | Strommer et al. |
| 2006/0100610 A1 | 5/2006 | Wallace et al. |
| 2006/0142897 A1 | 6/2006 | Green |
| 2006/0161045 A1 | 7/2006 | Merril et al. |
| 2006/0178556 A1 | 8/2006 | Hasser et al. |
| 2006/0200049 A1 | 9/2006 | Leo et al. |
| 2006/0271036 A1 | 11/2006 | Garabedian et al. |
| 2006/0276827 A1 | 12/2006 | Mitelberg et al. |
| 2006/0293864 A1 | 12/2006 | Soss |
| 2007/0038181 A1 | 2/2007 | Melamud et al. |

(56) References Cited

U.S. PATENT DOCUMENTS

| | | |
|---|---|---|
| 2007/0043338 A1 | 2/2007 | Moll et al. |
| 2007/0060847 A1 | 3/2007 | Leo et al. |
| 2007/0060879 A1 | 3/2007 | Weitzner et al. |
| 2007/0065077 A1 | 3/2007 | Childers et al. |
| 2007/0123851 A1 | 5/2007 | Alejandro et al. |
| 2007/0156019 A1 | 7/2007 | Larkin et al. |
| 2007/0197896 A1 | 8/2007 | Moll et al. |
| 2007/0197939 A1 | 8/2007 | Wallace et al. |
| 2007/0201793 A1 | 8/2007 | Askins et al. |
| 2007/0233044 A1 | 10/2007 | Wallace et al. |
| 2007/0249901 A1 | 10/2007 | Ohline et al. |
| 2007/0265503 A1 | 11/2007 | Schlesinger et al. |
| 2007/0287999 A1 | 12/2007 | Malecki et al. |
| 2007/0293724 A1 | 12/2007 | Saadat et al. |
| 2007/0299434 A1 | 12/2007 | Malecki et al. |
| 2008/0009750 A1 | 1/2008 | Aeby et al. |
| 2008/0015445 A1 | 1/2008 | Saadat et al. |
| 2008/0058836 A1 | 3/2008 | Moll et al. |
| 2008/0183071 A1 | 7/2008 | Strommer et al. |
| 2008/0212082 A1 | 9/2008 | Froggatt et al. |
| 2008/0218770 A1 | 9/2008 | Moll et al. |
| 2008/0285909 A1 | 11/2008 | Younge et al. |
| 2008/0300592 A1 | 12/2008 | Weitzner et al. |
| 2008/0319311 A1 | 12/2008 | Hamadeh |
| 2009/0024195 A1 | 1/2009 | Rezai et al. |
| 2009/0054884 A1 | 2/2009 | Farley et al. |
| 2009/0082660 A1 | 3/2009 | Rahn et al. |
| 2009/0123111 A1 | 5/2009 | Udd |
| 2009/0137952 A1 | 5/2009 | Ramamurthy et al. |
| 2009/0201503 A1 | 8/2009 | Bennion et al. |
| 2009/0221908 A1 | 9/2009 | Glossop |
| 2009/0227997 A1 | 9/2009 | Wang et al. |
| 2009/0312756 A1 | 12/2009 | Schlesinger et al. |
| 2009/0318797 A1 | 12/2009 | Hadani |
| 2009/0320527 A1 | 12/2009 | Harper et al. |
| 2009/0324161 A1 | 12/2009 | Prisco |
| 2010/0081920 A1 | 4/2010 | Whitmore, III et al. |
| 2010/0106140 A1 | 4/2010 | Odland et al. |
| 2010/0114115 A1 | 5/2010 | Schlesinger et al. |
| 2010/0179632 A1 | 7/2010 | Bruszewski et al. |
| 2010/0312096 A1 | 12/2010 | Guttman et al. |
| 2011/0090486 A1 | 4/2011 | Udd |
| 2011/0172680 A1 | 7/2011 | Younge et al. |
| 2011/0200171 A1 | 8/2011 | Beetel et al. |
| 2011/0295267 A1 | 12/2011 | Tanner et al. |
| 2011/0301662 A1 | 12/2011 | Bar-Yoseph et al. |
| 2011/0319815 A1 | 12/2011 | Roelle et al. |
| 2012/0089047 A1 | 4/2012 | Ryba et al. |
| 2012/0191079 A1 | 7/2012 | Moll et al. |
| 2012/0191083 A1 | 7/2012 | Moll et al. |
| 2012/0191086 A1 | 7/2012 | Moll et al. |
| 2012/0191107 A1 | 7/2012 | Tanner et al. |
| 2012/0281205 A1 | 11/2012 | Askins |
| 2013/0028554 A1 | 1/2013 | Wong et al. |
| 2013/0030363 A1 | 1/2013 | Wong et al. |

FOREIGN PATENT DOCUMENTS

| | | |
|---|---|---|
| WO | 9202276 A1 | 2/1992 |
| WO | 9744089 A1 | 11/1997 |
| WO | 9945994 A1 | 9/1999 |
| WO | 0011495 A1 | 3/2000 |
| WO | 0045193 A1 | 8/2000 |
| WO | 0133165 A1 | 5/2001 |
| WO | 0219898 A2 | 3/2002 |
| WO | 0247751 A2 | 6/2002 |
| WO | 03065095 A2 | 8/2003 |
| WO | 03077769 A1 | 9/2003 |
| WO | 03091839 A2 | 11/2003 |
| WO | 2004001469 A1 | 12/2003 |
| WO | 2005055605 A1 | 6/2005 |
| WO | 2005087128 A1 | 9/2005 |
| WO | 2006092707 A1 | 9/2006 |
| WO | 2006099056 A2 | 9/2006 |
| WO | 2007015139 A2 | 2/2007 |
| WO | 2007045028 A1 | 4/2007 |
| WO | 2007109778 A1 | 9/2007 |
| WO | 2008094949 A2 | 8/2008 |
| WO | 2008131303 A2 | 10/2008 |
| WO | 2009094588 A2 | 7/2009 |
| WO | 2012100211 A2 | 7/2012 |
| WO | 2014/028699 A1 | 2/2014 |
| WO | 2014/028702 A1 | 2/2014 |

OTHER PUBLICATIONS

Papers from file history for U.S. Appl. No. 12/106,254 (57 pages).
Papers from file history for U.S. Appl. No. 11/690,116 (45 pages).
Papers from file history for Chinese Patent Application No. 200780009956.6 (20 pages).
Amendment and Response to Non-Final Office Action for related U.S. Appl. No. 11/678,016 filed Dec. 27, 2010 (21 pages).
"Distributed Sensing System Sensor Array Specification," www.lunainnovations.com, pp. 1-3, online publication.
"Fiber Optic Interferometer Fabry-Perot," http://physics-animations.com/sensors/English/interf.htm, pp. 1-5, online publication.
File history of U.S. Pat. No. 5,798,521 (69 pages).
File history of U.S. Pat. No. 6,256,090 (126 pages).
File history of U.S. Pat. No. 6,470,205 (64 pages).
Non-Final Office Action for related U.S. Appl. No. 11/678,016, mailed Aug. 31, 2010 (30 pages).
PCT International Preliminary Report on Patentability for International Patent Application No. PCT/US2007/062617, report issued on Aug. 26, 2008 (7 pages).
PCT International Search Report for International Patent Application No. PCT/US2006/026218, mailed Dec. 12, 2006 (2 pages).
PCT International Search Report for International Patent Application No. PCT/US2005/007108, mailed Jun. 27, 2005 (4 pages).
PCT International Search Report for International Patent Application No. PCT/US2007/064728, mailed Jul. 31, 2007 (7 pages).
PCT International Search Report and Written Opinion for International Patent Application No. PCT/US2008/082236, mailed Oct. 16, 2009 (16 pages).
PCT International Search Report and Written Opinion for International Patent Application No. PCT/US2008/001505, mailed Dec. 3, 2008 (8 pages).
PCT International Search Report and Written Opinion for International Patent Application No. PCT/US2008/073215, mailed Jan. 21, 2009 (12 pages).
PCT International Search Report and Written Opinion for International Patent Application No. PCT/US2007/064728, mailed Jul. 31, 2007 (13 pages).
PCT International Search Report and Written Opinion for International Patent Application No. PCT/US2008/060936, mailed Nov. 6, 2008 (12 pages).
PCT Written Opinion of the International Searching Authority for International Patent Application No. PCT/US2006/026218, mailed Dec. 12, 2006 (7 pages).
PCT Written Opinion of the International Searching Authority for International Patent Application No. PCT/US2005/007108, received Jun. 23, 2015 (6 pages).
Abouraddy et al., "Towards multimaterial multifunctional fibres that see, hear, sense, and communicate," Nature Materials, May 2007, pp. 336-342, vol. 6.
"Speciality Guidewires," Retrieved from the Internet: http://www.galtmedical.com/pdf/Guidewires.pdf, retrieved on Jun. 18, 2014 (2 pages).
Berthold, III, "Historical Review of Microbend Fiber-Optic Sensors," Journal of Lightwave Technology, Jul. 1995, pp. 1193-1199, vol. 13 No. 7.
Blandino et al., "Three-Dimensional Shape Sensing for Inflatable Booms," 46th AIAA/ASME/ASCE/AHS/ASC Structures, Structural Dynamics & Materials Conference, Conference Dates: Apr. 18-21, 2005, Austin, Texas (10 pages).
Capouilliet et al., "A Fiber Bragg Grating Measurement System for Monitoring Optical Fiber Strain," IWCS/FOCUS Internet Conference, Nov. 12-15, 2001 (9 pages).

(56) References Cited

OTHER PUBLICATIONS

Childers et al., "Recent developments in the application of optical frequency domain reflectometry to distributed Bragg grating sensing," Luna Innovations and NASA Langley Research Center joint PowerPoint presentation (26 pages).
Danisch et al., "Bend Enhanced Fiber Optic Sensors in a Teleoperation Application," Fiber Optic and Laser Sensors XI, 1993, pp. 73-85, SPIE vol. 2070.
Danisch et al.,"Spatially continuous six degree of freedom position and orientation sensor" (9 pages).
Davis, et al., "Fiber-Optic Bragg Grating Array for Shape and Vibration Mode Sensing," May 1994, pp. 94-102, SPIE vol. 2191.
Davis, "Strain Survey of an F/A-18 Stabilator Spindle Using High Density Bragg Grating Arrays," Feb. 2005, Australia (33 pages).
Duncan, "Sensing Shape: Fiber-Bragg-grating sensor arrays monitor shape at a high resolution," Spie's OE Magazine, Sep. 2005, pp. 18-21.
Duncan et al., "A Distributed Sensing Technique for Aerospace Applications," American Institute of Aeronautics and Astronautics, 2004 (8 pages).
Duncan et al., "Characterization of a Fiber-Optic Shape and Position Sensor," Conference Title: Smart Structures and Materials 2006: Smart Sensor Monitoring Systems and Applications, Conference Date: Feb. 27, 2006 (11 pages).
Duncan et al., "Fiber-Optic Shape and Position Sensing," Proceedings of the 5th International Conference on Structural Health Monitoring, 2005 (8 pages).
Duncan et al., "High-Accuracy Fiber-Optic Shape Sensing," Sensor Systems and Networks: Phenomena, Technology, and Applications for NDE and Health Monitoring 2007, pp. 65301S-1-65301S-11, Proc. of SPIE vol. 6530.
Duncan et al., "Use of High Spatial Resolution Fiber-Optic Shape Sensors to Monitor the Shape of Deployable Space Structures," Space Technology and Applications Int.Forum-Staif, 2005 (7 pages).
Flockhart et al., "Two-axis bend measurement with Bragg gratings in multicore optical fiber," Optics Letters, Mar. 15, 2003, pp. 387-389, vol. 28 No. 6.
Froggatt et al., "Distributed measurement of static strain in an optical fiber with multiple Bragg gratings at nominally equal wavelengths," Applied Optics, Apr. 1, 1998, pp. 1741-1746, vol. 37 No. 10.
Froggatt et al., "High-spatial-resolution distributed strain measurement in optical fiber with Rayleigh scatter," Applied Optics, Apr. 1, 1998, pp. 1735-1740, vol. 37 No. 10.
Froggatt, "Intracore and Extracore Examination of Fiber Gratings with Coherent Detection," Thesis (PhD), 2000, pp. 1-136.
Froggatt et al., "Distributed Fiber-Optic Strain and Temperature Sensors Using Photoinduced Bragg Gratings," Masters of Science Thesis, Feb. 1995, pp. 1-16.
Gander et al., "Bend measurement using multicore optical fiber," pp. 166/OWC6-1-169/OWC6-4.
Gander et al., "Measurement of Bending in Two Dimensions Using Multicore Optical Fibre," 1998, p. 64-68, SPIE vol. 3483.
Gifford et al., "Swept-wavelength Interferometric Interrogation of Fiber Rayleigh Scatter for Distributed Sensing Applications," Fiber Optic Sensors and Applications V, 2007, pp. 67700E-1-67700E-9, Proc. of SPIE vol. 6770.
Grant et al., "Investigation of Structural Properties of Carbon-Epoxy Composites using Fiber-Bragg Gratings," Applications of Photonic Technology 5, 2002, pp. 191-199, Proc. of SPIE vol. 4833.
Grobnic et al., "Localized High Birefringence Induced in SMF-28 Fiber by Femtosecond IR Laser Exposure of the Cladding," Journal of Lightwave Technology, Aug. 2007, pp. 1996-2001, vol. 25, No. 8.
Grossman et al., "Development of microbend sensors for pressure, load, displacement measurements in civil engineering," 1994, pp. 112-125, SPIE vol. 2191.
Hayano et al., "Structural Health Monitoring System Using FBG Sensor Simultaneous Detection of Acceleration and Strain" (14 pages).
Heo et al., "Design of TR-EFPI Fiber Optic Pressure Sensor for the Medical Application" (6 pages).
Hill et al., "Fiber Bragg Grating Technology Fundamentals and Overview," Journal of Lightwave Technology, Aug. 1997, pp. 1263-1276, vol. 15, No. 8.
Hotate et al., "Proposal and experimental verification of Bragg wavelength distribution measurement within a long-length FBG by synthesis of optical coherence function," Optics Express, May 16, 2008, pp. 7881-7887, vol. 16, No. 11.
Huang et al., "Continuous arbitrary strain profile measurements with fiber Bragg gratings," Smart Materials and Structures, 1998, pp. 248-256, vol. 7.
Janssen et al., "Signal averaging in the undergraduate laboratory," Europe Journal of Physics, 1988, pp. 131-134, vol. 9.
Katsuki et al., "The Experimental Research on the Health Monitoring of the Concrete Structures Using Optical Fiber Sensor" (7 pages).
Kersey et al., "Fiber Grating Sensors," Journal of Lightwave Technology, Aug. 1997, pp. 1442-1463, vol. 15, No. 8.
Kim et al., "Micromachined Fabry-Perot Cavity Pressure Transducer," IEEE Photonics Technology Letters, Dec. 1995, pp. 1471-1473, vol. 7, No. 12.
Kirby et al., "Optimal sensor layout for shape estimation form strain sensors," 1995, pp. 367-376, SPIE vol. 2444.
Klute et al., "Fiber-Optic Shape Sensing and Distributed Strain Measurements on a Morphing Chevron," American Institute of Aeronautics and Astronautics, pp. 1-25.
Kreger et al., "Distributed strain and temperature sensing in plastic optical fiber using Rayleigh scatter," Fiber Optic Sensors and Applications VI, 2009, pp. 73160A-1-73160A-8, Proc. of SPIE vol. 7316.
Kreger et al., "High-Resolution Extended Distance Distributed Fiber-Optic Sensing Using Rayleigh Backscatter," Sensor Systems and Networks: Phenomena, Technology, and Applications for NDE and Health Monitoring, 2007, pp. 65301R-1-65301R-10, Proc. of SPIE vol. 6530.
Kunzler et al., "Damage Evaluation and Analysis of Composite Pressure Vessels Using Fiber Bragg Gratings to Determine Structural Health" (9 pages).
Lawrence et al., "Multi-Parameter Sensing with Fiber Bragg Gratings," 1996, pp. 24-31, SPIE vol. 2872.
Lawrence et al., "A Fiber Optic Sensor for Transverse Strain Measurement," Experimental Mechanics, Sep. 1999, pp. 202-209, vol. 39, No. 3.
Lee et al., "Intraoperative Use of Duel Fiberoptic Catheter for Simultaneous in Vivo Visualization and Laser Vaporization of Peripheral Atherosclerotic Obstructive Disease," Catheterization and Cardiovascular Diagnosis, 1984, pp. 11-16, vol. 10.
Lequime et al., "Fiber Optic Pressure and Temperature Sensor for Down-Hole Applications," Fiber Optic Sensors: Engineering and Applications, 1991, pp. 652-657, SPIE vol. 1511.
Lopatin et al., "Distributed Measurement of Strain in Smart Materials Using Rayleigh Scattering," 32nd International Sampe Technical Conference, Nov. 5-9, 2000, pp. 231-241.
Maas, "Shape measurement using phase shifting speckle interferometry," Laser Interferometry IV: Computer-Aided Interferometry (1991), 1992, pp. 558-568, SPIE vol. 1553.
MacDonald, "Frequency domain optical reflectometer," Applied Optics, May 15, 1981, pp. 1840-1844, vol. 20, No. 10.
Measures, Raymond et al., "Fiber Optic Strain Sensing", Fiber Optic Smart Structures, 1995, pp. 171-247, John Wiley & Sons Inc.
Meng-Chou, et al., "Fabrication of self-apodized short-length fiber Bragg gratings," Applied Optics, Sep. 1, 2003, pp. 5017-5023, vol. 42, No. 25.
Mihailov et al., "UV-induced polarization-dependent loss (PDL) in tilted fibre Bragg gratings: application of a PDL equalizer," IEE Proc.-Optoelectron., Oct./Dec. 2002, pp. 211-216, vol. 149, No. 5/6.
Miller et al., "Fiber-optic shape sensing for flexible structures," Fiber Optic Smart Structures and Skins II, 1989, pp. 399-404, SPIE vol. 1170.
Miller et al., "Shape sensing using distributed fiber optic strain measurements," Second European Workshop on Optical Fibre Sensors, 2004, pp. 528-531, Proc. of SPIE vol. 5502.
Morey et al., "Fiber-optic bragg grating sensors," Fiber Optic and Laser Sensors VII, 1989, pp. 98-107, SPIE vol. 1169.

(56) References Cited

OTHER PUBLICATIONS

Ohn et al., "Arbitrary strain profile measurement within fibre gratings using interferometric Fourier transform technique," Electronics Letters, Jul. 3, 1997, pp. 1242-1243, vol. 33, No. 14.

Pinet et al., "True challenges of disposable optical fiber sensors for clinical environment," Third European Workshop on Optical Fibre Sensors, 2007, pp. 66191Q-1-66191Q-4, Proc. of SPIE vol. 6619.

Posey et al., "Strain sensing based on coherent Rayleigh scattering in an optical fibre," Electronics Letters, Sep. 28, 2000, pp. 1688-1689, vol. 36, No. 20.

Raum et al., "Performance Analysis of a Fiber-Optic Shape Sensing System" (11 pages).

Raum, "Error Analysis of Three Dimensional Shape Sensing Algorithm," Apr. 26, 2005 (13 pages).

Reyes et al., "Tunable PDL of Twisted-Tilted Fiber Gratings," IEEE Photonics Technology Letters, Jun. 2003, pp. 828-830, vol. 15, No. 6.

Satava, "How the Future of Surgery is Changing: Robotics, telesurgery, surgical simulators and other advanced technologies," May 2006, pp. 2-21.

Sato et al., "Ground strain measuring system using optical fiber sensors," Part of the SPIE Conference on Sensory Phenomena and Measurement Instrumentation for Smart Structures and Materials, Mar. 1999, pp. 470-479, SPIE vol. 3670.

Schreiber et al., "Stress-induced birefringence in large-mode-area micro-structured optical fibers," Optics Express, May 16, 2005, pp. 3637-3646, vol. 13, No. 10.

Schulz et al., "Advanced fiber grating strain sensor systems for bridges, structures, and highways" (11 pages).

Schulz et al., "Health monitoring of adhesive joints using multi-axis fiber grating strain sensor system" (12 pages).

Soller et al., "High resolution optical frequency domain reflectometry for characterization of components and assemblies," Optics Express, Jan. 24, 2005, pp. 666-674, vol. 13, No. 2.

Soller et al., "Optical Frequency Domain Reflectometry for Single- and Multi-Mode Avionics Fiber-Optics Applications," IEEE, 2006, pp. 38-39.

Sorin, Chapter 10: Section 10.5 Optical Reflectometry for Component Characterization: Survey of Different Techniques, pp. 425-429.

Tian et al., "Torsion Measurement Using Fiber Bragg Grating Sensors," Experimental Mechanics, Sep. 2001, pp. 248-253, vol. 41, No. 3.

Trimble, "A successful fiber sensor for medical applications," Fiber Optic Sensors in Medical Diagnostics, 1993, pp. 147-150, SPIE vol. 1886.

Udd et al., "Usage of Multi-Axis Fiber Grating Strain Sensors to Support Nondestructive Evaluation of Composite Parts and Adhesive Bond Lines," pp. 1-9.

Udd, "Good Sense," Spie's OE Magazine, Aug. 2002, pp. 27-30.

Udd et al., "Multidimensional strain field measurements using fiber optic grating sensors," Smart Structures and Materials 2000: Sensory Phenomena and Measurement Instrumentation for Smart Structures and Materials, 2000, pp. 254-262, Proceedings SPIE vol. 3986.

Udd et al., "Progress on Developing a Multiaxis Fiber Optic Strain Sensor," 1997, pp. 50-56, SPIE vol. 3180.

Walker et al., "Shaping the radiation field of tilted fiber Bragg gratings," J. Opt. Soc. Am. B, May 2005, pp. 962-975, vol. 22, No. 5.

Wippich et al., "Tunable Lasers and Fiber-Bragg-Grating Sensors," The Industrial Physicist, Jun./Jul. 2003, pp. 24-27.

Wong et al., "Distributed Bragg grating integrated-optical filters: Synthesis and fabrication," J. Vac. Sci. Technol. B., Nov./Dec. 1995, pp. 2859-2864, vol. 13, No. 6.

Xu et al., "Miniature fiber optic pressure and temperature sensors," Fiber Optic Sensor Technology and Applications IV, 2005, pp. 600403-1-600403-6, Proc. of SPIE vol. 6004.

Xue et al., "Simultaneous Measurement of Stress and Temperature with a Fiber Bragg Grating Based on Loop Thin-Wall Section Beam," Applied Optics, Mar. 2, 2006, pp. 1-16.

Ye et al., "A polarization-maintaining fibre Bragg Grating interrogation system for multi-axis strain sensing," Measurement Science and Technology, 2002, pp. 1446-1449, vol. 13.

Zhang et al., "FBG Sensor Devices for Spatial Shape Detection of Intelligent Colonoscope," Proceedings of the 2004 IEEE International Conference on Robotics & Automation, Apr. 2004, pp. 835-840, Louisiana.

Zhang, "Novel shape detection systems based on FBG sensor net for intelligent endoscope," Journal of Shanghai University (English Edition), 2006, pp. 154-155, vol. 10, No. 2.

Zhang et al., "Fiber-Bragg-grating-based seismic geophone for oil/gas prospecting," Optical Engineering, Aug. 2006, pp. 084404-1-84404-4, vol. 45, No. 8.

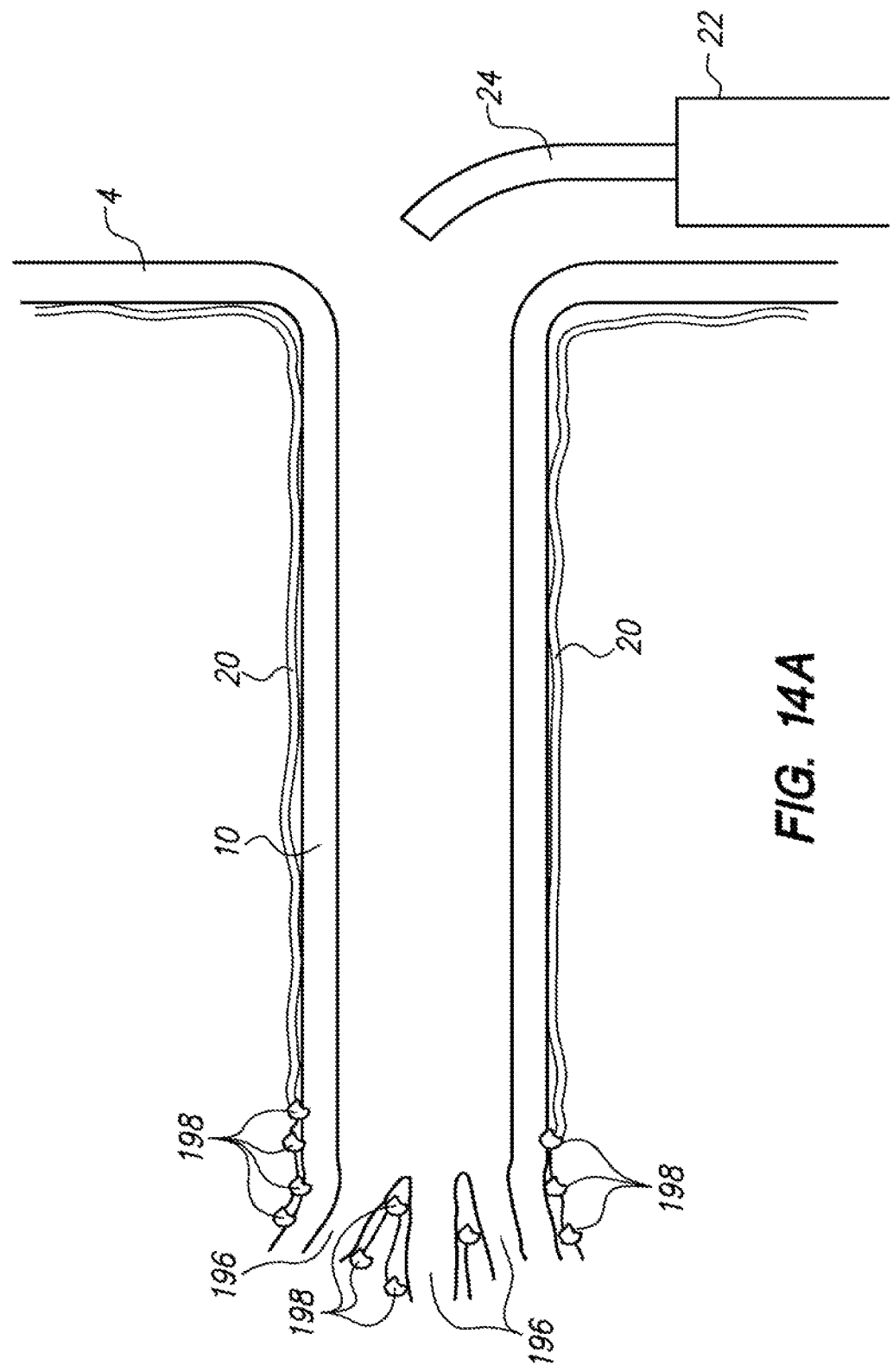

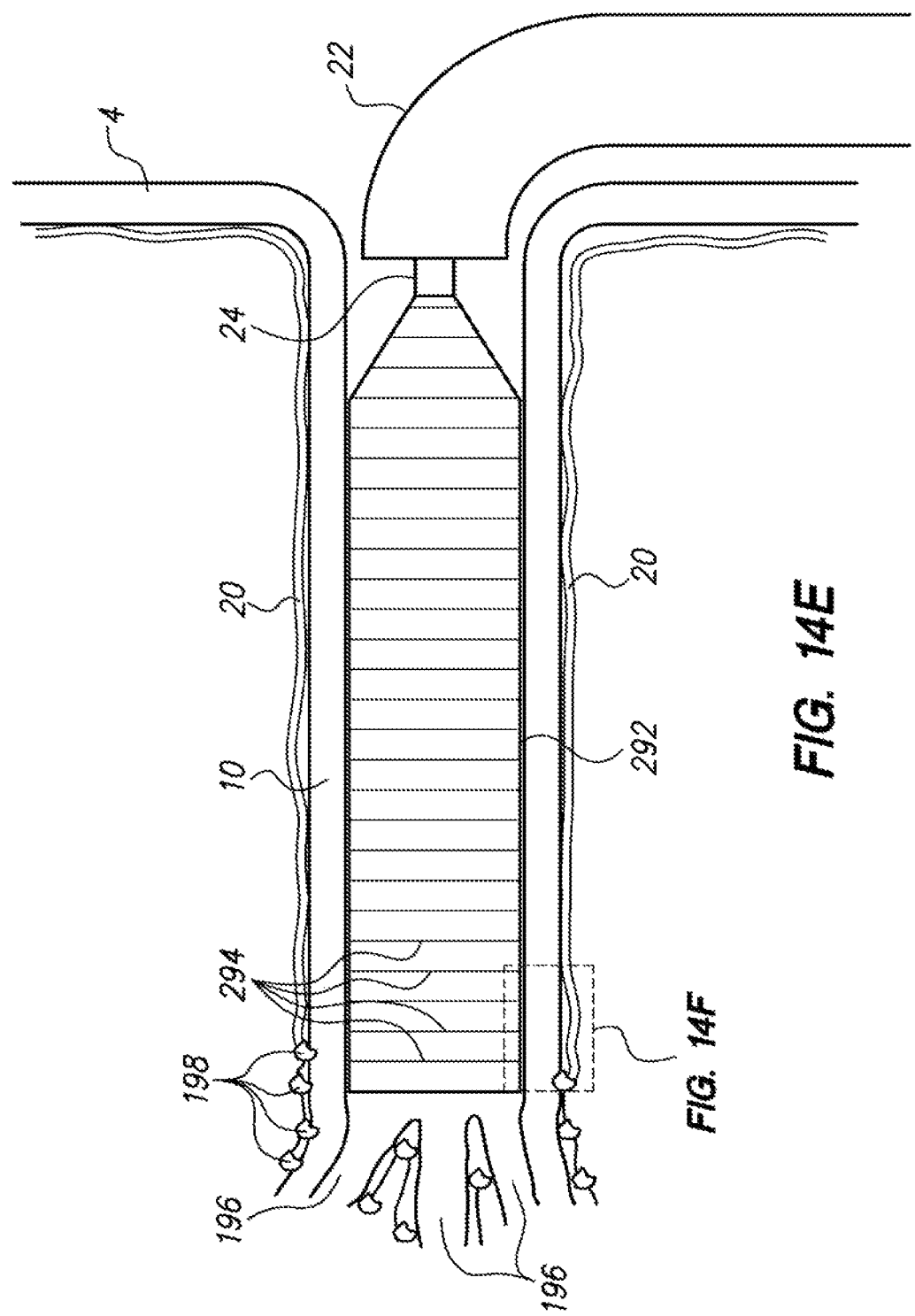

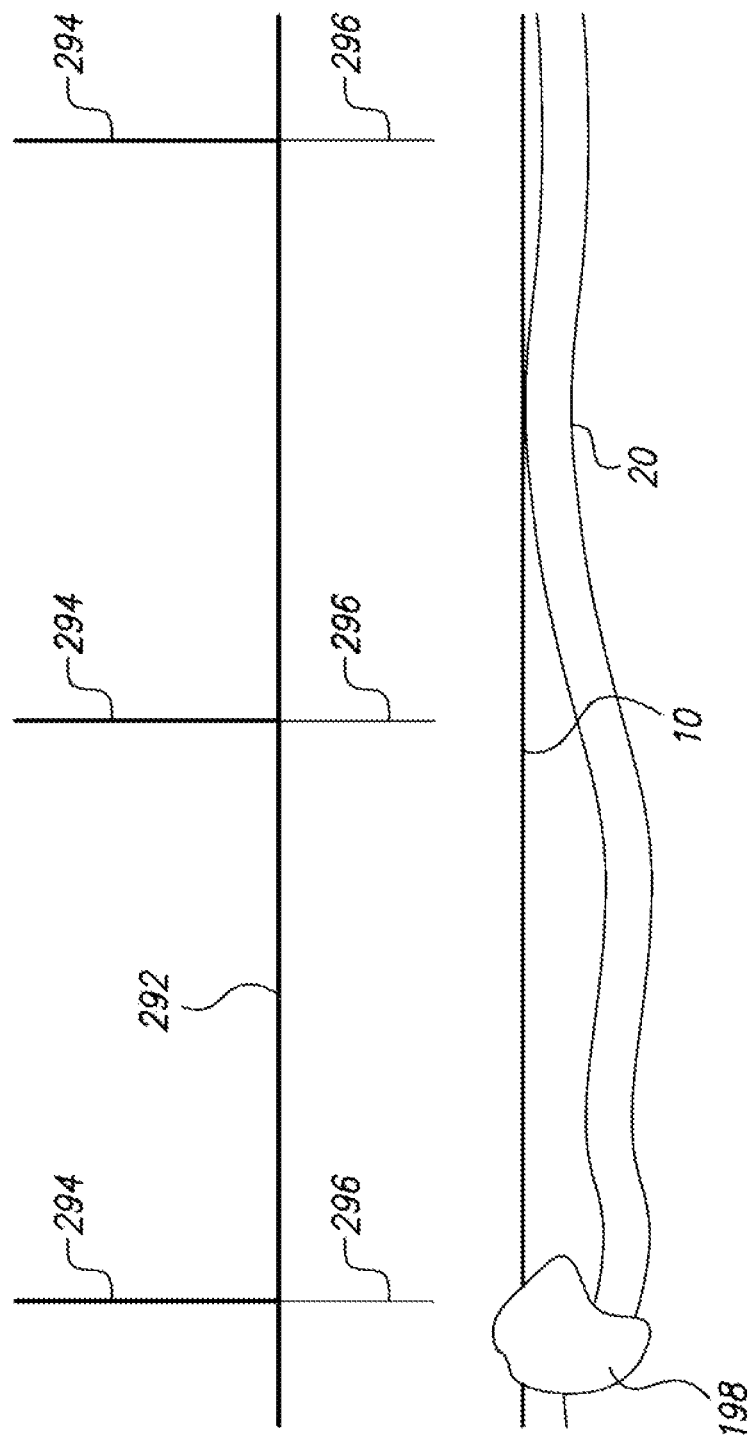

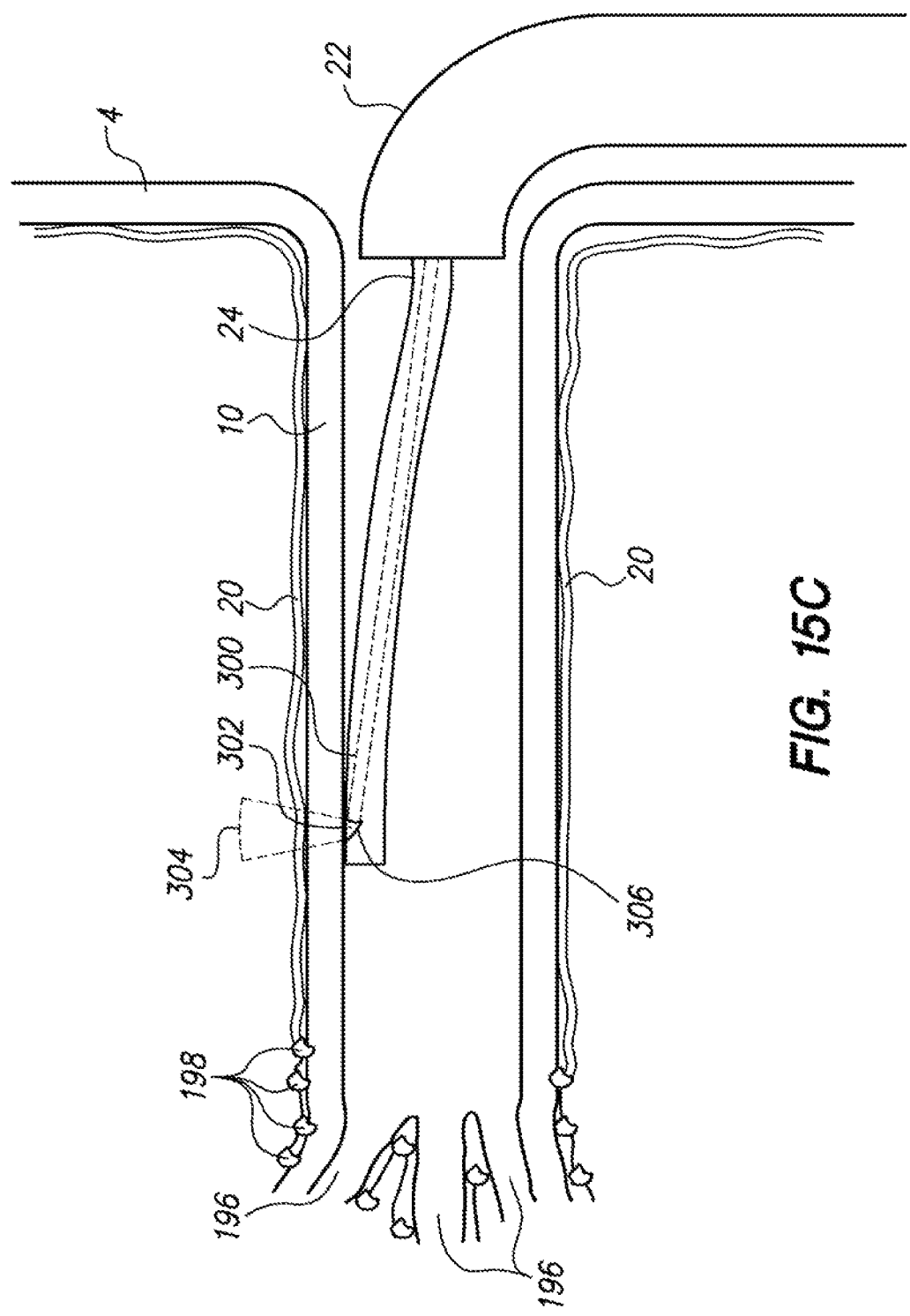

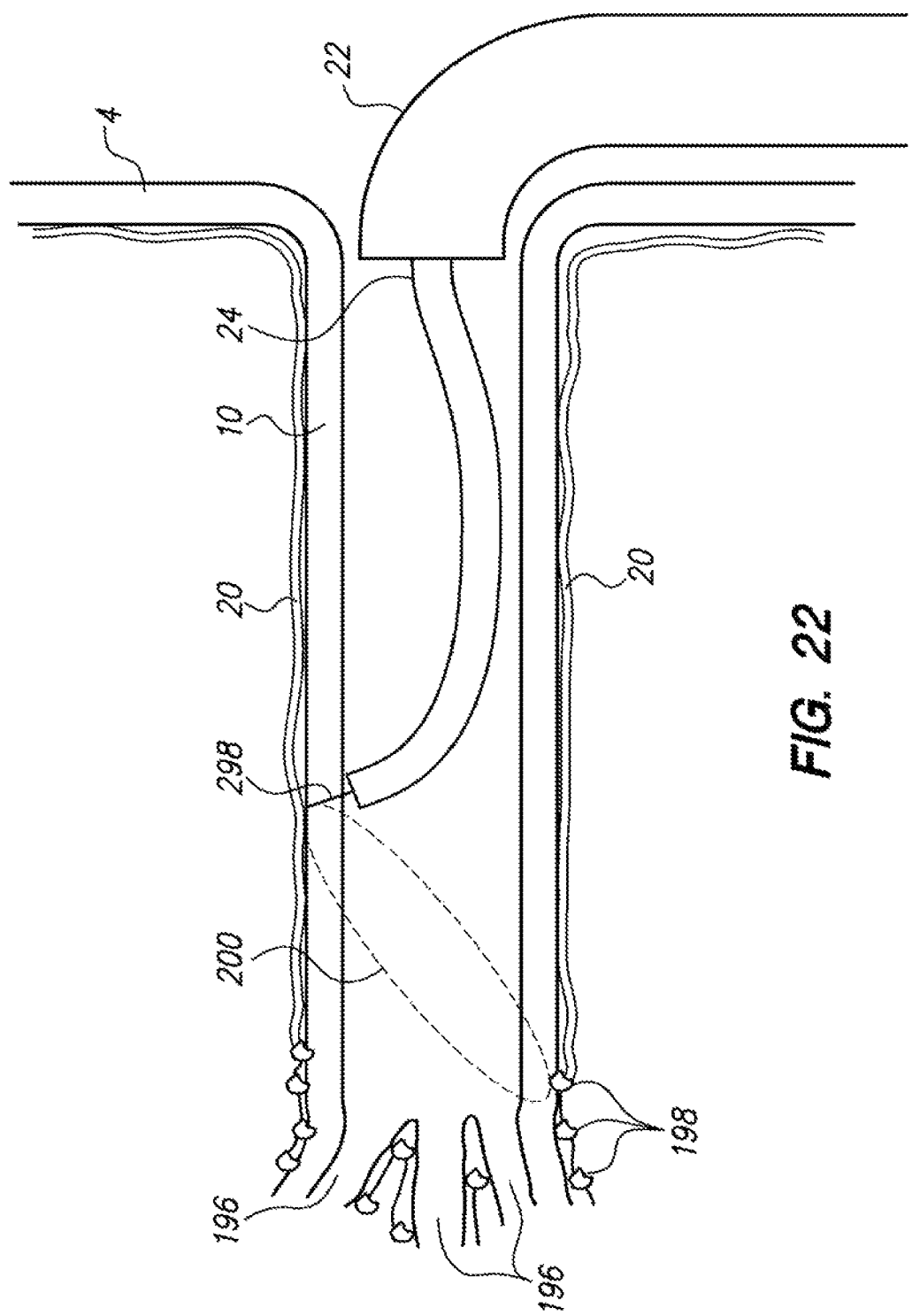

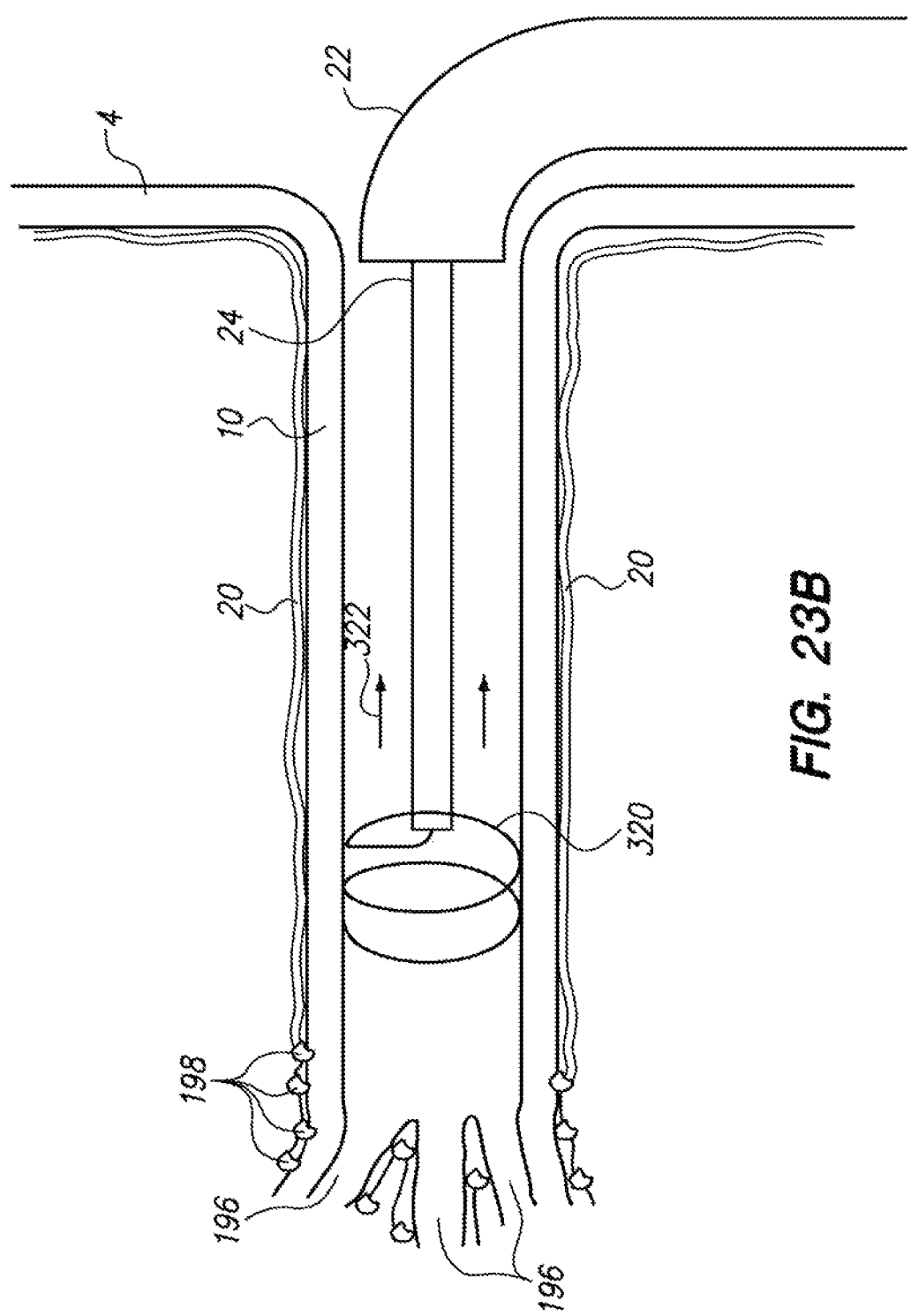

SYSTEM AND METHOD FOR ENDOLUMINAL AND TRANSLUMENAL THERAPY

CROSS REFERENCE TO RELATED APPLICATIONS

The present application is a continuation of U.S. patent application Ser. No. 13/355,321, now U.S. Patent Application Publication Number 2012/0191083, filed on Jan. 20, 2012, entitled "SYSTEM AND METHOD FOR ENDOLUMINAL AND TRANSLUMENAL THERAPY," which claims the benefit under 35 U.S.C. §119 to U.S. Provisional Patent Application No. 61/434,797, filed Jan. 20, 2011. The foregoing applications are hereby incorporated herein by reference in their entirety

FIELD OF THE INVENTION

The invention relates generally to minimally invasive medical techniques, and more particularly to therapeutic denervation treatments using endolumenal or translumenal instruments such as electromechanically or robotically operated catheters.

BACKGROUND

Elongate medical instruments, such as catheters, are utilized in many types of medical interventions. Many such instruments are utilized in what have become known as "minimally invasive" diagnostic and interventional procedures, wherein small percutaneous incisions or natural orifices or utilized as entry points for instruments generally having minimized cross sectional profiles, to mitigate tissue trauma and enable access to and through small tissue structures. One of the challenges associated with minimizing the geometric constraints is retaining functionality and controllability. For example, some minimally invasive instruments designed to access the cavities of the blood vessels and/or heart have steerable distal portions or steerable distal tips, but may be relatively challenging to navigate through tortuous vascular pathways with varied tissue structure terrain due to their inherent compliance. Even smaller instruments, such as guidewires or distal protection devices for certain vascular and other interventions, may be difficult to position due to their relatively minimal navigation degrees of freedom from a proximal location, and the tortuous pathways through which operators attempt to navigate them. To provide additional navigation and operational functionality options for minimally invasive interventions, it is useful to have an instrument platform that may be remotely manipulated with precision, such as the robotic catheter system available from Hansen Medical, Inc. under the tradename Sensei®. The elongate instruments associated with such a system may be navigated not only within the cardiovascular system, but also within other body lumens and cavities, such as those of the respiratory, gastrointestinal, urinary, and reproductive systems to address various maladies of the body, including but not limited to various paradigms cardiovascular disease. One such cardiovascular disease area of interest is hypertension, or high blood pressure, and it has been found that aspects of hypertension may be controlled with denervation therapy of the nerves of the renal plexus adjacent the renal artery. It would be valuable to have further interventional options than are presently available to address renal plexus denervation therapy.

SUMMARY

One embodiment is directed to a system for conducting denervation of the neural plexus adjacent the renal artery, comprising: a pre-shaped ablative element operatively coupled to an elongate deployment member configured to be navigated into the renal artery, the pre-shaped ablative element comprising one or more RF electrodes disposed in an arcuate pattern; and an energy source operatively coupled to the one or more RF electrodes and being configured to cause current to flow from the pre-shaped ablative element and cause localized heating sufficient to denervate nearby neural tissue. The arcuate pattern may comprise a j-curve. The j-curve may have a substantially constant radius of curvature. The arcuate pattern may comprise at least a portion of a spiral pattern. The arcuate pattern may comprise at least one full helical loop of a spiral pattern. The pre-shaped ablative element may be sufficiently flexible such that it may be delivered to a location adjacent to the subject neural tissue in a compressed form, before being utilized to cause the localized heating in an expanded form. The system further may comprise an atraumatic tip member coupled to a distal end of the pre-shaped ablative element and configured to prevent piercing of tissue structures near the subject neural tissue. The pre-shaped ablative element may have an outer diameter configured to facilitate pullback of the pre-shaped ablative element while current is flowing from the pre-shaped ablative element, to cause an elongate lesion of denervation of nearby neural tissue. The elongate deployment member may comprise an electromechanically steerable catheter. The system further may comprise a robotic instrument driver operatively coupled between the electromechanically steerable catheter and a control computing system, the robotic instrument driver configured to move one or more control elements of the electromechanically steerable catheter in response to signals transmitted from the control computing system to cause navigation movement of the electromechanically steerable catheter.

Another embodiment is directed to a method for conducting a denervation process upon the neural plexus adjacent the renal artery, comprising: navigating a pre-shaped ablative element into the renal vein; imaging targeted portions of the neural plexus from inside of the renal vein to create an anatomic map of the targeted portions; creating an electrical mapping of one or more neural strands comprising the targeted portions; and denervating the targeted portions by passing current through the pre-shaped ablative element while placing the pre-shaped ablative element in one or more desired configurations relative to the targeted portions, the configurations based at least in part upon the anatomic map and electrical mapping. The pre-shaped ablative element may comprise an arcuate pattern. The arcuate pattern may comprise a j-curve. The j-curve may have a substantially constant radius of curvature. The arcuate pattern may comprise at least a portion of a spiral pattern. The arcuate pattern may comprise at least one full helical loop of a spiral pattern. The pre-shaped ablative element may be sufficiently flexible such that it may be delivered to a location adjacent to the subject neural tissue in a compressed form, before being utilized to cause the localized heating in an expanded form. The method further may comprise transforming the pre-shaped ablative element from a compressed form to an expanded form in situ before denervating the targeted portions. The method further may comprise moving the pre-shaped ablative element relative to the targeted portions while passing current through the pre-shaped ablative element to cause an elongate lesion of denervation of nearby neural tissue. Moving may be actuated by manual or electromechanical pullback of the pre-shaped ablative element.

BRIEF DESCRIPTION OF THE DRAWINGS

FIGS. 14A-14H illustrate various aspects of a system for renal neuroplexus diagnostics and intervention in accordance with the present invention.

FIGS. 15A-15D illustrate various aspects of a system for renal neuroplexus diagnostics and intervention in accordance with the present invention, wherein OCT imaging techniques may be employed.

FIG. 22 illustrates an embodiment wherein a longitudinally displaced pattern may be used in a denervation treatment.

FIGS. 23A-23C illustrate an embodiment wherein a pullback technique may be utilized in a denervation treatment with a pre-shaped spiral instrument.

DETAILED DESCRIPTION

Figure 1:
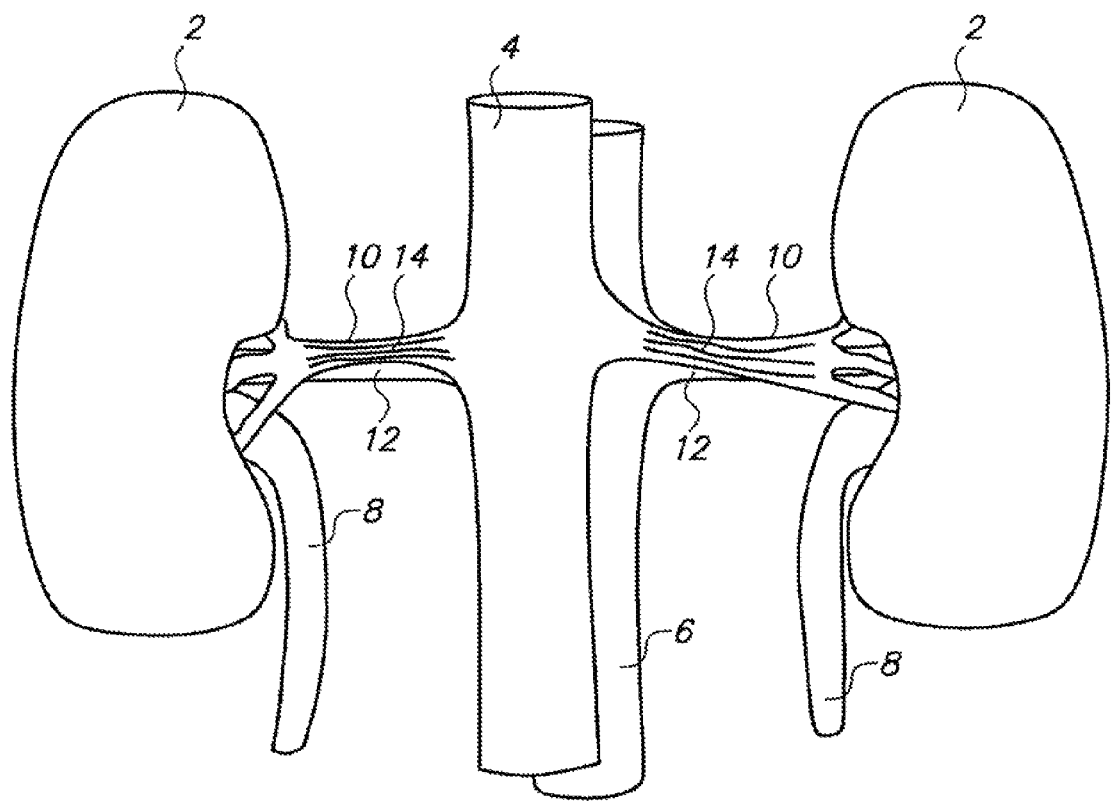
FIG. 1 illustrates certain aspects of renal vascular and neuroanatomy.
Figure 2:
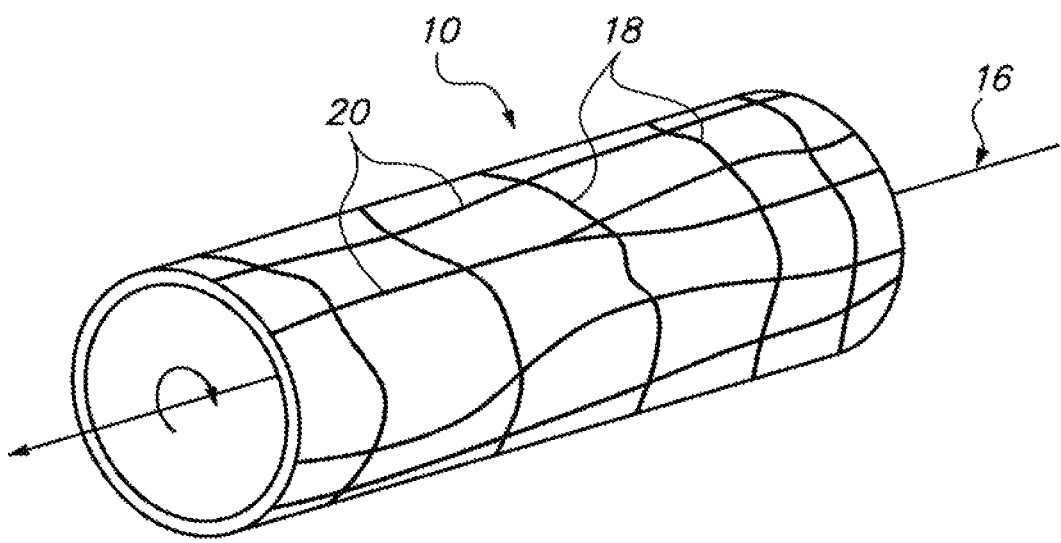
FIG. 2 illustrates a close-up view of a portion of a renal artery as well as certain portions of an associated renal nerve plexus.

Referring to FIG. 1, the kidneys (2) are shown in relation to the aorta (4), vena cava (6), ureters (8), renal veins (12) and portions of the neural anatomy of the renal plexus (14), which is coupled to the renal arteries (10). Referring to FIG. 2, a close-up orthogonal view of a portion of a renal artery (10) is shown, with bands of contractile smooth muscle tissue (18) surrounding the longitudinal axis (16) circumferentially, and with strands of renal nerves (20) coupled to the renal artery (10), generally longitudinally along the renal artery (10). These strands of renal nerves (20) comprise the renal nerve plexus, or renal plexus, which may be embedded within the adventitia of the renal artery (10). This nerve plexus extends along the renal artery until it joins the parenchyma of the kidney (2). As briefly described above, hypertension and other diseases such as heart failure and chronic kidney disease are a few of the disease states that result from chronic activation of the sympathetic nervous system, especially the renal sympathetic nervous system, which comprises the renal plexus. Chronic activation of the sympathetic nervous system is a maladaptive response that drives the progression of these disease states. Indeed, the renal sympathetic nervous system has been identified as a major contributor to the complex pathophysiology of hypertension, various states of volume overload (such as congestive heart failure), and progressive heart disease, in experimental and clinical research studies. Given the knowledge that hypertension is commonly neurogenic, there are new clinical intervention paradigms evolving whereby an attempt is made to locate and ablate strands of renal nerves (20) comprising the renal plexus from the inside of the renal artery, via an endovascular approach. Various challenges are presented with such an approach, including locating and appropriately denervating the nerve strands without damaging or necrosing the tissue of the renal artery wall. In investigating extravascular approaches (i.e., approaching the renal plexus from outside of the walls of the renal artery), it has been determined that one of the key challenges is controllably navigating and operating an instrument to a retroperitoneal location whereby the renal plexus may be more directly denervated via radiofrequency ablation or other techniques. An electromechanically, or "robotically", operated elongate instrument control system provides important functionality for such a challenge.

Figure 3:
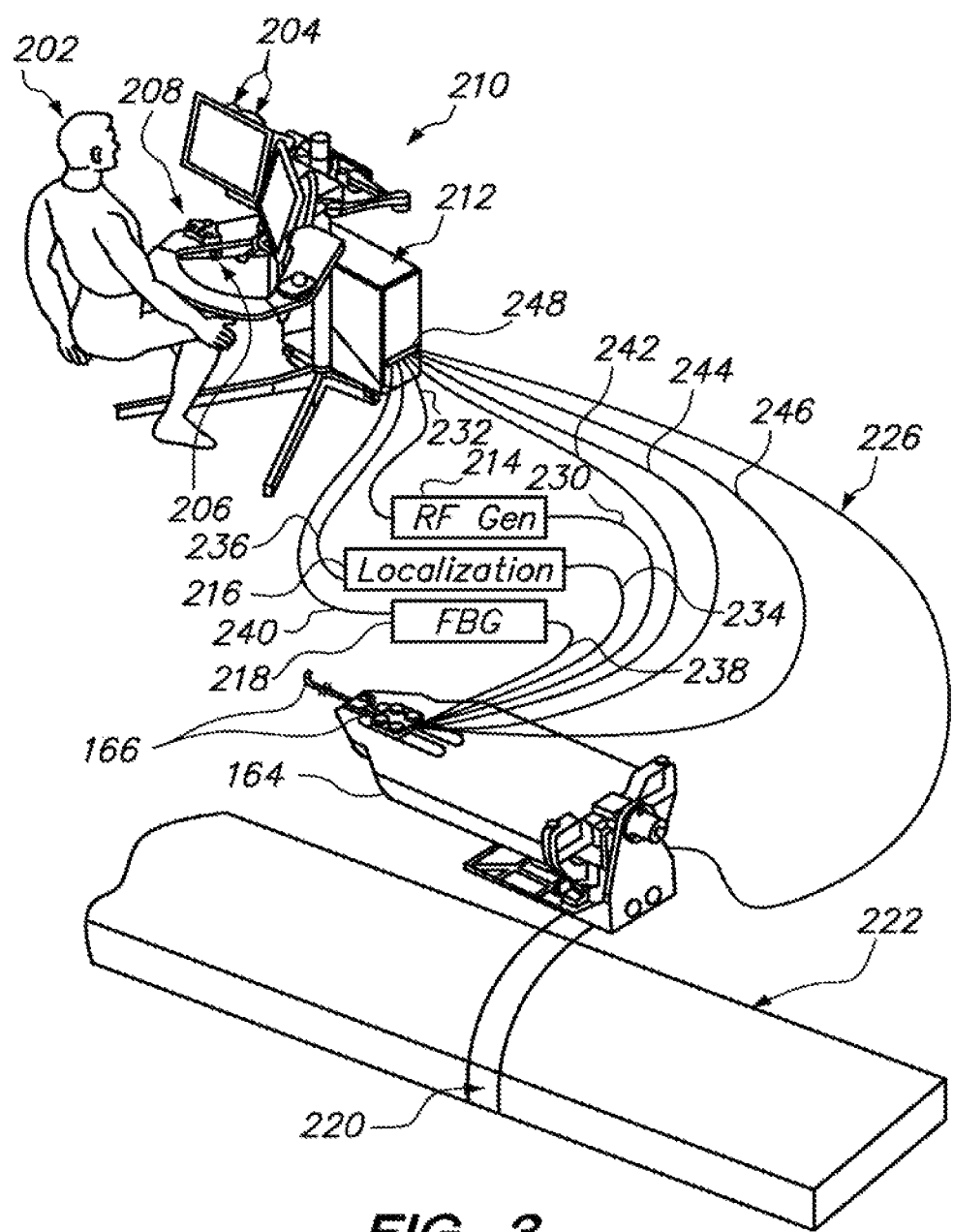
FIG. 3 illustrates a robotic catheter system configured for conducting minimally invasive medical interventions.

Referring to FIG. 3, a robotic catheter system is depicted having an operator workstation (210) comprising a master input device (206), control button console (208), and a display (204) for the operator (202) to engage. In the depicted embodiment, a controller or control computer configured to operate the various aspects of the system is also located near the operator (202). The controller (212) comprises an electronic interface, or bus (248), configured to operatively couple the controller (212) with other components, such as an electromechanical instrument driver (164), RF generator (214), localization system (216), or fiber bragg shape sensing and/or localization system (218), generally via electronic leads (232, 230, 236, 234, 240, 238, 242, 244, 246, 226). Electromechanically or robotically controlled catheter systems similar to that depicted in FIG. 3 are available from Hansen Medical, Inc. under the tradename Sensei®, and described, for example, in U.S. patent application Ser. Nos. 11/481,433, 11/073,363, 11/678,001 ("Intellisense") and Ser. No. 11/637,951, each of which is incorporated by reference in its entirety. In the depicted embodiment, the controller (212) preferably is operatively coupled (232) to the RF generator (214) and configured to control outputs of the RF generator (214), which may be dispatched via electronic lead (230) to the disposable instrument assembly (166). Similarly, the controller (212) preferably is operatively coupled (236) to a localization system, such as an electromagnetic or potential difference based localization system (216), such as those available under the tradenames CartoXP® and EnSite® from Biosense Webster, Inc., and St. Jude Medical, Inc., respectively. The localization system (216) preferably is operatively coupled via one or more leads (234) to the instrument assembly (166), and is configured to determine the three dimensional spatial position, and in certain embodiments orientation, of one or more sensors coupled to a distal portion of the instrument assembly relative to a coordinate system relevant to the controller and operator, such as a world coordinate system. Such position and/or orientation information may be communicated back to the controller (212) via the depicted electronic lead (236) or other signal communication configuration such as a wireless data communication system (not shown), to enable the controller (212) and operator (202) to understand where the distal portion of the instrument assembly (166) is in space—for control and safety purposes. Similarly, a fiber opticlocalization and/or shape sensing system (218) may be coupled between the controller (212) and instrument assembly (166) to assist with the determination of position and shape of portions of the instrument assembly, thermal sensing, contact sensing, and load sensing, as described, for example, in the aforementioned incorporated patent applications.

Various types of shape sensing fibers may be used in the fiber optic localization and/or shape sensing system (218). It is well known that by applying the Bragg equation (wavelength=2*d*sin(theta)) to detect wavelength changes in reflected light, elongation in a diffraction grating pattern positioned longitudinally along a fiber or other elongate structure maybe be determined. Further, with knowledge of thermal expansion properties of fibers or other structures which carry a diffraction grating pattern, temperature readings at the site of the diffraction grating may be calculated. "Fiberoptic Bragg grating" ("FBG") sensors or components thereof, available from suppliers such as Luna Innovations, Inc., of Blacksburg, Va., Micron Optics, Inc., of Atlanta, Ga., LxSix Photonics, Inc., of Quebec, Canada, and Ibsen Photonics AIS, of Denmark, have been used in various applications to measure strain in structures such as highway bridges and aircraft wings, and temperatures in structures such as supply cabinets.

The use of such technology in shapeable instruments is disclosed in commonly assigned U.S. patent application Ser. Nos. 11/690,116; 11/176,598; 12/012,795; 12/106,254; 12/507,727; 12/192,033; 12/236,478; and 12/837,440. The entirety of each of the above applications is incorporated by reference herein.

In an alternative variation, a single mode optical fiber is drawn with slight imperfections that result in index of refraction variations along the fiber core. These variations result in a small amount of backscatter that is called Rayleigh scatter. Changes in strain or temperature of the optical fiber cause changes to the effective length of the optical fiber. This change in the effective length results in variation or change of the spatial position of the Rayleigh scatter points. Cross correlation techniques can measure this change in the Rayleigh scattering and can extract information regarding the strain. These techniques can include using optical frequency domain reflectometer techniques in a manner that is very similar to that associated with low reflectivity fiber gratings. A more complete discussion of these methods can be found in M. Froggatt and J. Moore, "High-spatial-resolution distributed strain measurement in optical fiber with Rayleigh scatter", Applied Optics, Vol. 37, p. 1735, 1998 the entirety of which is incorporated by reference herein.

Methods and devices for calculating birefringence in an optical fiber based on Rayleigh scatter as well as apparatus and methods for measuring strain in an optical fiber using the spectral shift of Rayleigh scatter can be found in PCT Publication No. WO2006099056 filed on Mar. 9, 2006 and U.S. Pat. No. 6,545,760 filed on Mar. 24, 2000 both of which are incorporated by reference herein. Birefringence can be used to measure axial strain and/or temperature in a waveguide. Using Rayleigh scatter to determine birefringence rather than Bragg gratings offers several advantages. First, the cost of using Rayleigh scatter measurement is less than when using Bragg gratings. Rayleigh scatter measurement permits birefringence measurements at every location in the fiber, not just at predetermined locations. Since Bragg gratings require insertion at specific measurement points along a fiber, measurement of Rayleigh scatter allows for many more measurement points. Also, the process of physically "writing" a Bragg grating into an optical fiber can be time consuming as well as compromises the strength and integrity of the fiber. Such drawbacks do not occur when using Rayleigh scatter measurement.

In one embodiment, an optical fiber sensor (238), which may or may not include Bragg gratings, may be positioned between the distal tip of one or more instruments in the assembly and coupled proximally to the optical fiber sensor interrogator (218) in a manner described in U.S. Provisional Patent application No. 61/513,488 the entirety of which is incorporated by reference herein, and outputs from such system may be electronically communicated (240) to the controller (212) to facilitate control and safety features, such as closed loop shape control of one or more portions of the instrument assembly, as described, for example, in the aforementioned incorporated references. A feedback and control lead (226) is utilized to operatively couple the instrument driver (164) to the controller. This lead (226) carries control signals from the controller (212) to various components comprising the instrument driver (164), such as electric motors, and carries control signals from the various components of the instrument driver (164), such as encoder and other sensor signals, to the controller (212). The instrument driver (164) is coupled to the operating table (222) by a setup structure (220) which may be a simple structural member, as depicted, or a more complicated movable assembly, as described in the aforementioned incorporated references. A bus configuration (248) couples the various depicted leads (226, 246, 244, 242, 240, 236, 232) with the controller (212). Alternatively, wireless configurations may be utilized.

Figure 4:
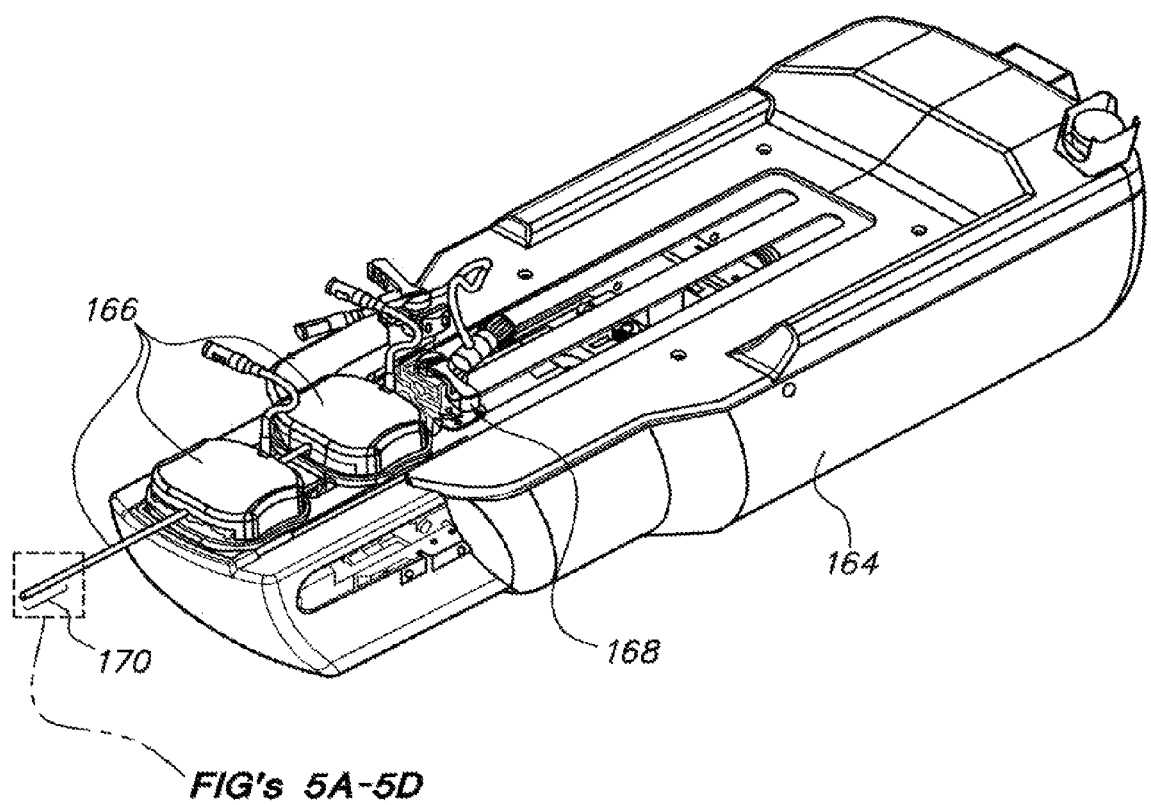
FIG. 4 illustrates an instrument driver and instrument assembly of a robotic catheter system configured for conducting minimally invasive medical interventions.

Referring to FIG. 4, an orthogonal view of an instrument driver (164) and instrument assembly (166) is depicted, this configuration having the ability to monitor loads applied to working members or tools placed through a working lumen defined by the instrument assembly (166). In this embodiment, such loads are determined with load sensors (168) located within the housing of the instrument driver, as described in the aforementioned incorporated references. In other embodiments, loads imparted to various tools or aspects of the instrument assembly (166) may be monitored using load sensors or components thereof which are embedded within or coupled to distal portions (170) of such tools or instrument assembly portions.

Figure 5A:
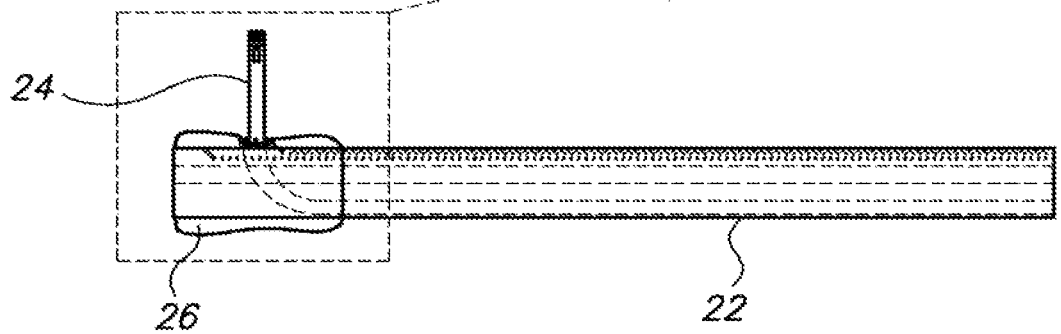
FIGS. 5A-5D illustrate various aspects of an instrumentation system for conducting a trans-lumenal renal plexus denervation procedure with one or more controllably steerable instruments and one or more controllably expandable members.
Figure 5B:
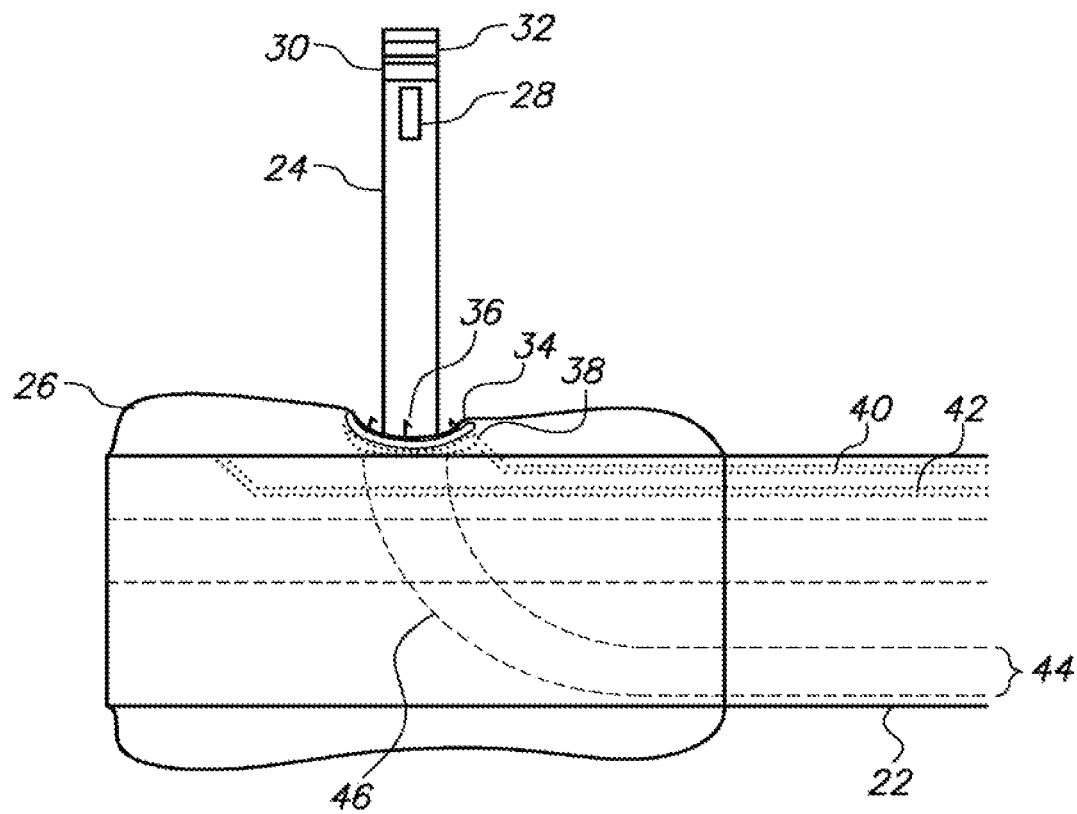
Figure 5C:
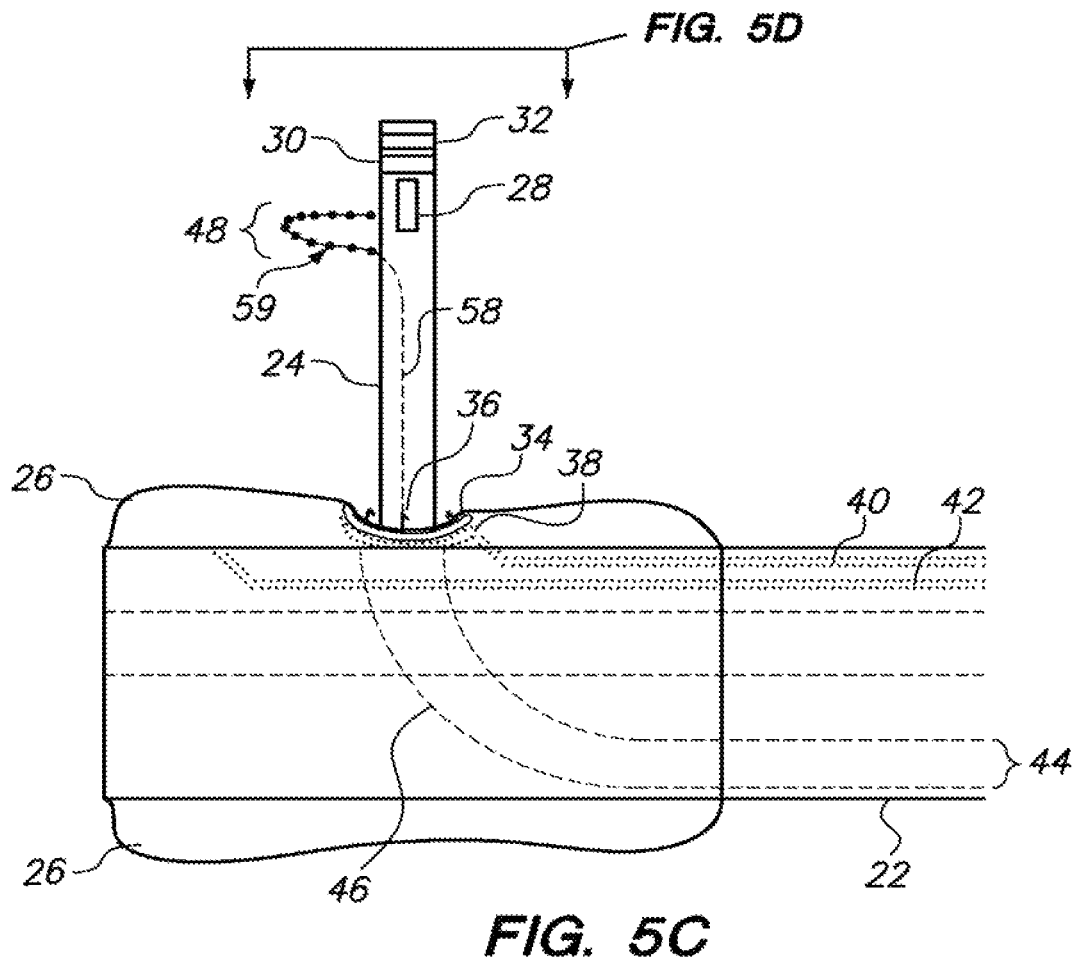

Referring to FIGS. 5A-5D, various closer views of aspects of instrument embodiments in accordance with the present invention are shown. Referring to FIG. 5A, a steerable sheath instrument (22) is depicted having a proximal interface (shown in the aforementioned incorporated by reference disclosures in reference to robotic sheath instrument embodiments) configured to be removably and driveably coupled to an instrument driver (164) such as that depicted in FIG. 4. The distal portion of the sheath instrument (22) comprises an expandable member such as a balloon, which may be controllably expanded via an inflation lumen (42), as shown in the detail view of FIG. 5B. Also shown in FIGS. 5A and 5B is an elongate steerable guide instrument (24) which may be proximally coaxially positioned through a guide insertion lumen (44) defined into the sheath instrument (22), and distally directed out through a side port formed through the balloon member (26), after being routed through an arcuate portion (46) of the guide insertion lumen (44). With the balloon member (26) in an inflated or deflated state, the depicted instrument assembly may be placed through a lumen and utilized to create a side port across the wall of the lumen. In one embodiment, a needle may initially be advanced through the sheath instrument lumen (44, 46) and across the subject tissue wall, followed by a dilator instrument and/or guidewire, which may be followed by the guide instrument (24) in an over-the-wire type technique using a working lumen defined into the guide instrument (24). As shown in FIGS. 5A and 5B, the distal portion of the elongate guide instrument (24) may be outfitted with one or more ultrasound transducers (28), one or more localization sensors (30), and one or more treatment elements (such as a radiofrequency electrode, a cryoablation reservoir, a high intensity focused ultrasound treatment transducer, a laser or other radiation emitter, or the like 32) which may be utilized to denervate nerve strands, such as those of the renal plexus. In another embodiment, the distal portion of the guide instrument (24) may be operatively coupled to an antenna, such as a microwave antenna, to sense reflected radiation, such as blackbody radiation, which may be correlated to the temperature of nearby tissues, as described, for example, in U.S. patent application Ser. No. 12/833,927, which is incorporated by reference herein in its entirety. Such an embodiment allows for direct sensing of thermal conditions in nearby tissue structures of interest—as opposed to other competing techniques such as thermocouples placed adjacent RF heating electrodes, which are more aptly configured to read the temperature of the electrodes rather than nearby tissues.

Figure 13:
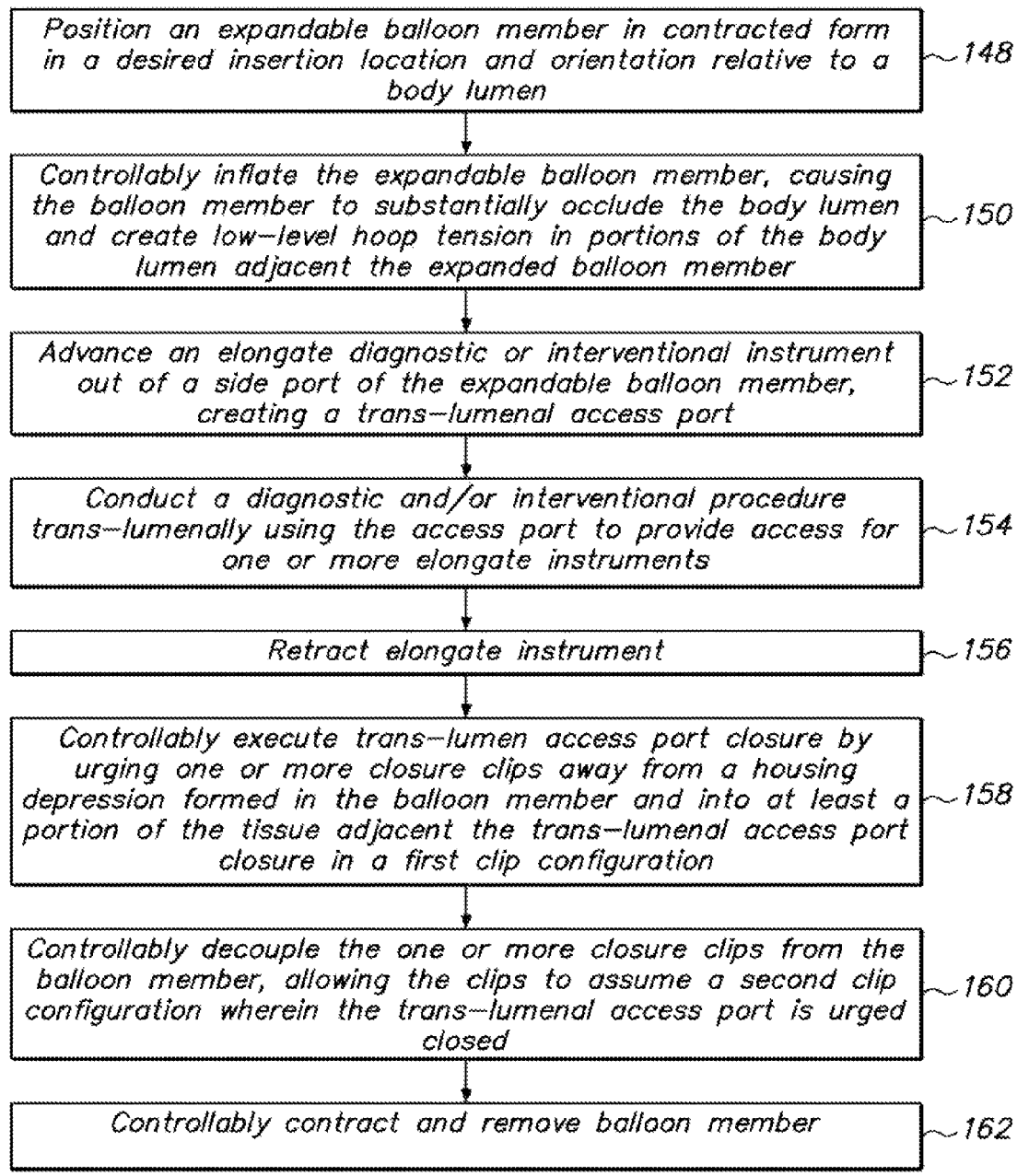
FIG. 13 illustrates various aspects of a process for creating a trans-lumenal access port from inside of a subject tissue lumen or structure, utilizing the access port for a diagnostic or interventional procedure, and closing the access port from inside of the subject tissue lumen.

Referring to the close-up view of FIG. 5B, the side port of the balloon member (26) comprises a lumen port closure configuration having one or more closure clip elements (34) constrained in an open configuration by the geometry of the balloon member (26) to which it is coupled. Upon controllable inflation of a small clip deployment bladder (38) coupled to the balloon member (26) using an inflation lumen (40), the clip (34) may be advanced outward, and small barb-like fastening members (36) configured to fasten to nearby tissue structures upon exposure and mild advancement load from the deployment bladder (38) and/or balloon member (26) inflation will engage nearby tissue structures, while the clip (34) simultaneously will become unconstrained from its coupling with the structure of the balloon member (26) and will be free to resume an unloaded configuration, preferably configured to coapt the tissue around the circumference of the access port toward itself. Suitable clips made from bioinert metals such as nitinol are available from Medtronic Corporation and were invented by Coalescent Surgical, Inc. and cleared by the FDA for a different medical application (closure of vascular anastomosis). The fastening features (36) may be sintered onto the clips, welded, coupled with a preferably bioinert adhesive, or formed or etched into the same structure that comprises the fastening element (36). Referring ahead to FIG. 13, a process for utilizing a configuration such as that depicted in FIGS. 5A and 5B to create and subsequently close a lumen side port is illustrated.

Referring to FIG. 13, after positioning an expandable balloon member in a contracted form to a desired insertion location and orientation (i.e., roll orientation relative to the longitudinal axis commonly associated with a lumen) (148), the expandable balloon member maybe controllably inflated to substantially occlude the body lumen (with the exception of flow which may be facilitated through a working throughlumen of a subject sheath instrument) and create a relatively low-level hoop tension in portions of the body lumen adjacent to the expanded balloon member (150). An elongate diagnostic and/or interventional instrument may then be advanced out of a side port of the expandable balloon member (in one embodiment, as described above, in an over-the-needle, wire, or dilator configuration), creating a trans-lumenal access port (152). Using this access port, a diagnostic and/or interventional procedure may be conducted translumenally with one or more elongate instruments (154). When the interventional procedure has been completed, the elongate instruments may be refracted (156) and a controlled closure of the translumenal access port executed by urging the one or more closure clips away from a housing depression formed in the balloon member, and into at least a portion of the tissue structure adjacent the translumenal access port, with the one or more clips maintaining their constrained (i.e., constrained until they are uncoupled from the balloon member housing interface) configurations as they are fastened to the nearby tissue (158). A bladder and associated pressure control lumen, as shown in FIG. 5B, for example, may be utilized to controllably advance the one or more clips outward, as described above. With the one or more closure clips fastened to the subject tissue structure, preferably in a pattern about the annulus of the translumenal access port, incremental pressure in the bladder or other mechanism may be utilized to uncouple the one or more closure clips from the balloon member, allowing them to assume an unloaded configuration preferably selected to cause tissue coaptation about the previous location of the translumenal access port to urge the port closed (160). With the port closed, the instruments may be withdrawn (162).

Figure 5D:
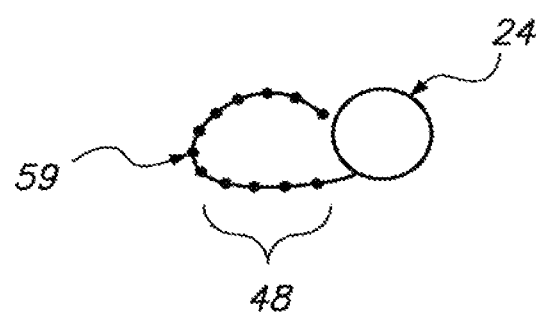

Referring back to FIG. 5C, an embodiment similar to that of FIG. 5B is depicted, with the exception that an elongate treatment probe (58), such as a bendable or steerable needle, comprising a series plurality (59) of distally-located treatment elements (akin to element 32) coupled to a helically shaped (48) treatment probe distal portion that is configured to be inserted and/or wrapped around a given tissue structure for discrete, controlled ablation of such tissue structure. The helical shape (48) is selected to minimize the risk of stenosis by longitudinally stretching out a circumferential lesion (i.e., a non-stretched purely circumferential lesion may have scar tissue expansion inward from directly opposing tissue structure portions, leaving it more vulnerable to stenosis by such scarring; the helical pitch shape 48 is configured to avoid this). An orthogonal view is depicted in FIG. 5D.

Figure 6A:
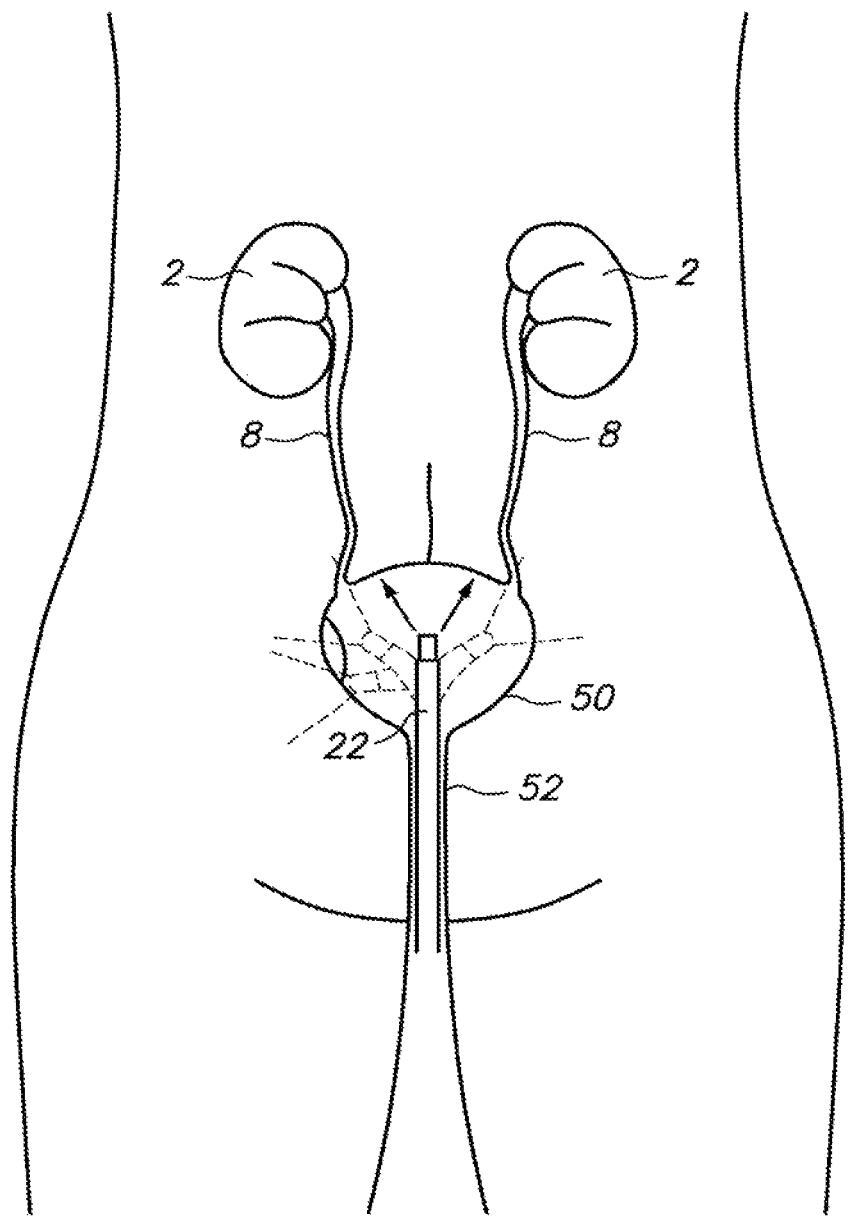
FIGS. 6A-6B illustrate various aspects of a trans-ureteral renal nerve plexus intervention utilizing the subject remotely steerable instrument system.
Figure 6B:
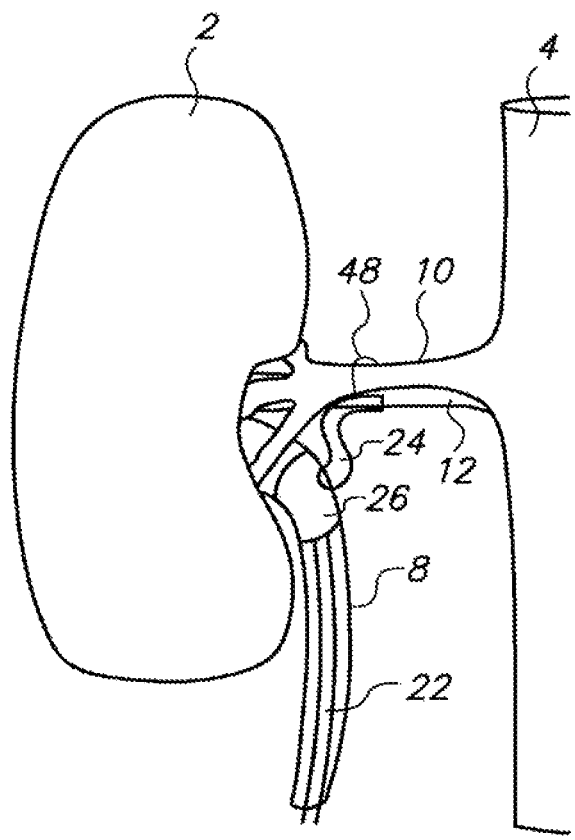
Figure 8:
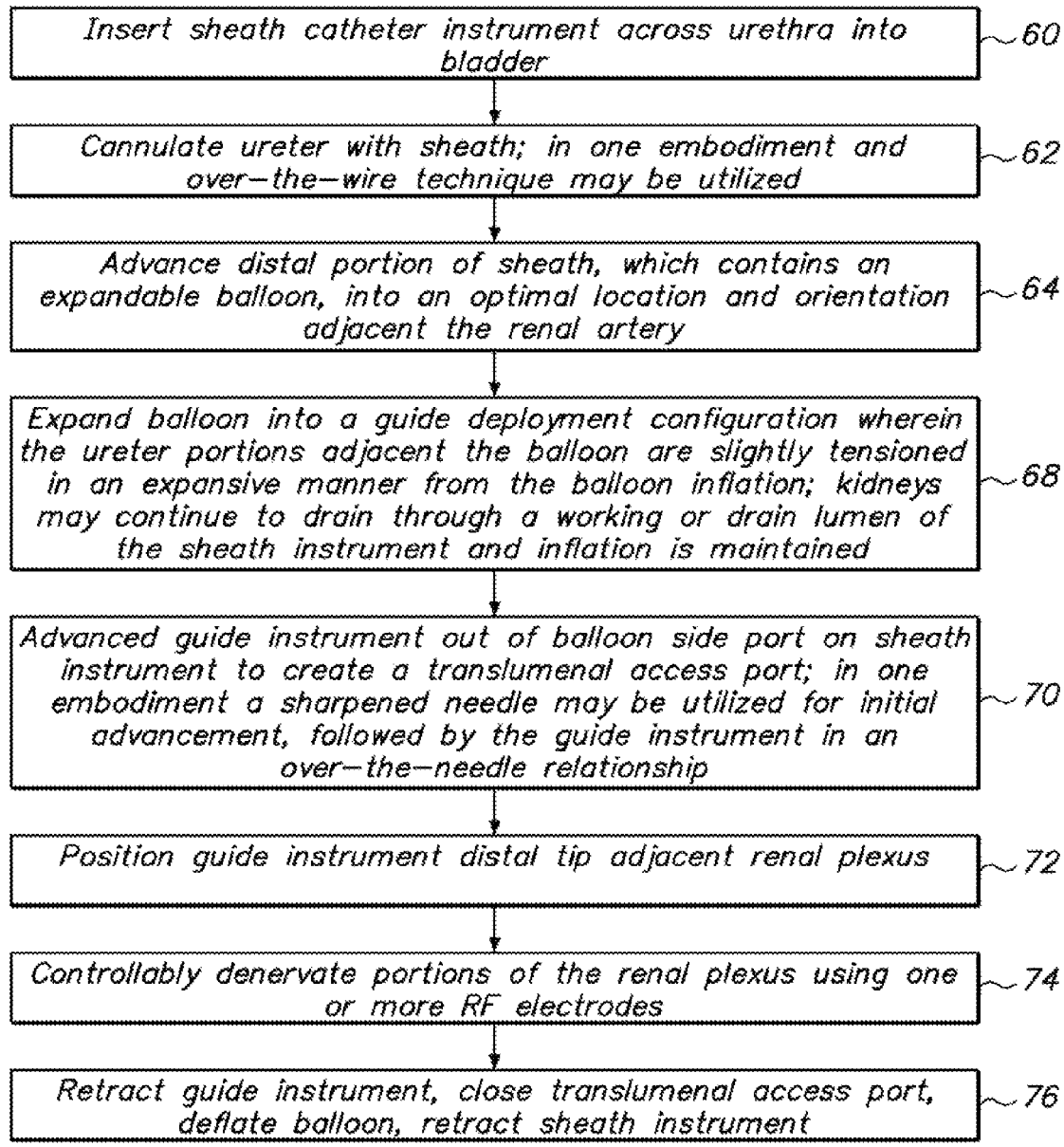
FIG. 8 illustrates various aspects of a trans-ureteral renal plexus denervation intervention.

Referring to FIGS. 6A, 6B, and 8, a trans-ureteral renal nerve plexus denervation procedure is illustrated. As shown in FIG. 6A, a guide and sheath instrument assembly similar to that depicted in FIGS. 5A and 5B may be inserted through the urethra (52) and into the bladder (50) where it may be navigated to cannulate one of the ureters (8) and be directed toward the kidney (2), as shown in FIG. 6B. Referring to FIG. 6B, with the sheath instrument (22) desirably located and oriented relative to the renal artery (10) (confirmation of which may be assisted using ultrasound, fluoroscopy, and other imaging modalities), a transcutaneous access port may be created through an expanded balloon member (26) to provide an elongate guide instrument, such as a robotically steerable guide instrument (24) with relatively immediate retroperitoneal access to the outside of the renal artery, and therefore the renal plexus. Such access may be utilized to directly ablate and/or otherwise denervate selected portions of the renal plexus. A similar configuration may be utilized to conduct a trans-lumenal diagnostic and/or interventional procedure via various other anatomical situations. For example, in an embodiment similar to that described in reference to FIGS. 5A-5D and 6A-6B, an elongate steerable instrument configuration may be utilized to move through the lower gastrointestinal tract, up into the intestine, and be utilized to cross the intestine closely adjacent the renal plexus to conduct a similar denervation procedure from a different anatomic platform. One or more stents or stentlike members may be left behind to bolster or replace the closure provided by the clip-like elements (34), and such stent or stentlike member may be subsequently removed, as directed by the physician, in a manner similar to that conducted in certain conventional ureter wound closure scenarios.

Referring to FIG. 8, a process flow for such a procedure is illustrated. With a sheath instrument advanced across a urethra and into the bladder (60), steerability and navigation capabilities of the sheath instrument may be utilized to cannulate a ureter (potentially using an over-the-wire technique) (62). The distal portion of the sheath instrument may be advanced into an optimal position and orientation for accessing the retroperitoneal space adjacent the renal artery and renal plexus (64). A balloon member may be expanded into a guide instrument deployment configuration wherein ureter portions adjacent the balloon are slightly tensioned in an expansive manner from the balloon inflation; the kidneys may continue to drain using a lumen defined through at least a portion of the balloon and/or sheath member (68). A guide member may be advanced out of a side port formed in the balloon member to create a translumenal access port (in some embodiments utilizing over the wire or over the needle techniques) (70). With the translumenal access created, the guide instrument may be advanced toward the desired neuroanatomy (72) from the outside of the renal artery, and controlled denervation accomplished using radiofrequency energy emission or other denervation modalities, as described above (74). Subsequently, the instrumentation may be retracted, the access port closed (for example, as described above), the balloon deflated, and normal function returned without the endolumenal instrumentation in place (76).

Figure 7:
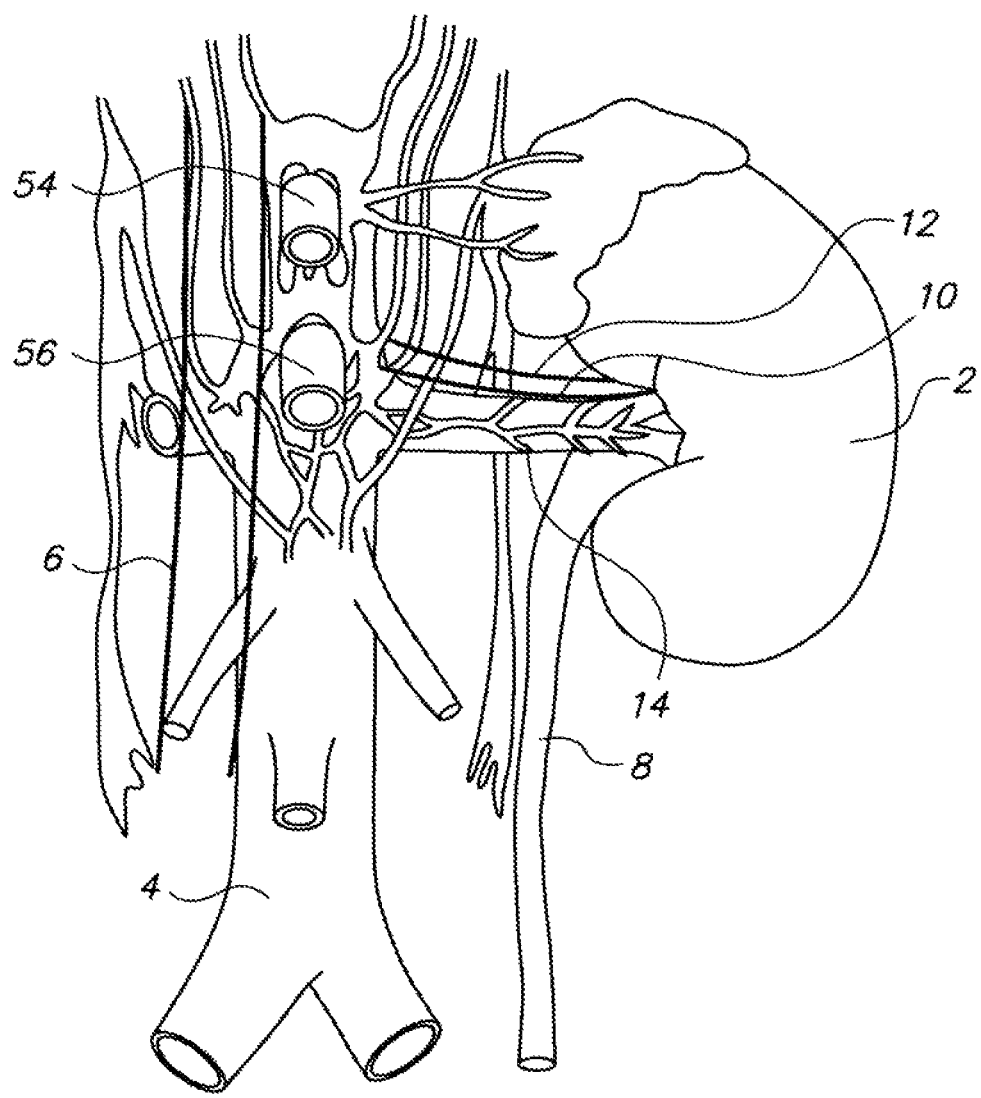
FIG. 7 depicts a close up partial view of renal, cardiovascular, and associated neuroanatomy in the abdomen adjacent the kidney.
Figure 9:
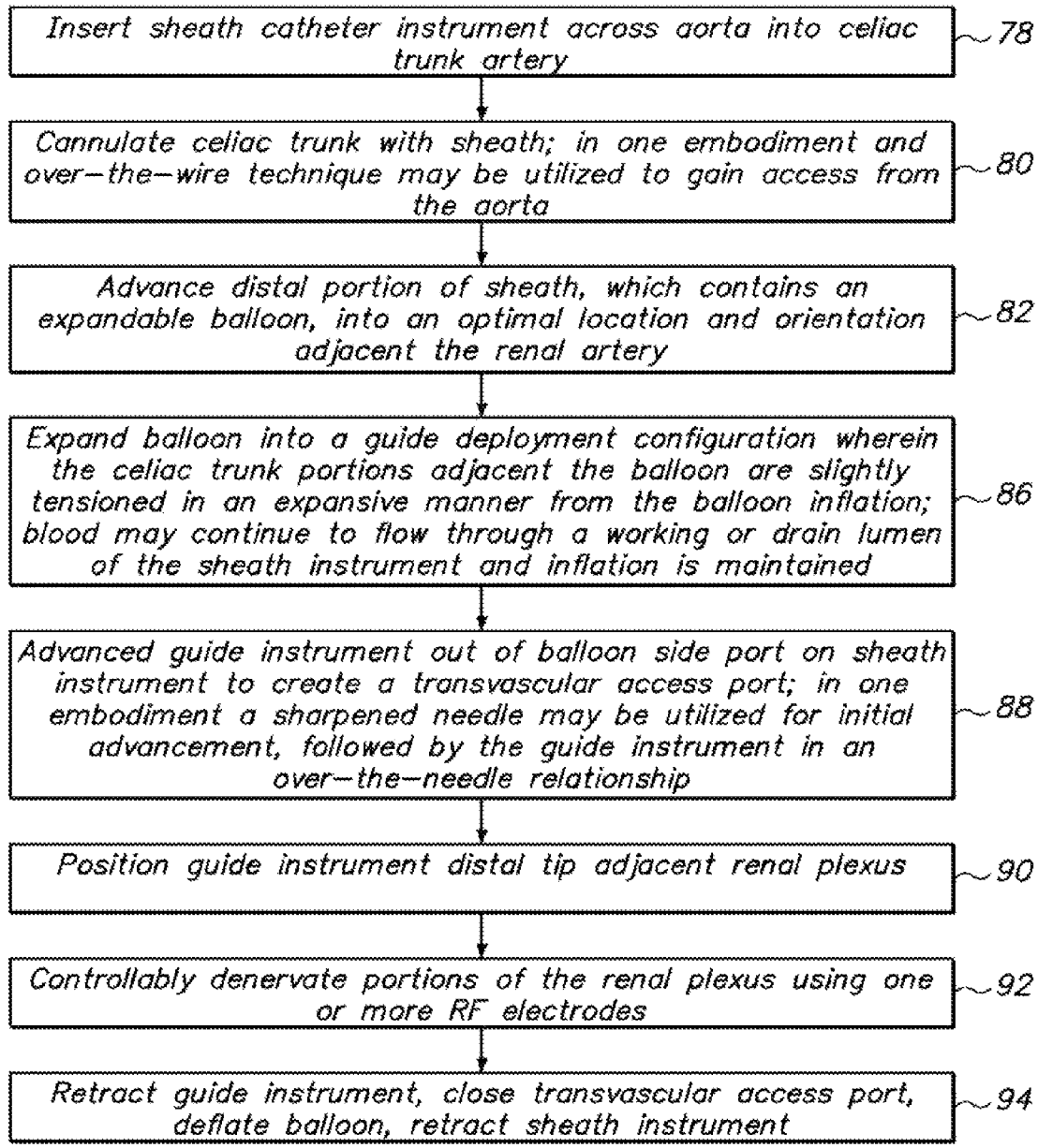
FIG. 9 illustrates various aspects of a trans-arterial renal plexus denervation intervention wherein instrumentation is taken across a portion of a wall of the celiac trunk artery.

Referring to FIG. 7, various aspects of the cardiovascular and neurological anatomy around the renal system are depicted to illustrate that there are several translumenal access opportunities to the retroperitoneal region of the renal plexus, including but not limited to the vena cava (6), the renal veins (12), the celiac trunk artery (54), and the superior mesentery artery (56). Referring to FIG. 9, a process for implementing a translumenal renal plexus denervation with a trans-celiac approach is illustrated. A sheath instrument is advanced up the aorta and into the celiac trunk artery (78). An over the wire process may be utilized to gain full access to the celiac trunk for the distal portion of the sheath instrument (80). The distal portion of the sheath may be adjusted in position and orientation to optimize a translumenal approach toward the renal plexus (82). A balloon member coupled to the distal portion of the sheath member may be expanded to slightly tension the celiac trunk portions adjacent the balloon member, and blood may continue to flow past the balloon member using a lumen formed through the balloon member (86). A guide instrument may be advanced out of a side port of the sheath instrument to create a transvascular access port (88). In one embodiment, a sharpened needle may be utilized for the initial advancement, followed by the guide instrument in an over the needle interfacing relationship. The distal portion of the guide instrument may be positioned adjacent the renal plexus (90), and one or more RF electrodes may be utilized to controllably denervate portions of the renal plexus (92). Subsequently the guide instrument may be retracted, the transvascular access port closed (for example, using one or more clip members as described above in reference to FIG. 5B), the sheath balloon member deflated, and the sheath instrument retracted to leave a complete closure (94).

Figure 10:
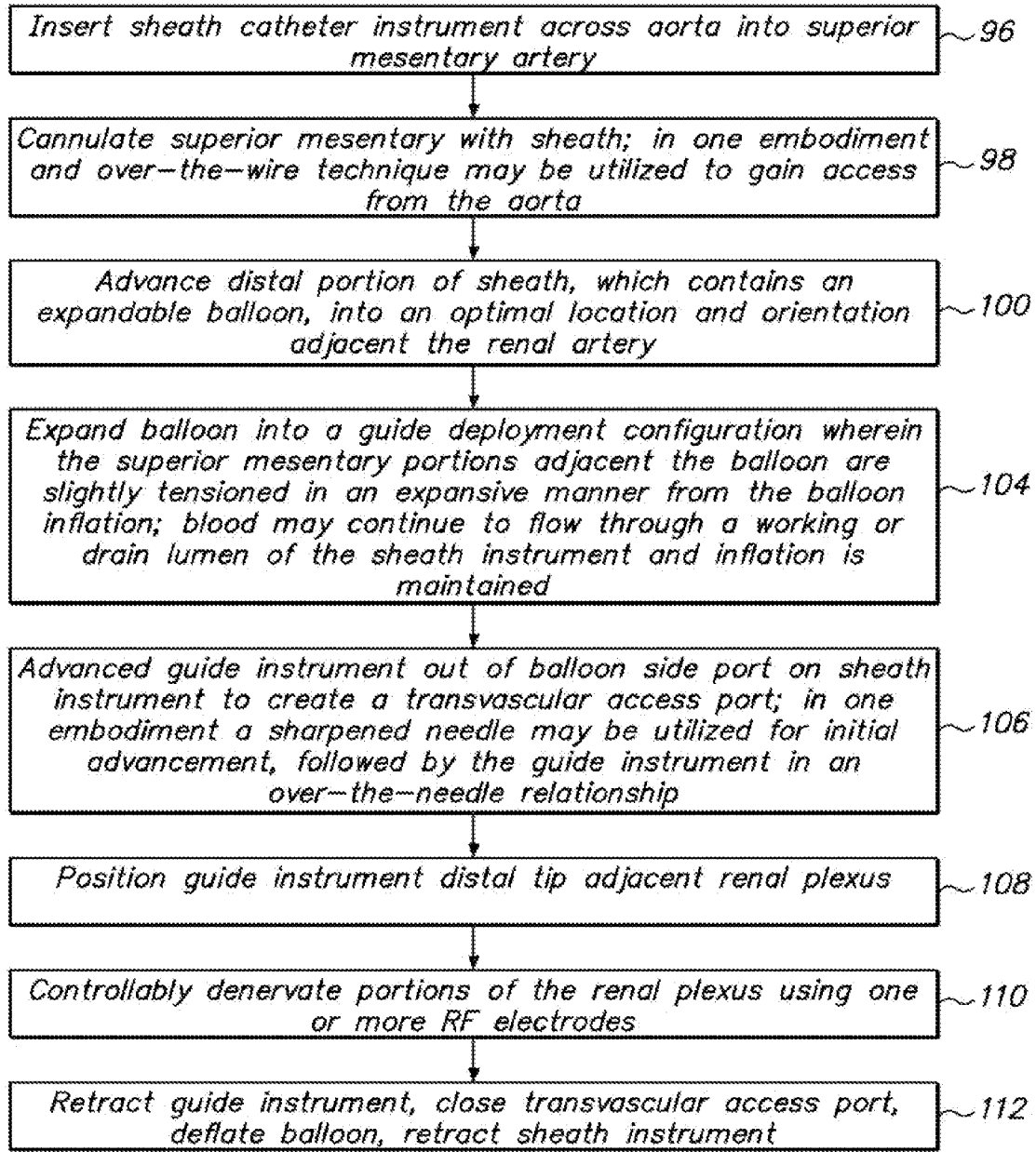
FIG. 10 illustrates various aspects of a trans-arterial renal plexus denervation intervention wherein instrumentation is taken across a portion of a wall of the superior mesentary artery.

Referring to FIG. 10, a process for implementing a translumenal renal plexus denervation with a trans-mesentary approach is illustrated. A sheath instrument is advanced up the aorta and into the superior mesentary artery (96). An over the wire process may be utilized to gain full access to the celiac trunk for the distal portion of the sheath instrument (98). The distal portion of the sheath may be adjusted in position and orientation to optimize a translumenal approach toward the renal plexus (100). A balloon member coupled to the distal portion of the sheath member may be expanded to slightly tension the superior mesentary artery portions adjacent the balloon member, and blood may continue to flow past the balloon member using a lumen formed through the balloon member (104). A guide instrument may be advanced out of a side port of the sheath instrument to create a transvascular access port (106). In one embodiment, a sharpened needle may be utilized for the initial advancement, followed by the guide instrument in an over the needle interfacing relationship. The distal portion of the guide instrument may be positioned adjacent the renal plexus (108), and one or more RF electrodes may be utilized to controllably denervate portions of the renal plexus (110). Subsequently the guide instrument may be retracted, the transvascular access port closed (for example, using one or more clip members as described above in reference to FIG. 5B), the sheath balloon member deflated, and the sheath instrument retracted to leave a complete closure (112).

Figure 11:
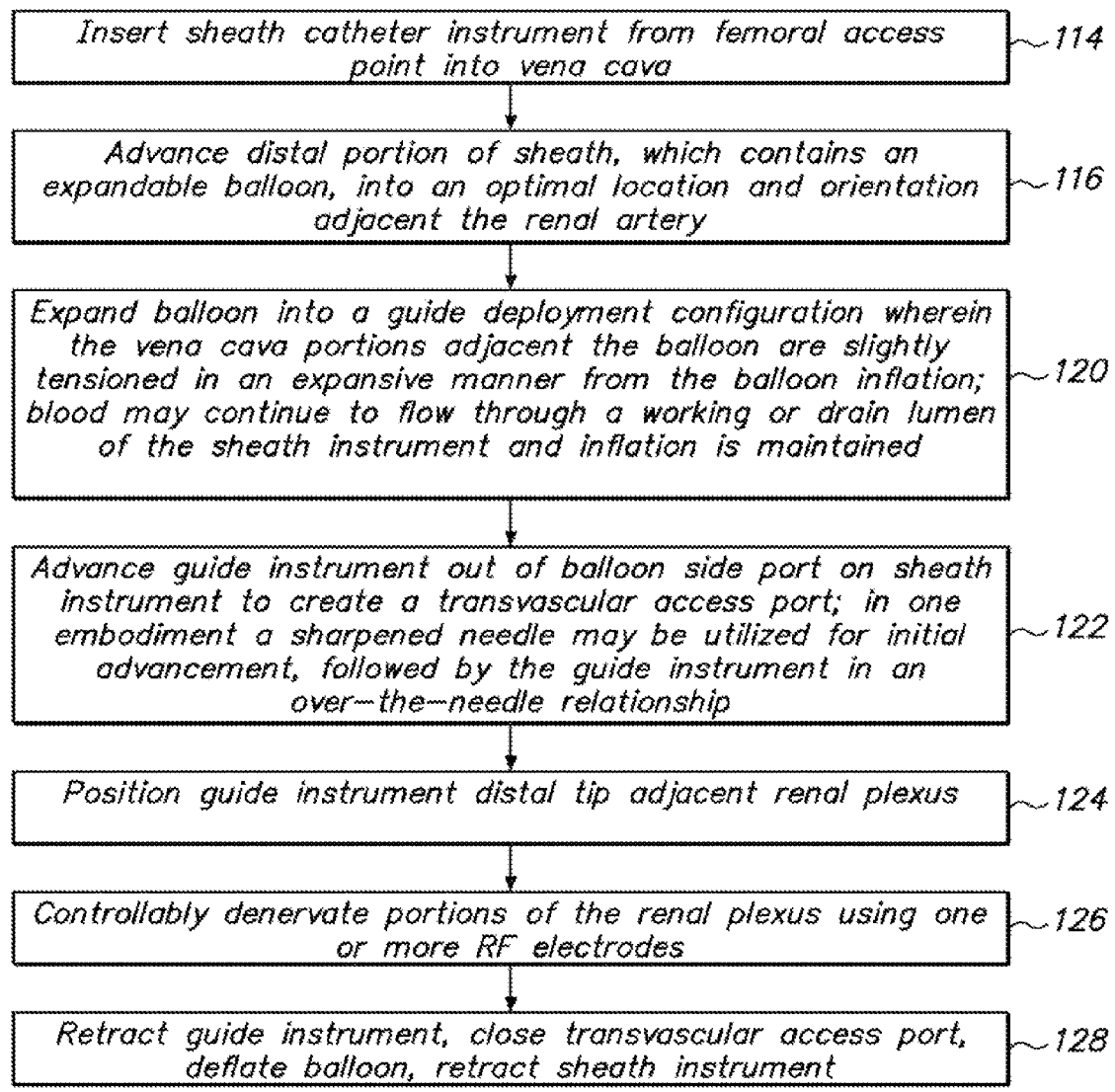
FIG. 11 illustrates various aspects of a trans-venous renal plexus denervation intervention wherein instrumentation is taken across a portion of a wall of the vena cava.

Referring to FIG. 11, a process for implementing a translumenal renal plexus denervation with a trans-vena-cava approach is illustrated. A sheath instrument is advanced up into the vena cava from a femoral or other access point (114). The distal portion of the sheath may be adjusted in position and orientation to optimize balloon member positioning for a translumenal approach toward the renal plexus (116). A balloon member coupled to the distal portion of the sheath member may be expanded to slightly tension the celiac trunk portions adjacent the balloon member, and blood may continue to flow past the balloon member using a lumen formed through the balloon member (120). A guide instrument may be advanced out of a side port of the sheath instrument to create a transvascular access port (122). In one embodiment, a sharpened needle may be utilized for the initial advancement, followed by the guide instrument in an over the needle interfacing relationship. The distal portion of the guide instrument may be positioned adjacent the renal plexus (124), and one or more RF electrodes may be utilized to controllably denervate portions of the renal plexus (126). Subsequently the guide instrument may be retracted, the transvascular access port closed (for example, using one or more clip members as described above in reference to FIG. 5B), the sheath balloon member deflated, and the sheath instrument retracted to leave a complete closure (128).

Figure 12:
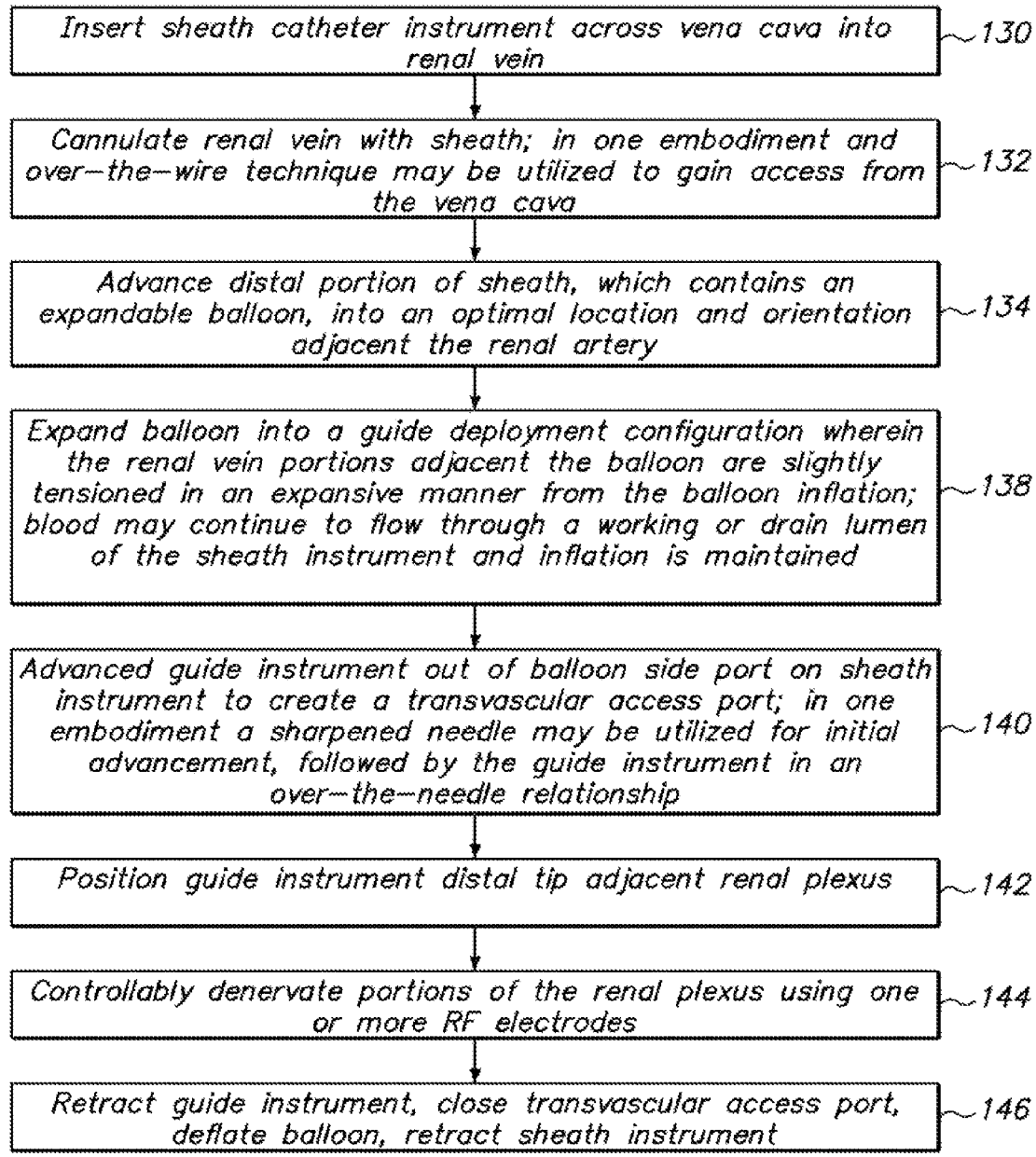
FIG. 12 illustrates various aspects of a trans-venous renal plexus denervation intervention wherein instrumentation is taken across a portion of a wall of the renal vein.

Referring to FIG. 12, a process for implementing a translumenal renal plexus denervation with a renal vein approach is illustrated. A sheath instrument is advanced up the vena cava and into the renal vein (130). An over the wire process may be utilized to gain full access to the renal vein for the distal portion of the sheath instrument (132). The distal portion of the sheath may be adjusted in position and orientation to optimize a translumenal approach toward the renal plexus (134). A balloon member coupled to the distal portion of the sheath member may be expanded to slightly tension the celiac trunk portions adjacent the balloon member, and blood may continue to flow past the balloon member using a lumen formed through the balloon member (138). A guide instrument may be advanced out of a side port of the sheath instrument to create a transvascular access port (140). In one embodiment, a sharpened needle may be utilized for the initial advancement, followed by the guide instrument in an over the needle interfacing relationship. The distal portion of the guide instrument may be positioned adjacent the renal plexus (142), and one or more RF electrodes may be utilized to controllably denervate portions of the renal plexus (144). Subsequently the guide instrument may be retracted, the transvascular access port closed (for example, using one or more clip members as described above in reference to FIG. 5B), the sheath balloon member deflated, and the sheath instrument retracted to leave a complete closure (146).

Figure 14B:
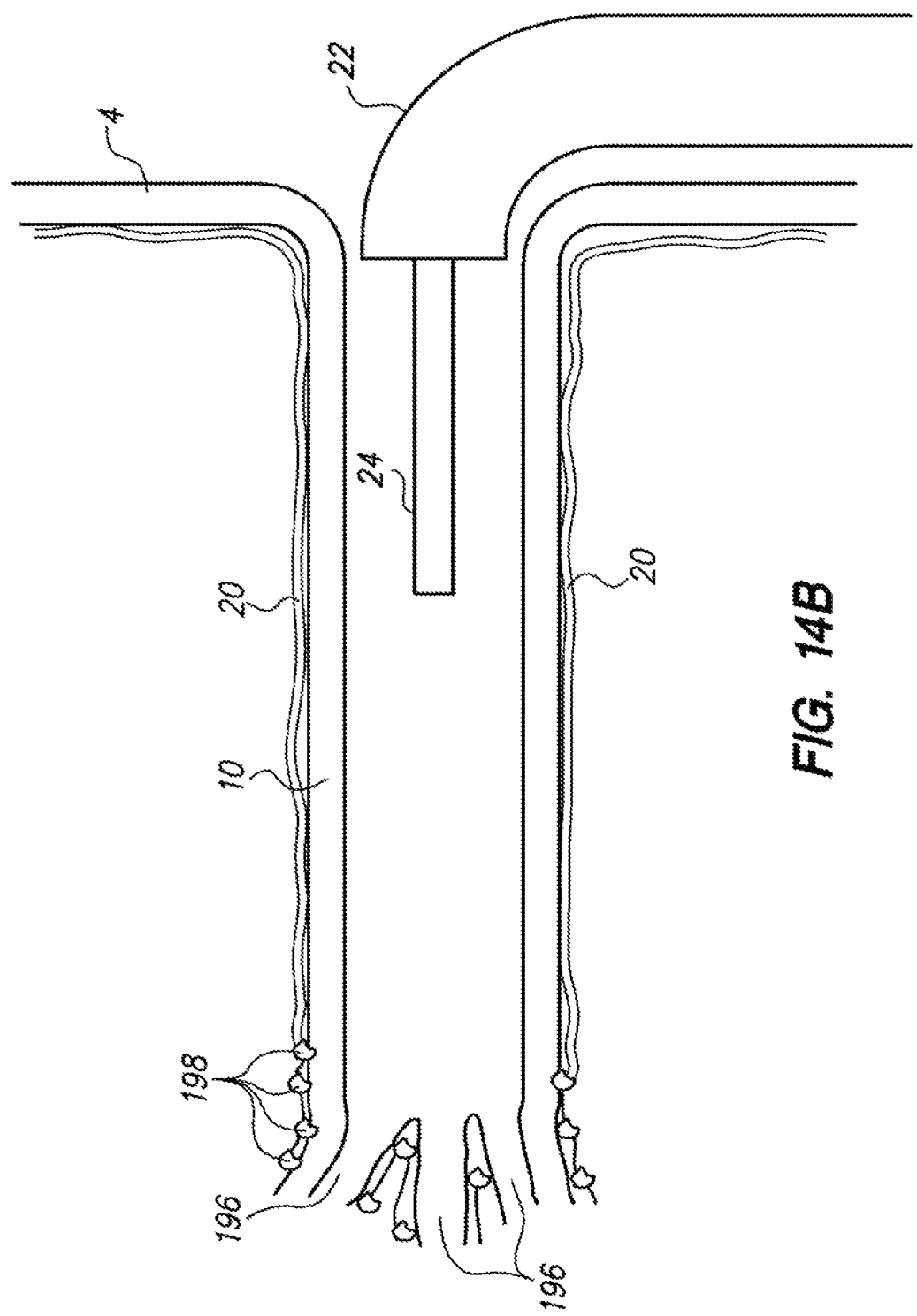
Figure 14C:
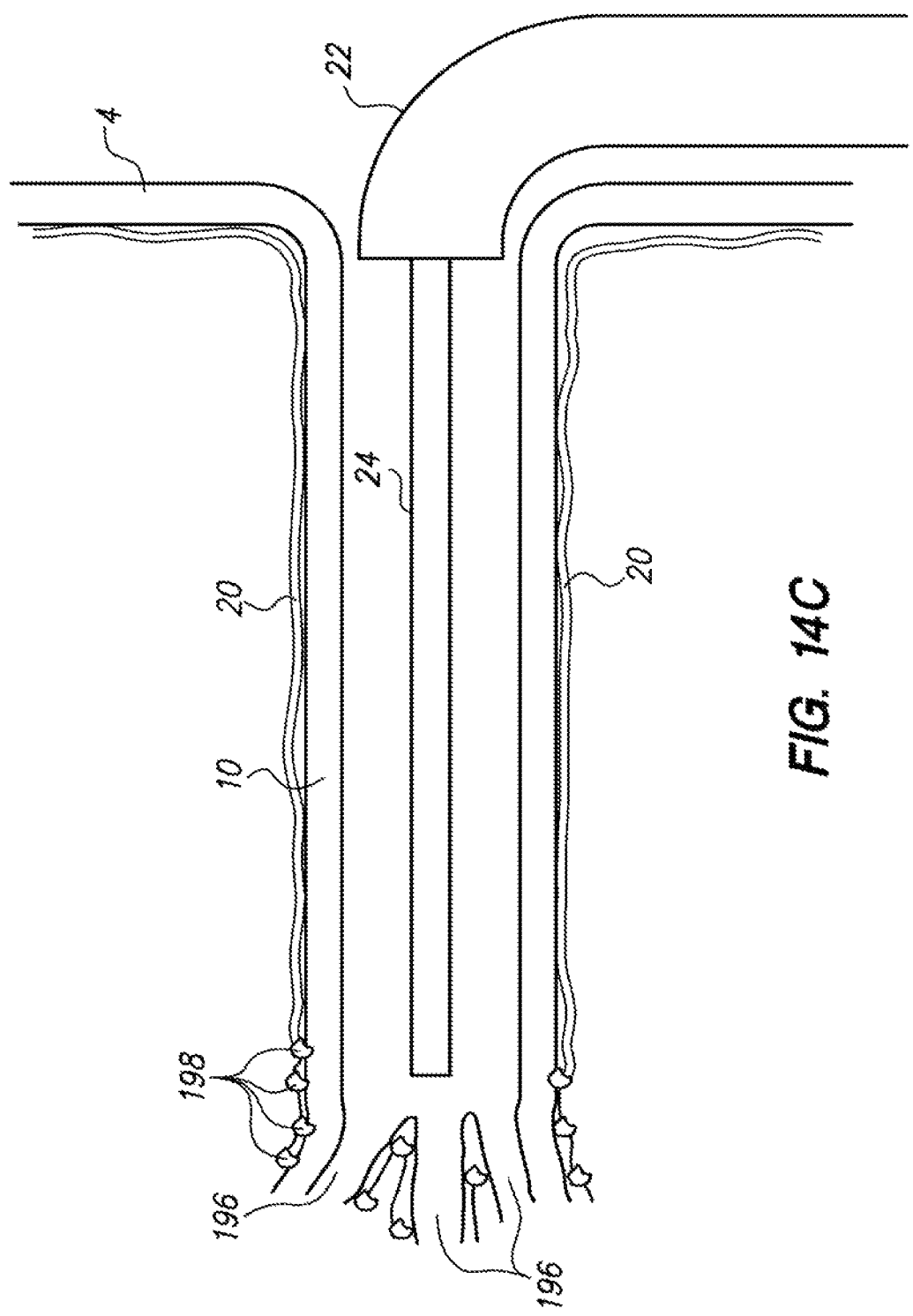

Referring to FIGS. 14A-14G, various aspects of configurations selected to controllably denervate portions of a renal plexus or fibers thereof are illustrated. As shown in FIG. 14A, a robotic sheath instrument (22) and guide instrument (24) assembly is depicted being advanced up the aorta (4) and into the renal artery (10). The coaxial slidable coupling of the two robotic instruments is useful in the depicted embodiment for telescoping the smaller instrument relative to the larger, as depicted in FIGS. 14B and 14C, for example. In another embodiment, a single robotic guide type instrument may be utilized without the load-shielding and related fine-control benefits of having a "home base" sheath structure (22) positioned at the aorta (4) as shown, for example, in FIGS. 14B and 14C. In another embodiment, a non-robotic sheath may be utilized along with a robotic guide instrument (24). In yet another embodiment, two non-robotic instruments may be utilized, such as steerable catheters or sheaths that are responsive to non-electromechanical pullwire or pushwire loading for steerability.

Referring again to FIG. 14A, several nerve tissue strands (20) are depicted surrounding portions of the renal artery (10), as are groups of juxtaglomerular apparatus (or "JGA") cells (198), which are known to be responsible, at least in part, for the production of renin in response to efferent neural signals through the fibers (20) of the renal plexus, and thereby correlated with increases in blood pressure. Also shown are several arterioles (196) where the renal artery (4) branches down to meet the kidney.

Referring to FIG. 14B, the larger sheath instrument (22) is positioned at the mouth of the renal artery (10) while the smaller guide instrument (24) preferably is electromechanically advanced, and navigated to avoid local tissue trauma. As described above in reference to FIGS. 5A-5D, the distal portion of the guide instrument (24) may be equipped with various sensors (i.e., such as ultrasound transducers, localization sensors, thermocouples, and/or radiation antennae such as microwave antennae for blackbody radiation sensing) and/or treatment elements (i.e., such as high intensity focused ultrasound transducers, RF electrodes, laser emission elements, fluid emission elements, and the like). Referring to FIG. 14C, further insertion of the guide instrument (24) into the renal artery is facilitated by the electromechanical control of a robotic catheter system, the navigation of which may be facilitated by imaging modalities such as transcutaneous ultrasound, transvascular ultrasound, intravascular ultrasound, fluoroscopy, and navigation within a registered three-dimensional virtual environment created using images from modalities such as computed tomography, 3-dimensional computed tomography, magnetic resonance, X-ray, fluoroscopy, and the like, as described, for example, in the aforementioned incorporated references. For example, in one embodiment, a "no touch" insertion may be accomplished utilizing the stability provided by the placement of the sheath instrument (22), along with the navigability of a registered and real-time (or near real-time) imaged robotically steerable guide instrument (24).

Figure 14D:
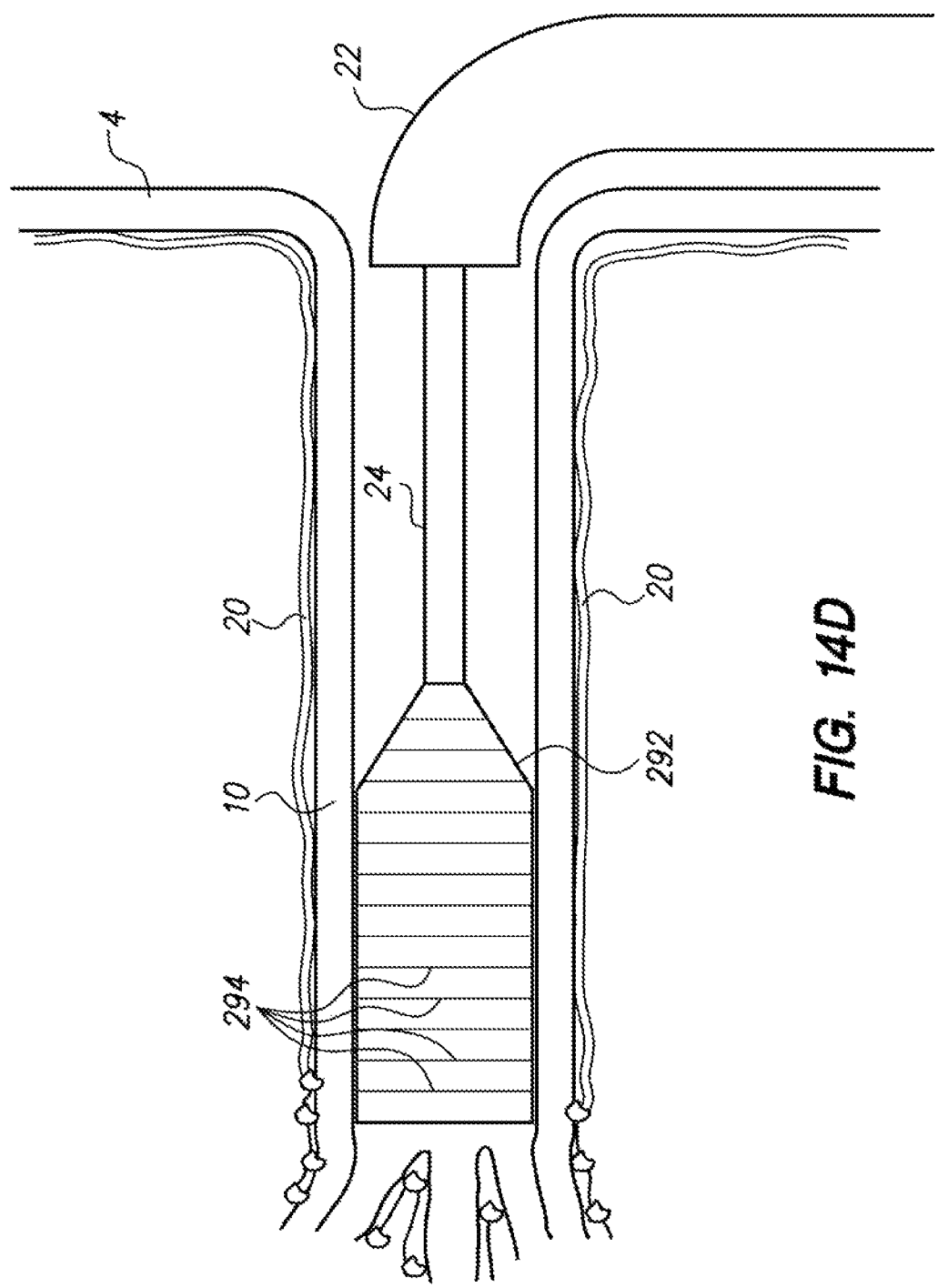

Referring to FIG. 14D, subsequent to cannulation of the renal artery (10) to a position approximately adjacent the renal arterioles (196), a brief mapping study or investigation may be executed. This mapping study may be preceded by preoperative or intraoperative imaging to determine at least some information regarding the positions, or likely positions, of aspects of the renal plexus. Referring again to FIG. 14D, in one embodiment, a flexible, expandable device (292), such as a controllably expandable balloon or stentlike structure, may be controllably deployed from the guide instrument (24) and expanded to provide a direct interface between the tissues of the subject lumen and circuit elements (294) of the expandable device (292), the circuit elements being configured to detect nearby electrical signals, and in one embodiment to be alternatively be utilized to treat the nearby tissues through the controllable flow of current therethrough. In one embodiment, a conformal electronics polymer material, such as that available under the tradename MC10® by MC10 Corporation of Cambridge, Mass., may be utilized to embed radiofrequency ("RF") or other electrode circuitry within an inflatable or expandable substrate, as depicted in FIGS. 14D and 14E. Referring to the close up view of FIG. 14F, the circuit elements (294) may have sharpened probing portions (296) configured to protrude into nearby tissues, such as the walls of the renal artery (4), to gain closer proximity to signals passing through nearby neural structures, such as the depicted renal plexus fibers (20), and/or to gain closer proximity to structures to be denervated or altered in a treatment phase, such as by applying RF energy for selective denervation by heating. Full inflation or expansion of the associated expandable device (292) may be required to seat the probing portions (296) across portions of the nearby tissue structures, and the assembly of the expandable device (292), circuit elements (294), and probing portions (296) preferably is configured to be retractable back into the delivery instrument (24) without damage to nearby structures. In the embodiment depicted in FIGS. 14D-14F, deflation or controlled outer geometry shrinking of the expandable device (292), concomitant with incremental insertion of the guide instrument (24) and slight refraction of the expandable device (292), may be utilized to safely retract the expandable device after mapping and/or treatment.

Figure 14G:
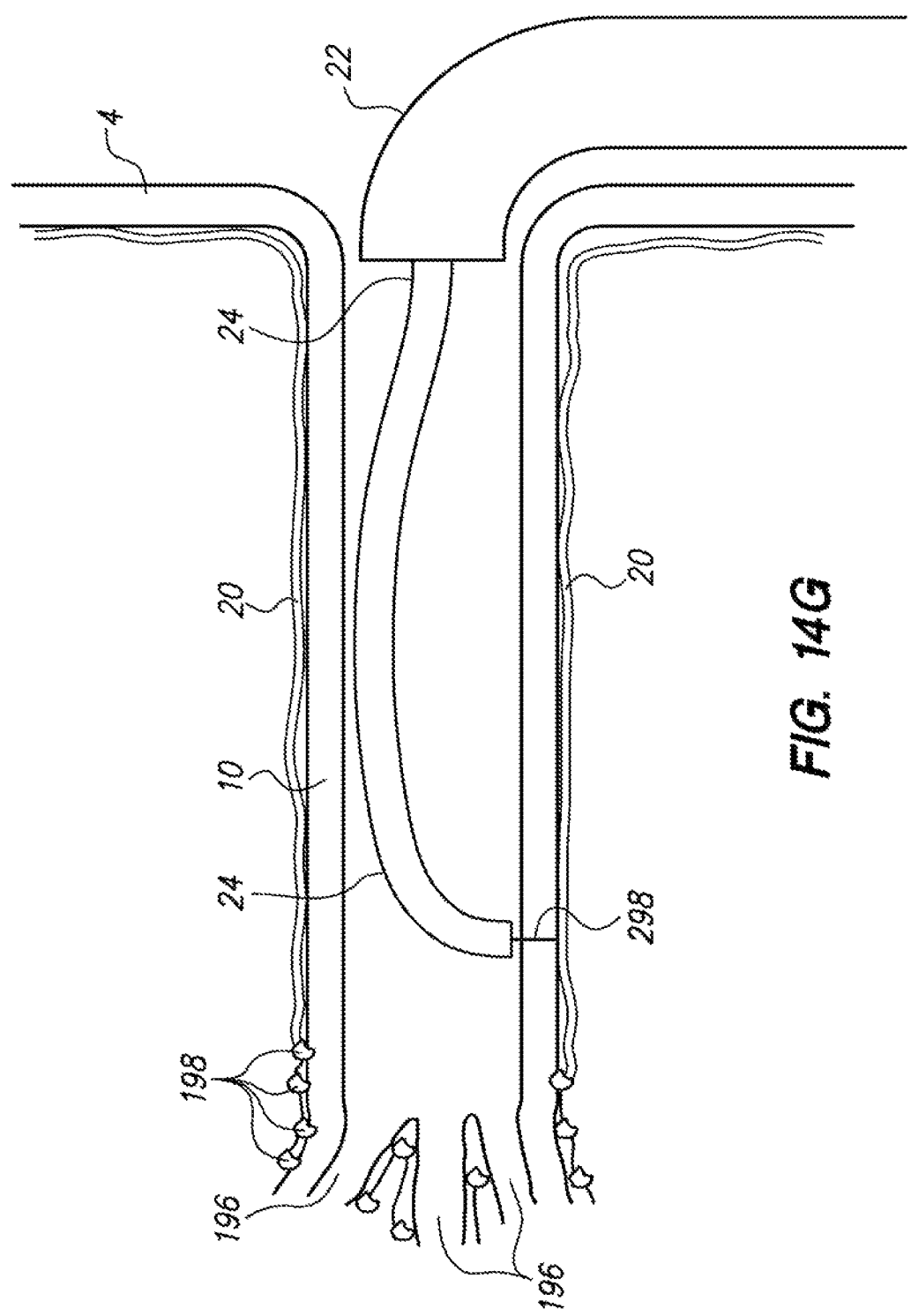

Referring to FIG. 14G, in another embodiment, an individual probe member (298), such as an RF needle tip, may be utilized to selectively probe pertinent tissue structures for both mapping and treatment steps. Preferably the controller of the robotic catheter system is configured to not only controllably navigate the probe member (298) to locations of interest with a desirable insertion vector and insertion location, but also to store trajectory, path, location, and other information pertinent to each diagnostic and/or treatment step for constant monitoring of the procedure, and also ease of repeatability—or ease of avoiding repeatability (i.e., in scenarios wherein it is not desirable to conduct two RF heating bouts on the same tiny volume of tissue).

Figure 14H:
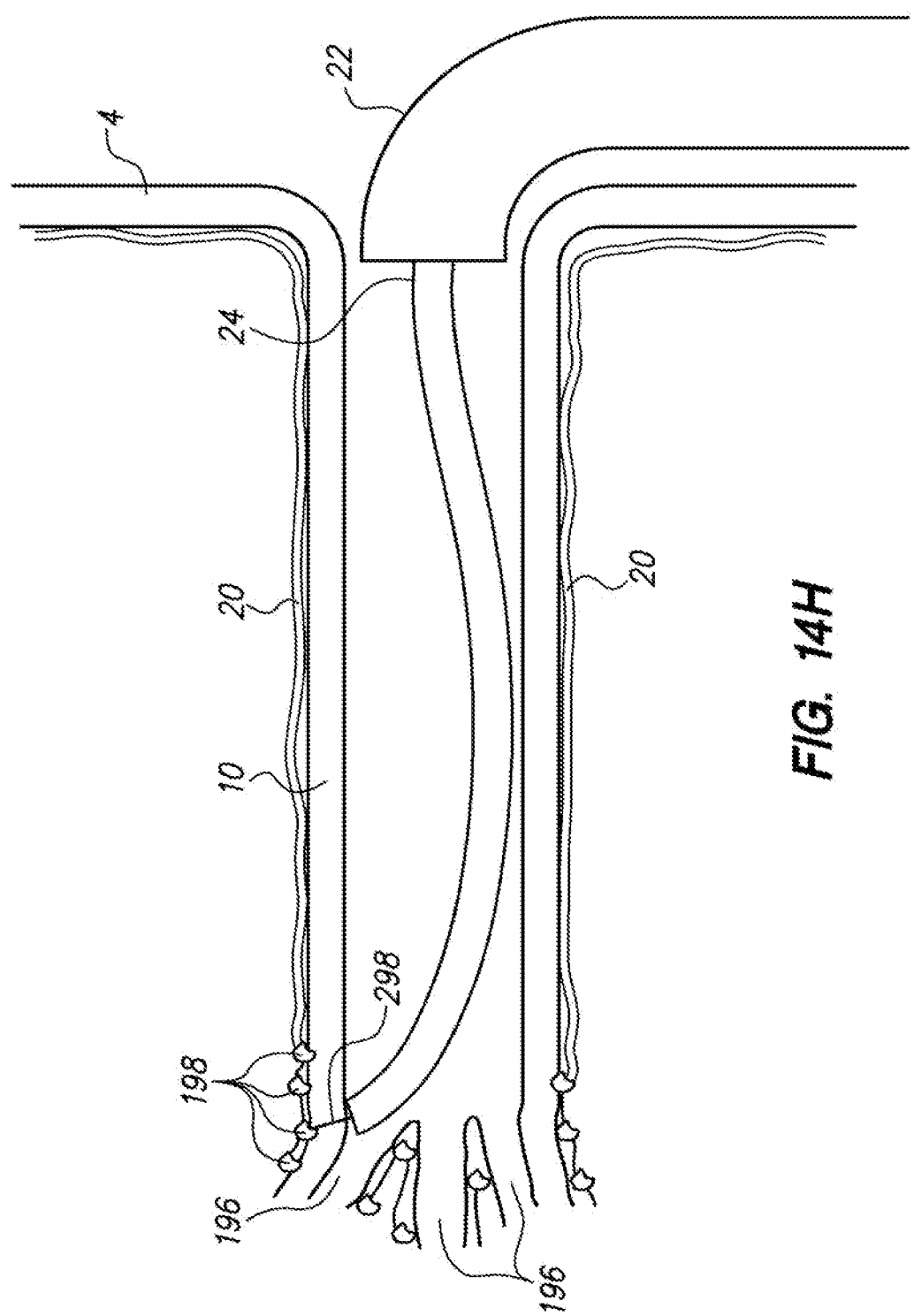

Referring to FIG. 14H, in one embodiment, a probe member (298) may be navigated directly to discrete JGA cells (198) or lesions of JGA cells to selectively destroy these directly. Any of the embodiments described herein may incorporate load sensing capabilities of the subject robotic catheter system, along with haptic input device features, to facilitate fine, atraumatic, predictable navigation of the diagnostic and/or treatment tools.

Figure 15A:
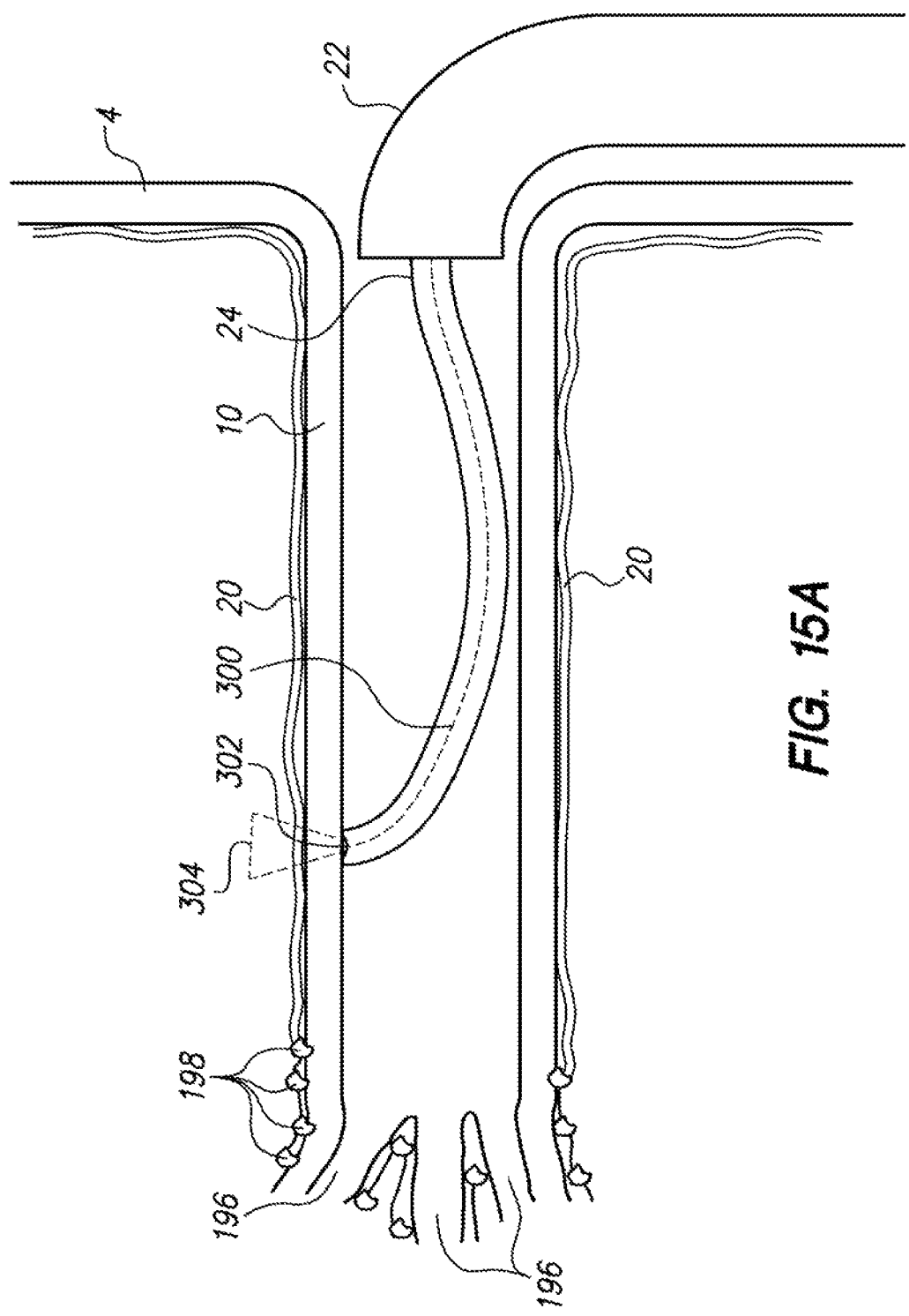
Figure 15B:
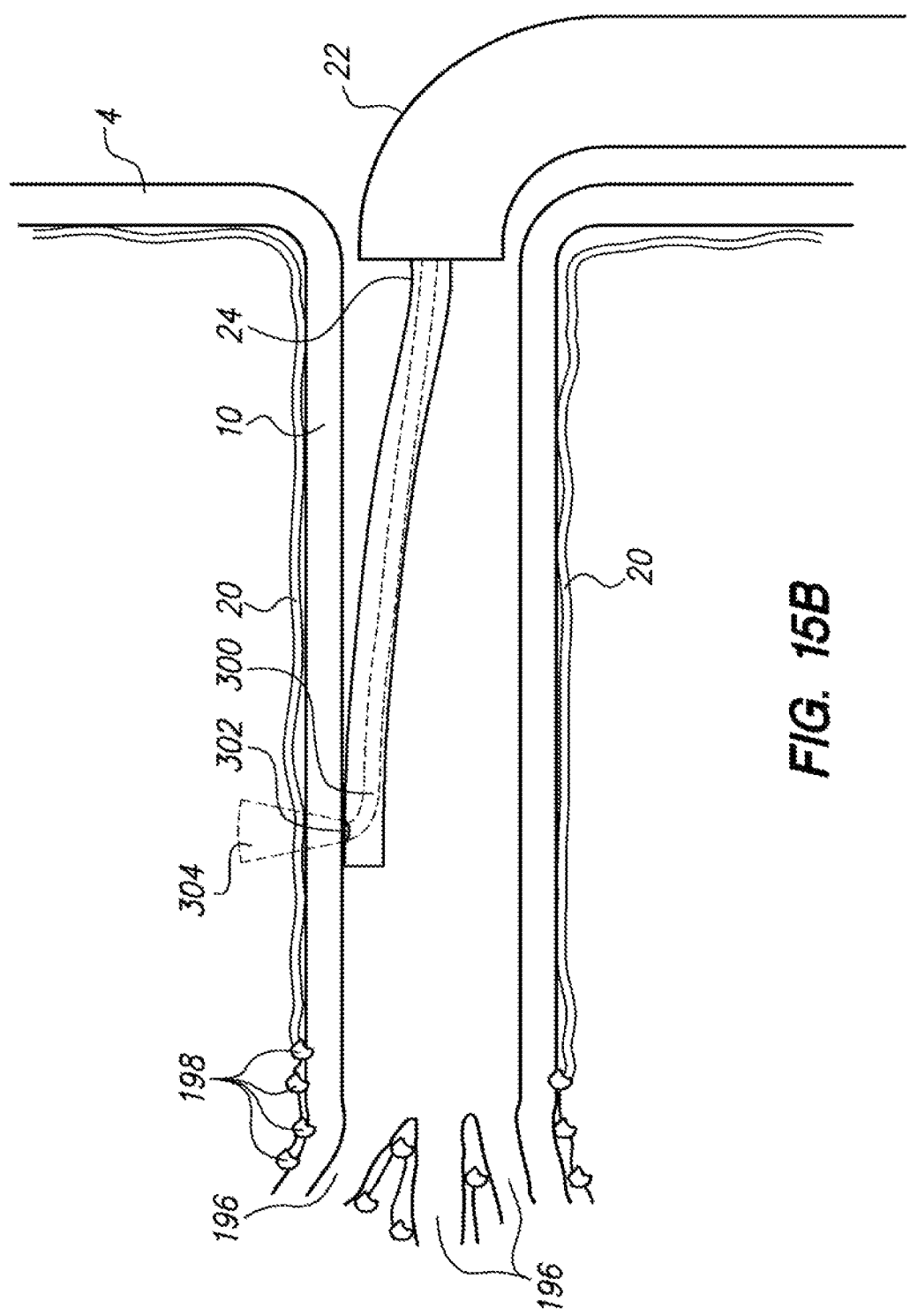

Referring to FIG. 15A, in another embodiment, an optical coherence tomography (or "OCT") fiber (300) may be coupled between a distal lens (302) and a proximal emitter/interferometer (not shown; available from sources such as ThorLabs, Inc., of Newton, N.J.) to facilitate OCT tissue structure threshold sensing (i.e., the sensing and/or visualization of boundaries of nearby tissue structures, such as the renal artery (10) wall thresholds, nerve fiber 20 structure thresholds, and the like) with a virtual field of view (304) dependent upon the lens (302) and emissions parameters. Such OCT imaging analysis may be utilized not only to locate structures of interest, but also to treat such structures—with near-real-time analysis of not only the tissue structure thresholds, but also thresholds of other objects, such as RF electrode probe tips and the like. The embodiment of FIG. 15A features an OCT configuration wherein the lens (302) is located on a distal face of the guide instrument (24). Referring to FIG. 15B, an arcuate configuration of the OCT fiber (300) proximal to the side-oriented lens (302) and field of view (304) may be utilized for a side-capturing configuration. Referring to FIG. 15C, another side-capturing configuration is facilitated by a mirror or reflector (306) configured to reflect outgoing and incoming light signals as shown.

Figure 15D:
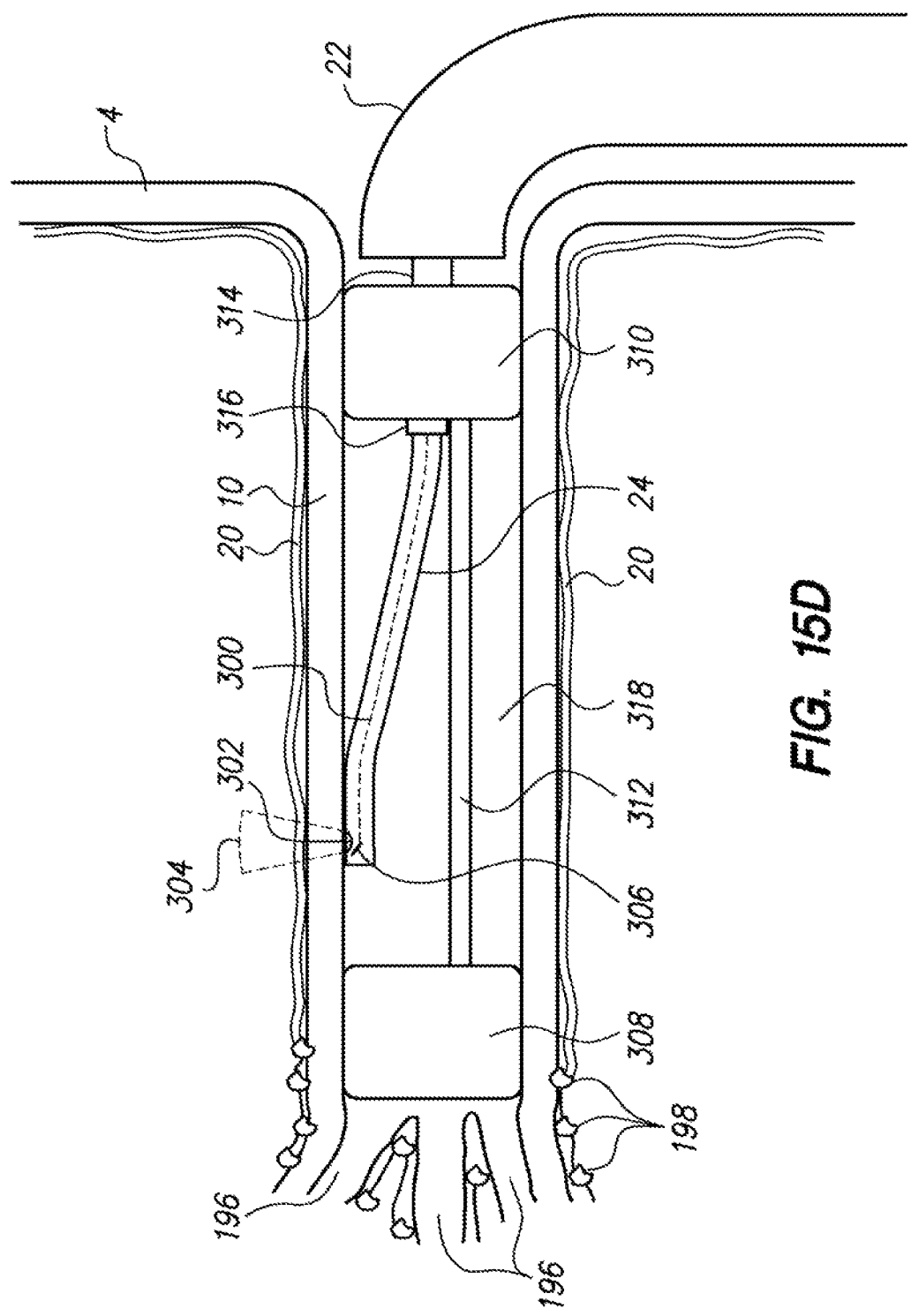

Referring to FIG. 15D, an embodiment is shown wherein a working volume (318) is evacuated of blood to facilitate greater flexibility with light-based imaging technologies, such as video and OCT. In other words, the embodiments of FIGS. 15A-15C showed the lens (302) purposefully in almost direct opposition to nearby tissue structures, to avoid scattering and other effects of red blood cells and other elements of flowing blood which may negatively impact such imaging. The embodiment of FIG. 15D addresses this concern by temporarily (i.e., for a short period of time, as dictated by the pathophysiology of the associated kidney and other tissue structures) evacuating the working volume (318) of blood. This is accomplished in the depicted embodiment by inflating two expandable occlusive elements (308, 310), such as balloons, and evacuating the captured blood using simple vacuum proximally through the sheath (22) and associated instruments. A larger delivery member (314) accommodates coupling of the guide instrument (24) and also the volume capture assembly, which comprises the two expandable occlusive elements (308, 310) and a coupling member (312). A guide instrument port (316) allows for slidable coupling of the proximal expandable occlusive element (310) and the guide instrument (24). With such a configuration, various imaging devices may be utilized to create images of nearby anatomy, such as ultrasound (in which case a transmissive medium, such as saline, may be pumped into the working volume for sound wave transmission enhancement and subsequently removed), CCD cameras, CMOS cameras, fiberscopes, and the like, in addition to the aforementioned imaging configurations such as OCT.

Figure 16:
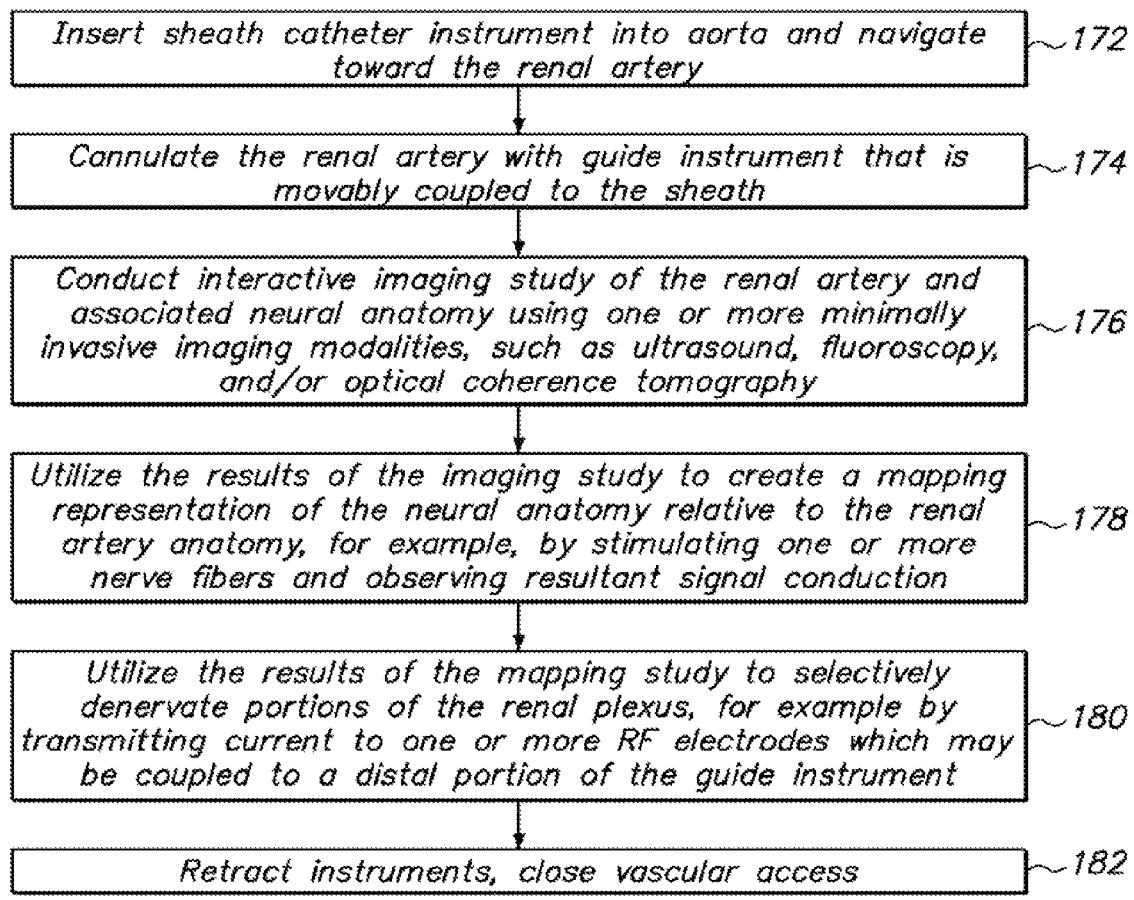
FIGS. 16-21 illustrate process embodiments in accordance with the present invention.

Referring to FIGS. 16-21, various process embodiments are illustrated wherein one or more minimally invasive instruments may be utilized in diagnostic and/or interventional medical procedures. Referring to FIG. 16, after a remotely steerable sheath catheter instrument is inserted into the aorta and navigated toward the renal artery (175), the renal artery may be cannulated, for example with a coaxially associated remotely steerable guide instrument that is movably coupled to the sheath instrument (174). An interactive imaging study, or steps thereof, may be conducted of the renal artery and associated neural anatomy using one or more minimally invasive imaging modalities, such as ultrasound, fluoroscopy, and/or OCT (176), as described above. The results of the imaging study may be utilized to create a mapping representation of the neural anatomy relative to the renal artery anatomy, for example, by stimulating one or more of the associated nerve fibers and observing resulting signal conduction (178). In other words, referring back to FIGS. 14E and 14F, in one embodiment, one or more of the proximal (i.e., closer to the aorta in the variation of FIG. 14E) circuit elements and/or associated probing portions (element 296 of FIG. 14F) may be used to stimulate or electrify adjacent nerve fiber (20) portions at such proximal position, and the conduction of such stimulation may be detected with each of the other circuit elements (294) to monitor or "map" the associated conduction pathways. The results of such mapping may be utilized in the selective denervation of portions of the renal plexus, for example, by transmitting current to heat and denervate such portions (180). The mapping configuration may then be utilized to confirm that the denervation was, indeed, successful, or to what extent, with further stimulation of the pertinent fibers and monitoring of the results. Further, renin levels, such as in the renal vein, may be monitored to determine a level of treatment success associated with the thermal denervation treatment. Similarly, alcohol and other fluids may be utilized and monitored for denervation. Ultimately, the pertinent instruments may be retracted and the vascular access closed (182).

Figure 17:
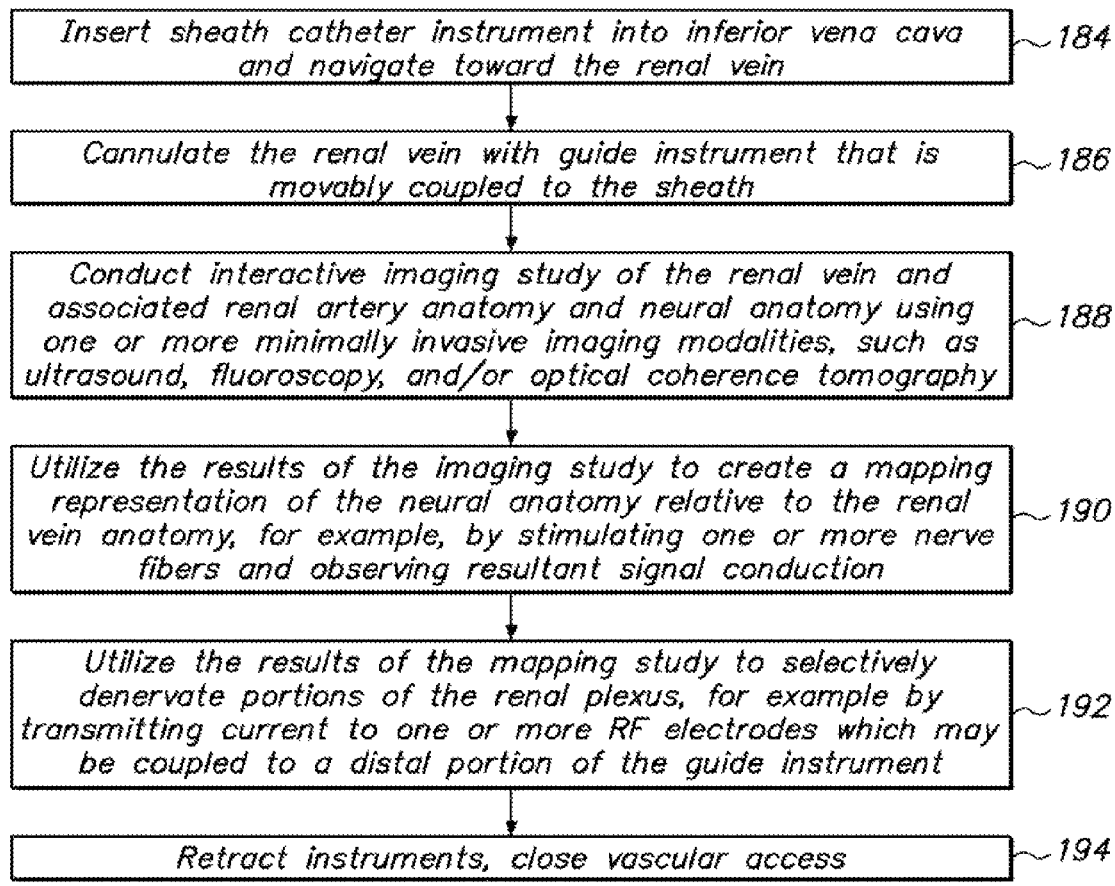

Referring to FIG. 17, a process similar to that of FIG. 16 is depicted, with the exception that a venous route is utilized to conduct denervation near the renal artery. This is believed to be less clinically complicated in certain scenarios. The catheter instrumentation is inserted into the inferior vena cava and navigated toward the renal vein (184). The renal vein is cannulated with a guide instrument movably coupled to the sheath instrument (186). The imaging study is conducted not only on the neural anatomy, but also on the renal vein anatomy and renal artery anatomy to understand the relationships of these three and other nearby tissue structures (188). The results of the imaging study may be utilized as inputs in a mapping subprocess, wherein one or more nerve fibers may be stimulated and the resulting signal conduction observed (190). The neural anatomy map resulting from the mapping efforts may be utilized for selective denervation treatment of the renal plexus (192), as well as in generating feedback to an operator regarding the effectiveness of various denervation attempts (as described above, renin levels also may be monitored). Subsequently the instruments may be retracted and the vascular access closed (194).

Figure 18:
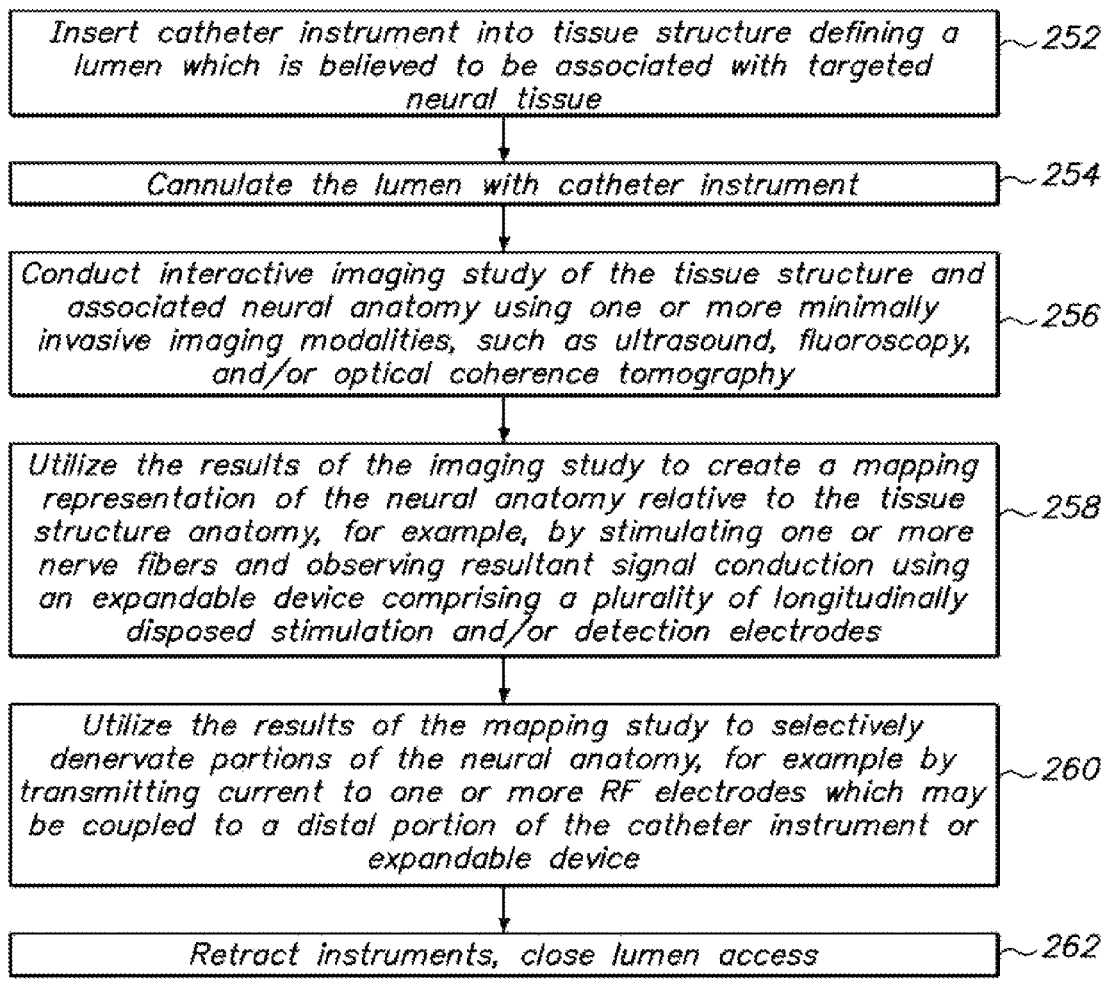

The embodiment of FIG. 18 illustrates that process configurations such as those described above in reference to FIGS. 16 and 17 may be broadly applied to many tissue structures that define one or more lumens through which the pertinent instrumentation may be advanced and utilized. Referring to FIG. 18, a catheter instrument may be inserted into the tissue structure defining a lumen believed to be associated with targeted neural tissue (252). The lumen may be cannulated with the catheter instrument (254). An interactive imaging study may be conducted to create an image-based anatomic mapping representation of the neural anatomy and other pertinent tissue structures (256), and an expandable device such as that described in reference to FIGS. 14E and 14F may be utilized to observe signal conduction (258) and create an electrical mapping which may be utilized to monitor the effectiveness of the treatment steps (260). Subsequently the instrumentation may be removed and access to the pertinent lumens and/or tissue structures discontinued (262).

Figure 19:
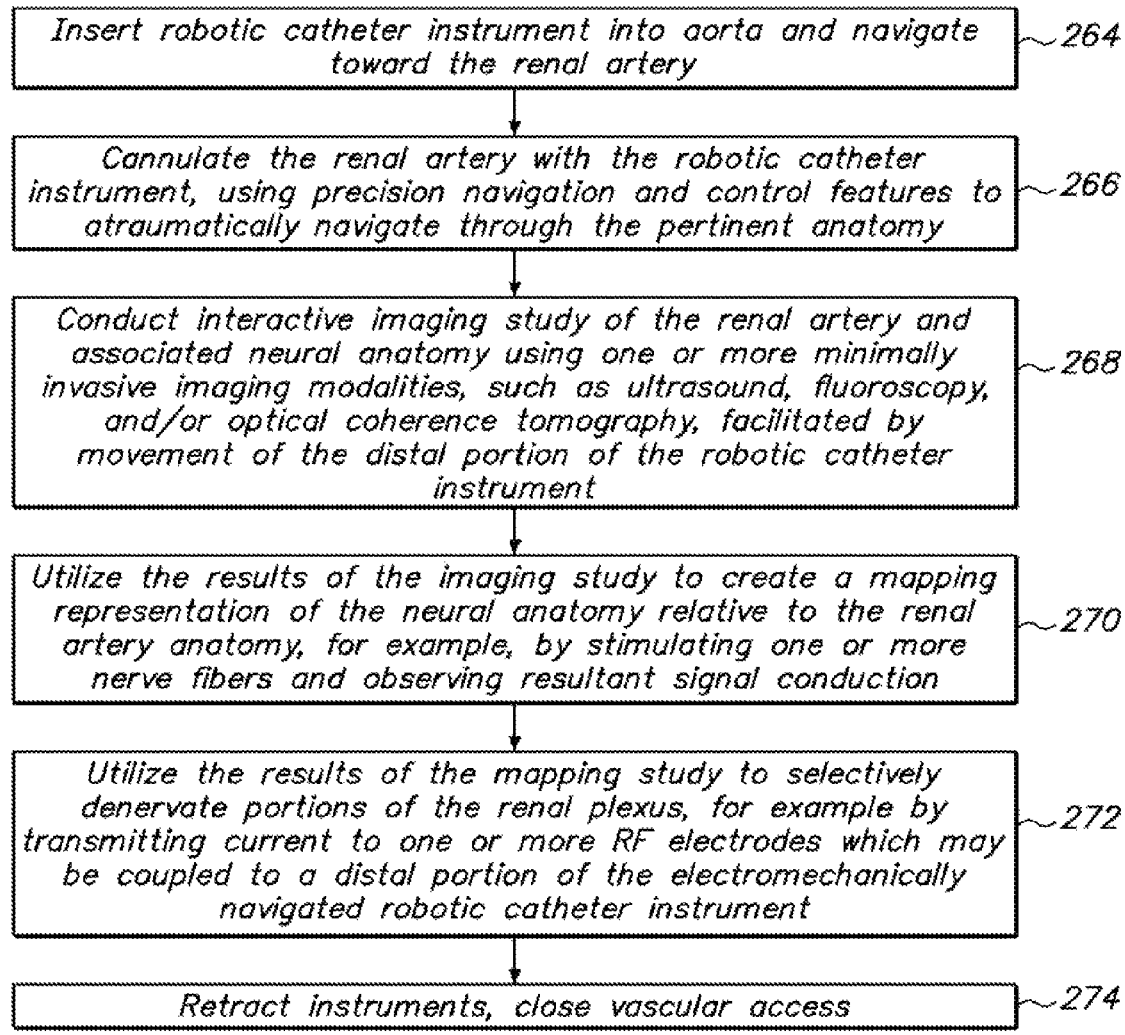
Figure 21:
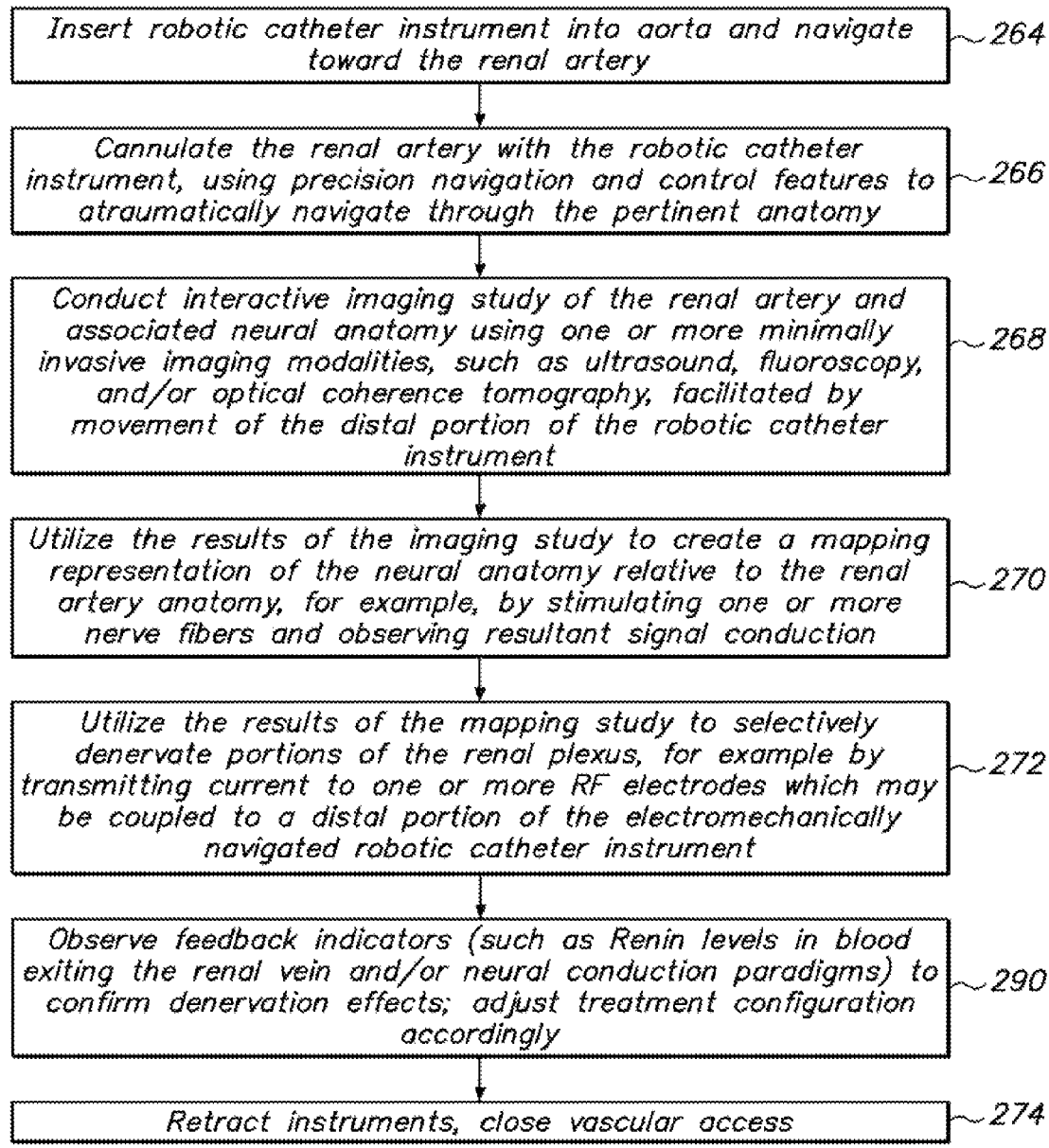

FIG. 19 illustrates aspects of an embodiment wherein a robotically-steerable catheter instrument specifically is utilized (as described above, the aforementioned catheter instruments may or may not be remotely electromechanically navigable). With the robotic catheter instrumentation inserted into the pertinent lumen, such as an aorta in this example (264), precision navigation and control features of the robotic instrument may be utilized during the insertional navigation (266), anatomic imaging may be conducted (268), electrical mapping may be conducted (270), and selective denervation may be conducted (272), followed by removal of the pertinent instrumentation and closure of the vascular access (274). FIG. 21 illustrates a related embodiment with the additional step depicted (290) of observing feedback indicators, such as renin levels in blood exiting the renal vein and/or neural conduction paradigms with the mapping configuration, as confirming techniques for monitoring and/or adjusting treatment in a closed loop type of configuration.

Figure 20:
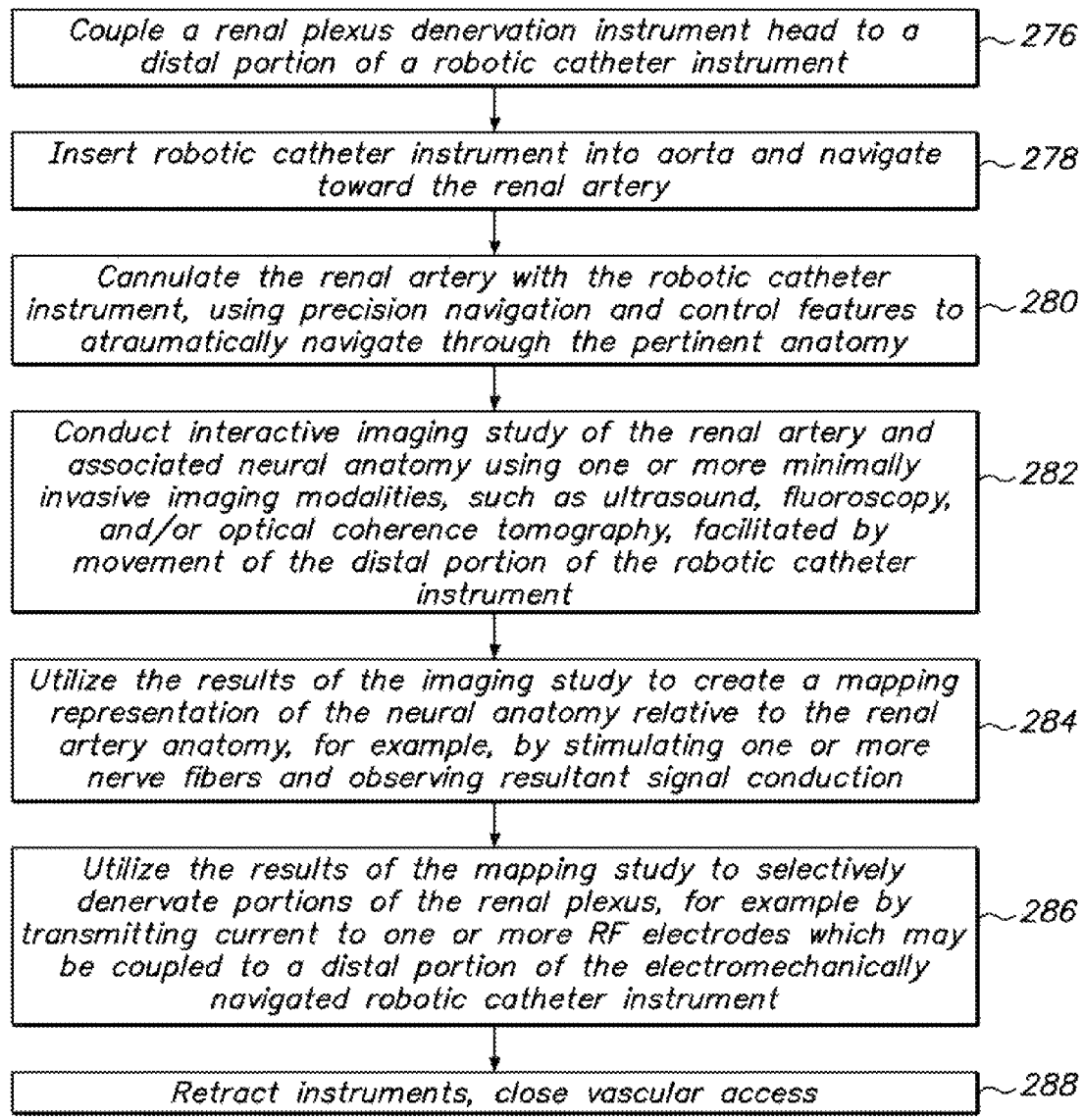

Referring to FIG. 20, a robotic catheter system such as that described and incorporated above may be utilized to operate an off-the-shelf treatment head such those available on instruments from the Ardian division of Medtronic Corporation, to improve the navigability of such treatment head, and combine the treatment capabilities of such treatment head with additional diagnostic and treatment capabilities, such those described herein. As shown in FIG. 20, after a renal plexus denervation treatment head has been coupled to a distal portion of a robotic catheter instrument (276), the instrument may be inserted into an aorta or other lumen and navigated toward the renal artery or other targeted tissue structure (278). In the depicted renal intervention embodiment, the renal artery may be cannulated using the navigation control of the robotic instrumentation (280), after which an anatomic imaging study may be conducted (282), an electrical mapping study conducted (284), selective denervation attempted with feedback from the mapping configuration (286), and subsequent removal of the instruments and closure of the access (288).

Referring to FIG. 22, in another embodiment, a configuration similar to that depicted in FIG. 14G is depicted, and in the embodiment of FIG. 14G, is being operated to create a pattern of treatments (200) that is substantially elliptical, and that is configured to reduce the chances of post-intervention stenosis or other complications, due to the fact that the treatment contacts forming the pattern are spread over a larger length, longitudinally, of the targeted tissue structure (here a renal artery 10). Other patterns may be created within the defined lumen space, such as sets of curves, portions of circumferential lines, and the like.

Figure 23A:
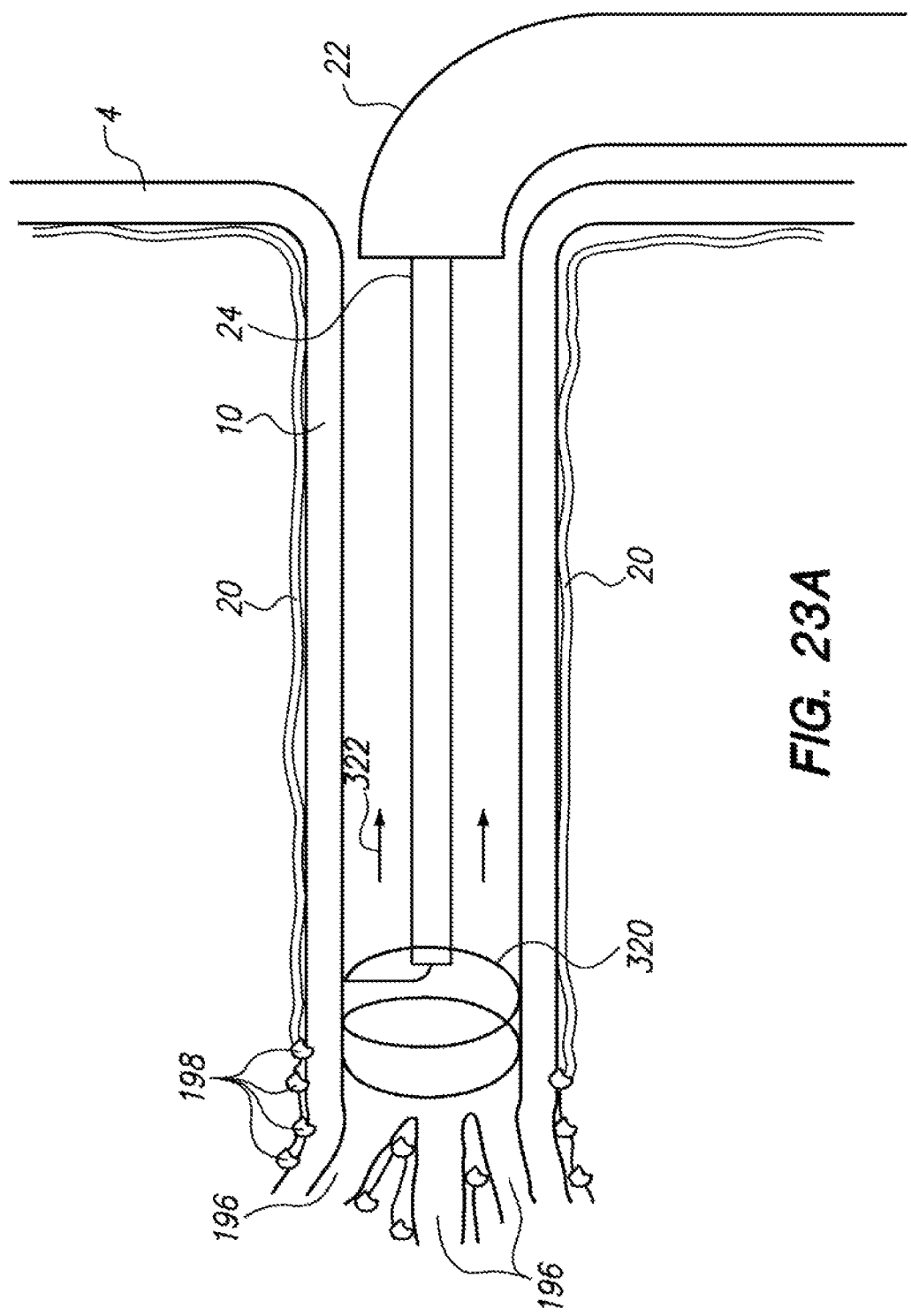
Figure 23C:
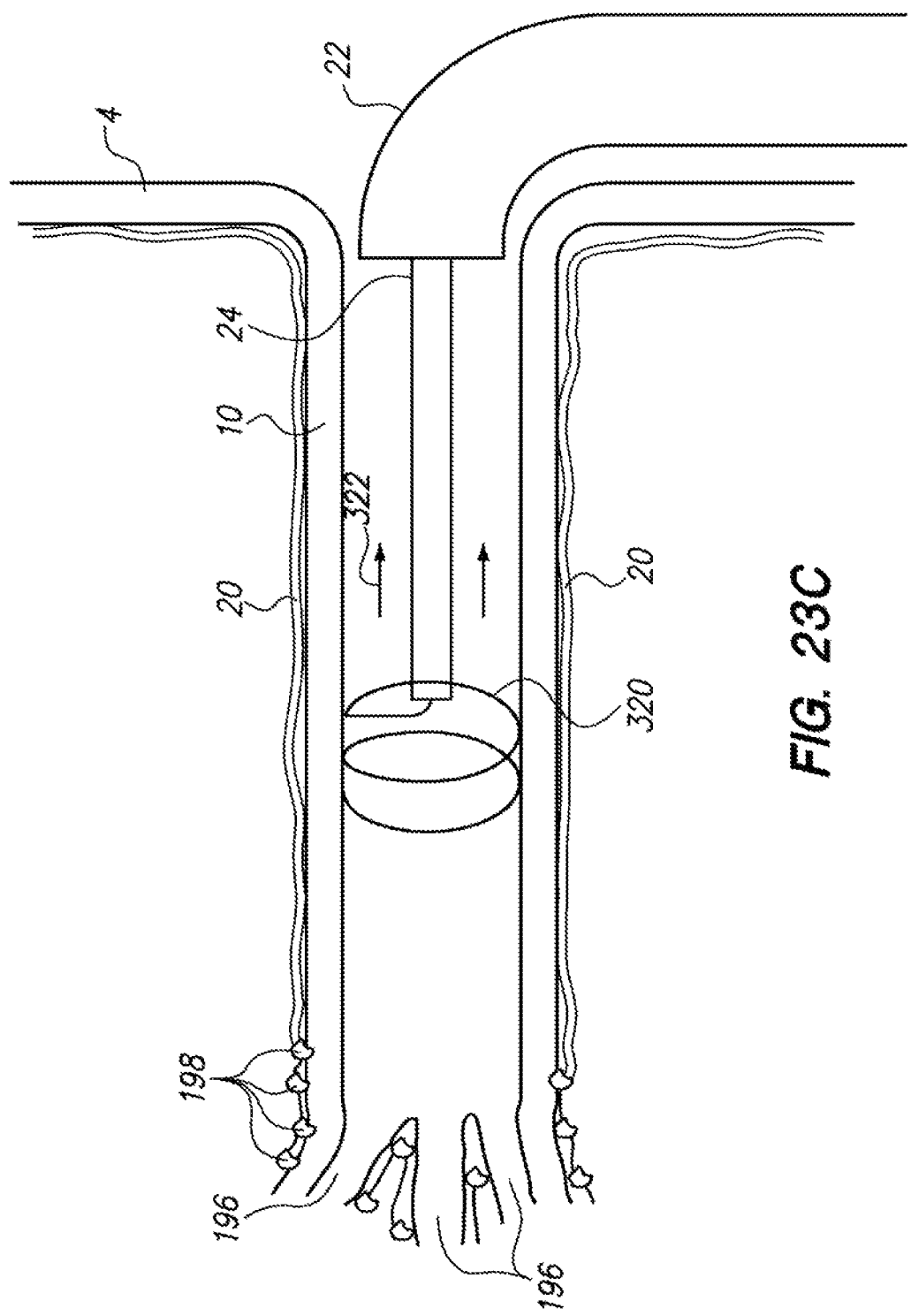

Referring to FIGS. 23A-23C, a configuration is illustrated wherein a substantially helical treatment element (320) configured to conform to the targeted lumen (here a renal artery 10 lumen) may be pushed out the distal end of the delivery system (here a robotic sheath instrument 24), and then pulled back (322) proximally as the instrument (24) is withdrawn proximally, creating an opportunity to cause RF electrodes or other treatment elements coupled to the helical member (320) to create a longitudinal lesion configured to denervate targeted nerve fibers (20) which may be disposed about the targeted lumen. The treatment elements coupled to the helical member (320) may be configured or operated to remain in an "on" mode (i.e., treatment inducing; such as current flow mode with RF electrode treatment elements) during pullback (322), or may be configured to switch on and off intermittently with various patterns over time, such patterns being pre-programmable. FIGS. 23B and 23C illustrate further pullback (322) of the treatment assembly (24, 320), which may be automated using an "autoretract" functionality of the robotic guide/sheath catheter systems, descriptions of which are incorporated by reference herein.

Figure 24:
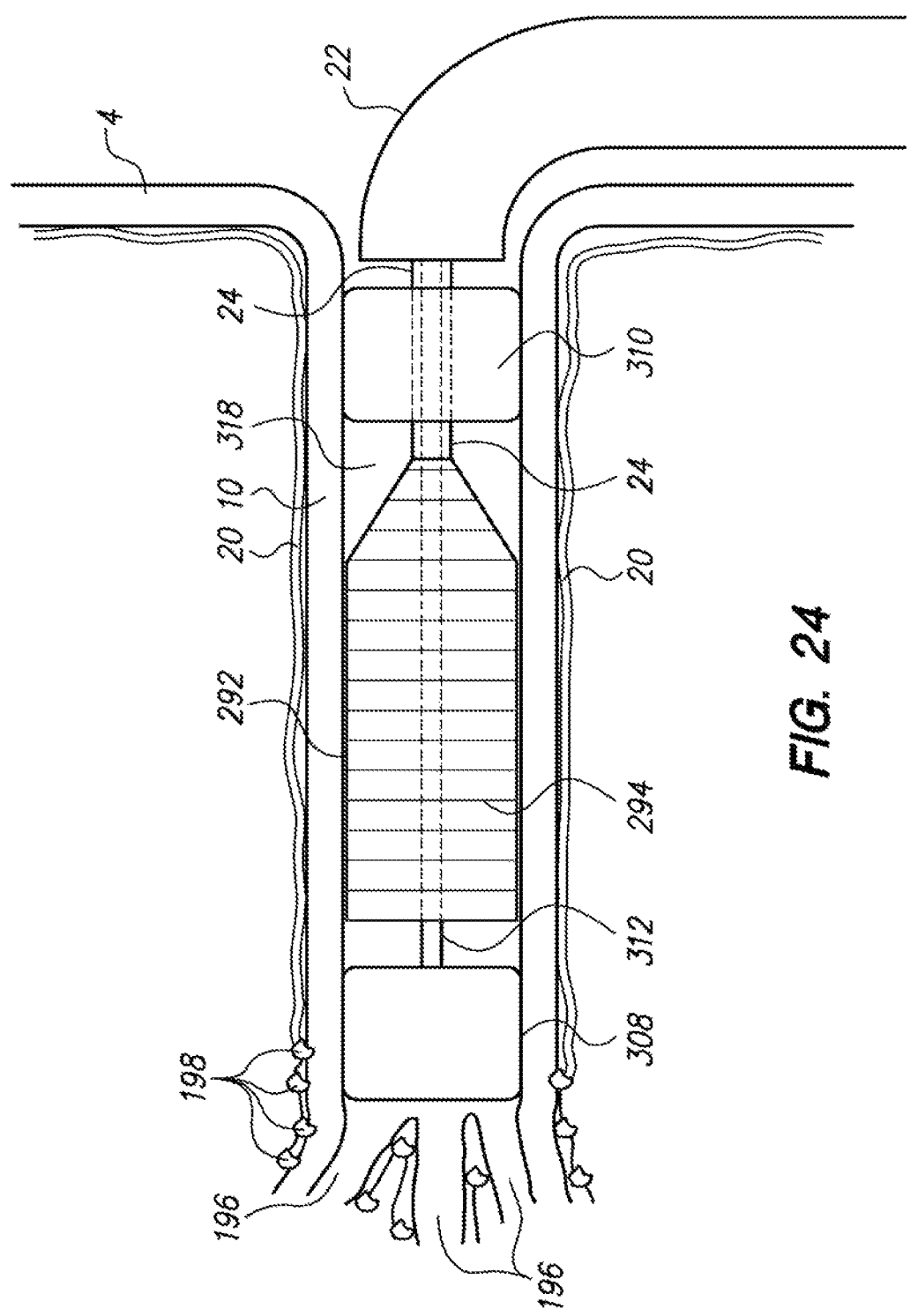
FIG. 24 illustrates an embodiment wherein an evacuated volume may be utilized to assist with a denervation treatment wherein an expandable device comprising one of more circuit elements is utilized in a denervation treatment.

Referring to FIG. 24, a set of expandable members (308, 310, such as a set of two balloons) may be used to isolate the nearby treatment environment for a diagnostic/treatment configuration (292, 294) such as that depicted in FIGS. 14D-14F. As shown in FIG. 24, a distal expandable balloon member (308), coupled to a proximal expandable balloon member (310) by a coupling member (312) that preferably defines an inflation lumen for the distal expandable balloon member (310), may be inserted in a collapsed form (not shown) through a lumen defined through the guide instrument (24), expanded (as illustrated), and utilized to vacuum away blood captured in the capture volume (318) for diagnostic and/or treatment steps. With the capture volume isolated, carbon dioxide or other bioinert gases, or saline, may be infused through an infusion lumen fluidly coupled to the capture volume (318) through one or more of the elongate proximal instruments (24, 22, 312) to facilitate diagnostic and/or treatment steps, such as improved tissue apposition, improved electrical conduction, and/or improved imaging and/or visualization, such as direct visualization using an associated fiber imaging bundle or imaging chip configured to have a field of view within or adjacent to the capture volume, or an ultrasound or OCT imaging configuration as described above.

Figure 25A:
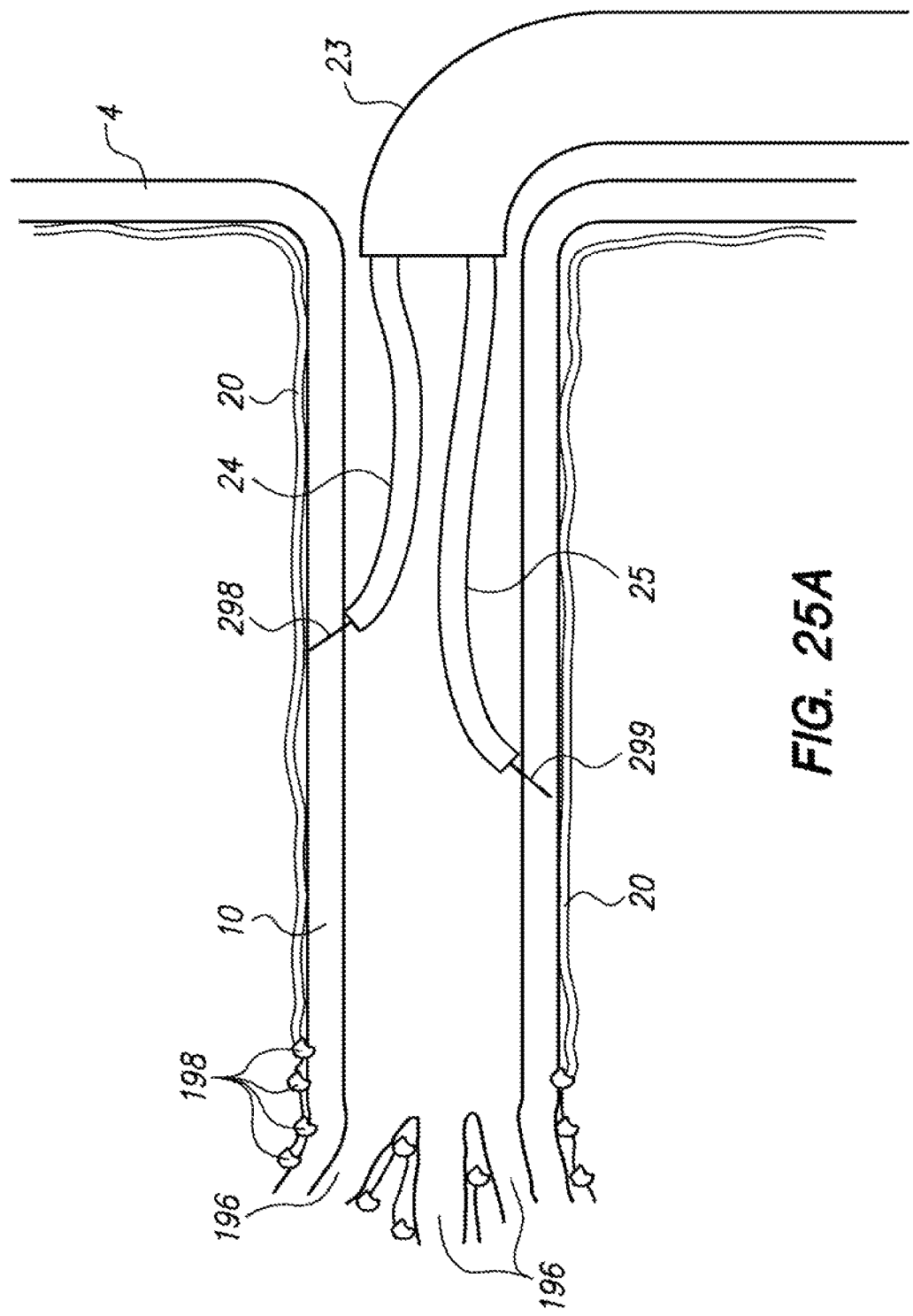
FIGS. 25A and 25B illustrate embodiments wherein two or more guide instrument assemblies may be utilized to conduct a denervation treatment.
Figure 25B:
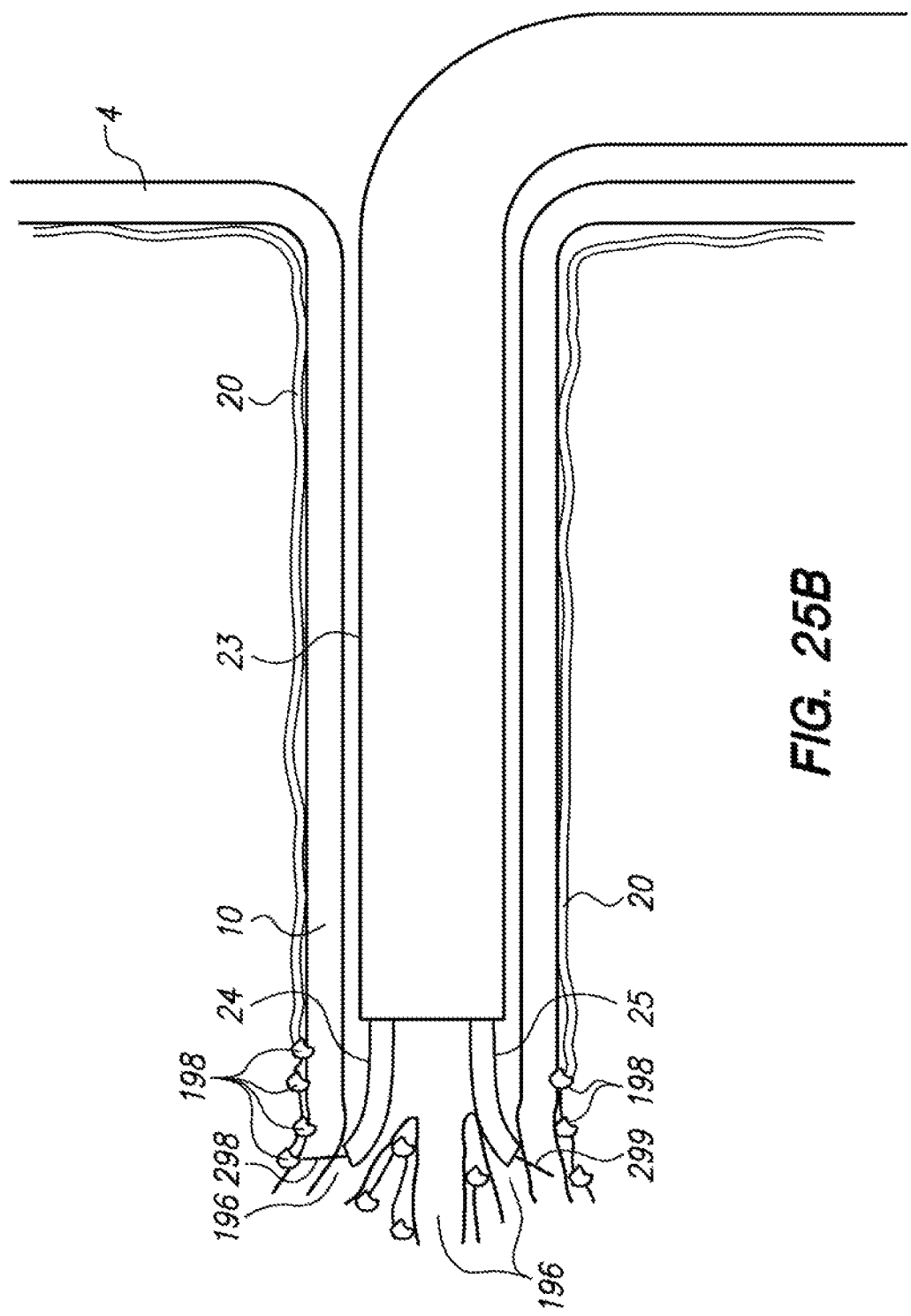

Referring to FIGS. 25A and 25B, in another embodiment, two or more elongate steerable instruments (24, 25) may be utilized simultaneously from the same sheath instrument (23) configured to host and stabilize both guide instruments (24, 25) and advance a plurality of diagnostic and/or interventional probe members (298, 299). Such a sheath/guide configuration is described in the aforementioned incorporated by reference disclosures, and may be utilized herein to expedite and improve upon diagnostic and treatment steps as described above. For example, such a configuration may be utilized to create diametrically opposed lesions, to facilitate faster pattern creation, as described in reference to FIG. 22, and to assist with load-counterload relationships in delicate tissue intervention. FIG. 25B illustrates an embodiment emphasizing that the sheath instrument (23, or 24 in other depictions herein) may be advanced distally into the renal artery or other subject tissue structure lumen, to provide easy access for one or more guide instruments (24, 25) to the arterioles (196) or other distal structures, which may be advantageous for direct diagnostics and intervention pertinent to the JGA cells, for example.

In another embodiment, a stent or stentlike member configured to elute one or more drugs or compounds configured to denervate the nearby targeted neural plexus tissue may be deployed into a structure of interest, such as a renal artery or renal vein, to accomplish such denervation over a designated period of time, after which the stent or stentlike member may be removed, resorbed, or left in place as a substantially bioinert prosthesis.

Figure 26A:
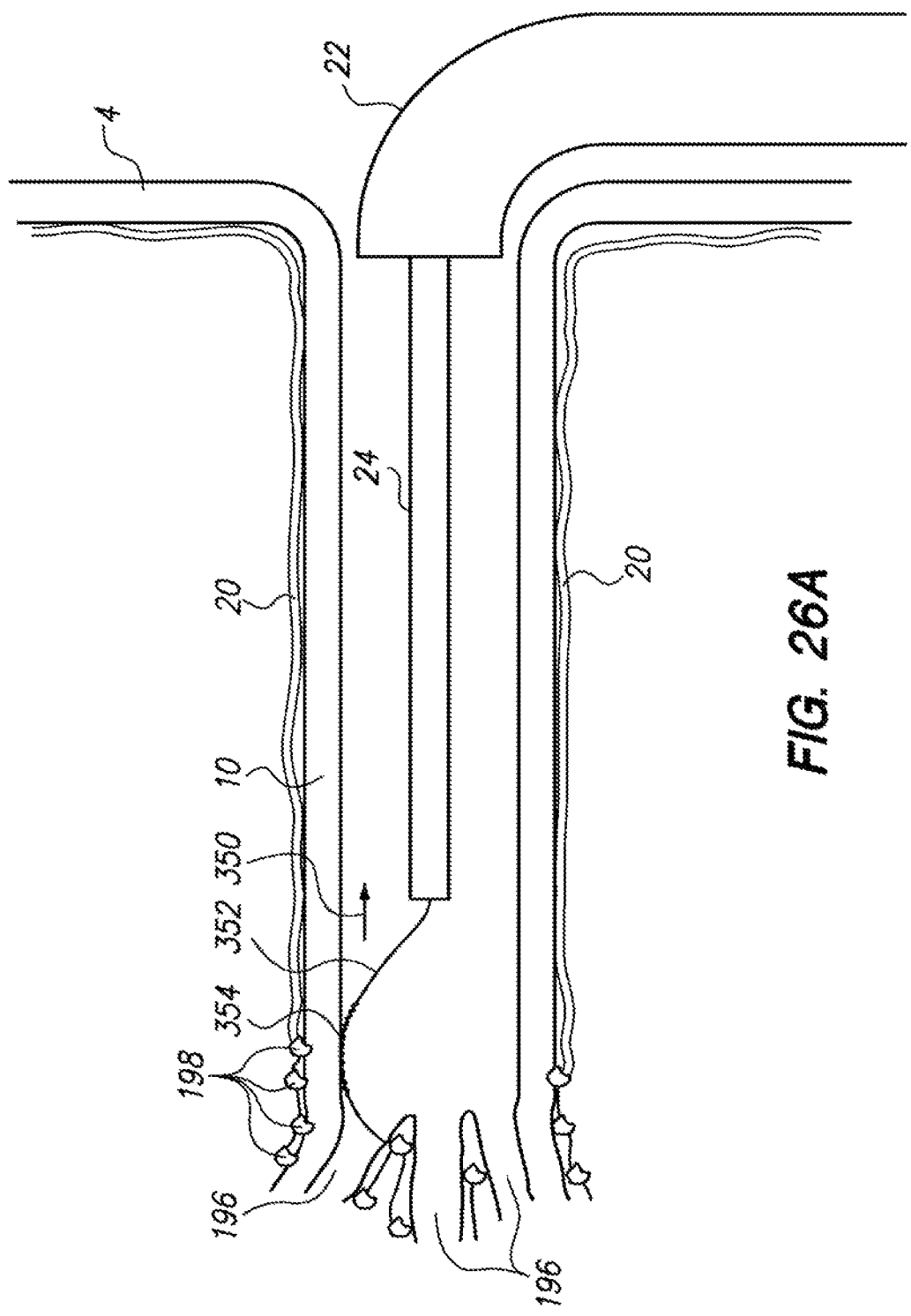
FIGS. 26A-26C illustrate an embodiment wherein a pullback technique may be utilized in a denervation treatment with a pre-shaped J-curve instrument.
Figure 26B:
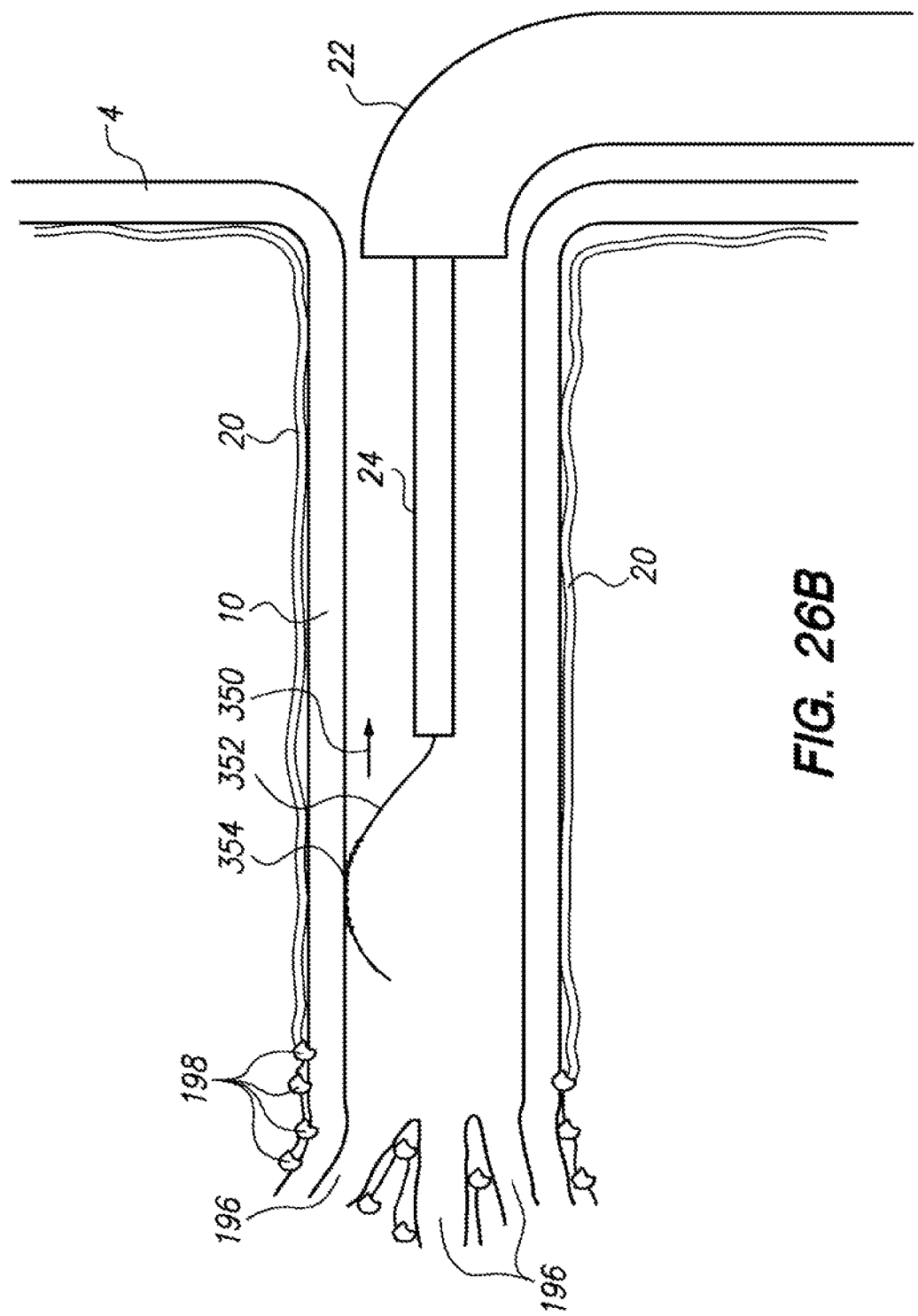
Figure 26C:
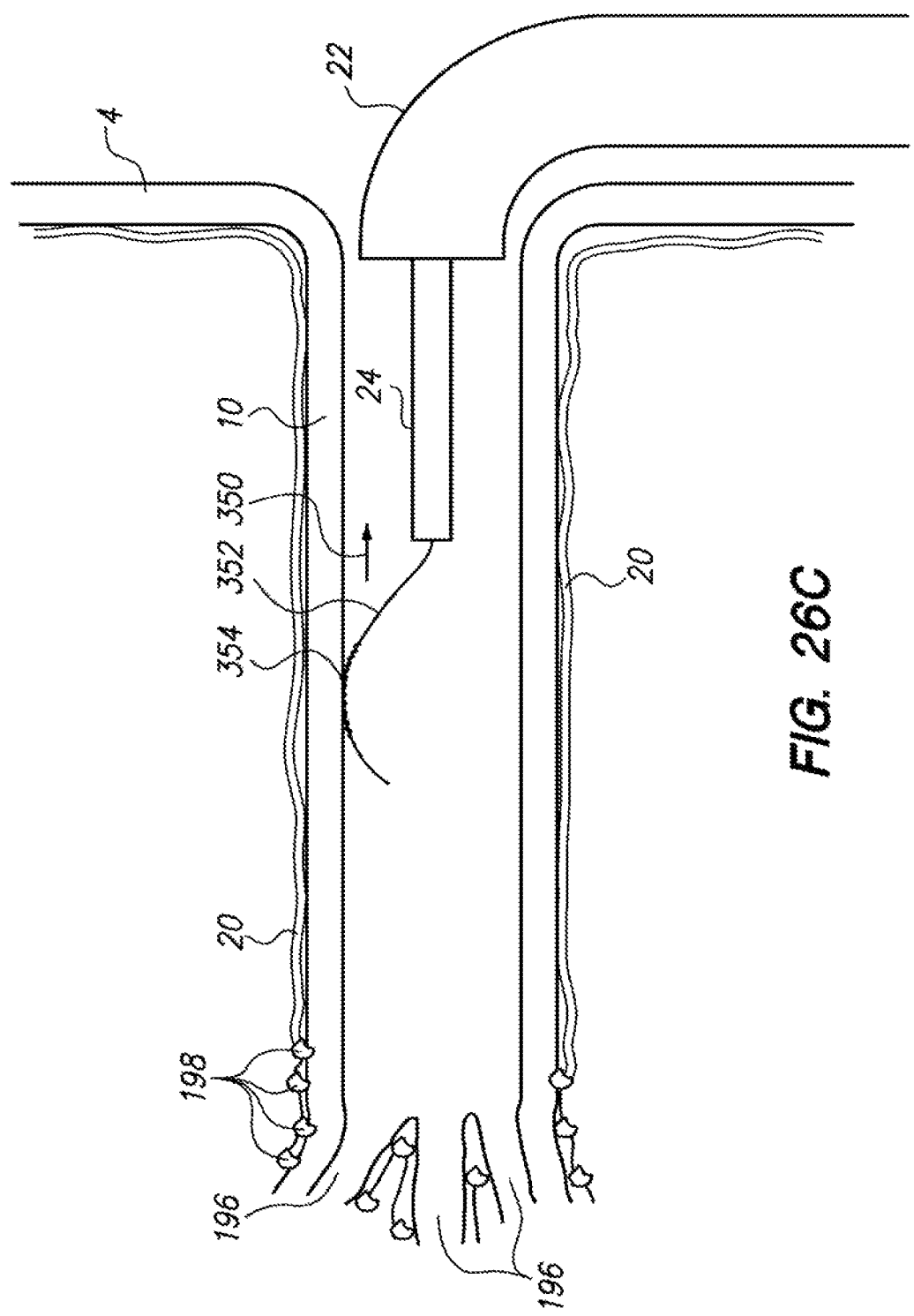

Referring to FIGS. 26A-26C, another embodiment is illustrated wherein a steerable sheath (22) and guide instrument (24) assembly may be utilized to provide direct access for a pre-shaped or pre-bent interventional instrument, such as a pre-bent J-curve instrument (352) featuring a bent electrode portion (354) configured to create a lesion in the same shape when current is flowed through the electrode portion (354) and into nearby tissue structures, such as the interior of the renal artery (10), as shown, or portions of the renal vein, nearby renal nerve strands (20), JGA cells (198), and the like. In one embodiment, in a manner similar to that described above in reference to FIGS. 23A-23C, wherein a pre-bent spiral or helical instrument (320) is pulled back through the associated vessel, the arcuate or curved interventional instrument of FIGS. 26A-26C may also be controllably pulled back to create an elongate lesion to disrupt the pre-existing electrical communication pathways of the nearby neural plexus tissue. FIGS. 26B and 26C show additional levels of progression of pullback (350). In another embodiment, the instrument (352) may be controllably rotated during pullback, or during a portion of pullback, to establish a predetermined pattern of contact between the electrode portion (354) and the surrounding tissue structures (10, 20, 198, 196). During pullback, current may be either continuously flowed through the electrode portion (354), in which case a "long linear lesion" may be produced in a solid (i.e., noninterrupted) linear, curvy, or other pattern, or the current may be discontinuously flowed through the electrode portion (354), creating a "long linear lesion" may be produced in a discontinuous (i.e., interrupted) linear, curvy, or other pattern.

Figure 27A:
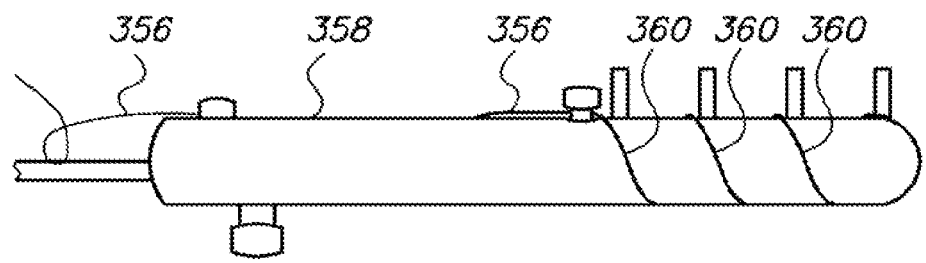
FIGS. 27A-27C illustrate various aspects of manufacturing and behavior details of a pre-shaped spiral instrument embodiment.
Figure 27B:
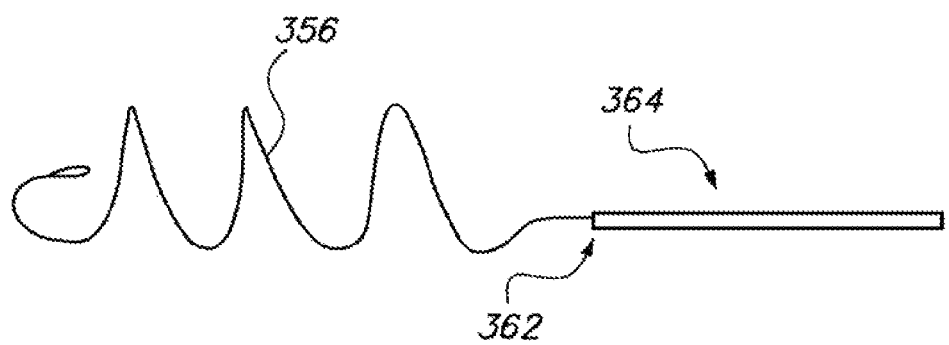
Figure 27C:
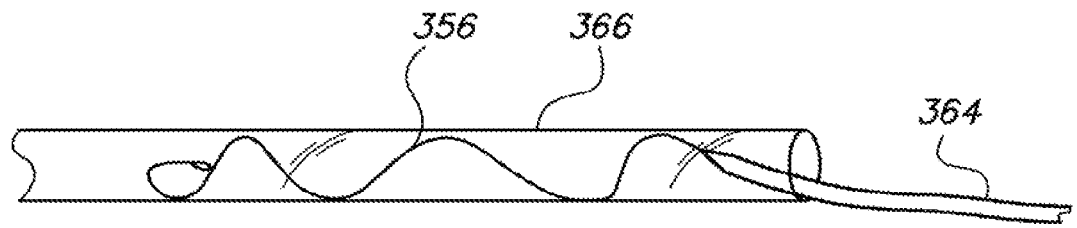

Referring to FIGS. 27A-27C, further details regarding aspects of a helical or spiral type pre-bent or pre-formed instrument treatment element (320) may be formed and configured to behave are illustrated. Referring to FIG. 27A, a series of spiral windings (360) created on a mandrel (358) may be utilized to form a helical or spiral pre-bent or pre-formed shape into a wire (356). Heat treatment may be utilized to maintain this form for the wire (356) after removal of the mandrel, as shown in FIG. 27B, wherein the spiral wire (356) is shown coupled to a piece of metal hypotube (364) via a metallic crimpling coupler (362), which provides the wire (356) with a proximal handle or deliver member for operative manipulation. Referring to FIG. 27C, depending upon what materials are utilized for the wire (356), it may be placed in a restraining tube or lumen (366) that radially constrains the outer diameter of the spiral—an in such radially-collapsed configuration, the instrument may be configured to still retain the generally spiral or helical configuration until it is released from such constraint, after which it may be configured to return to the radially expanded configuration, as in FIG. 27B.

Figure 28A:
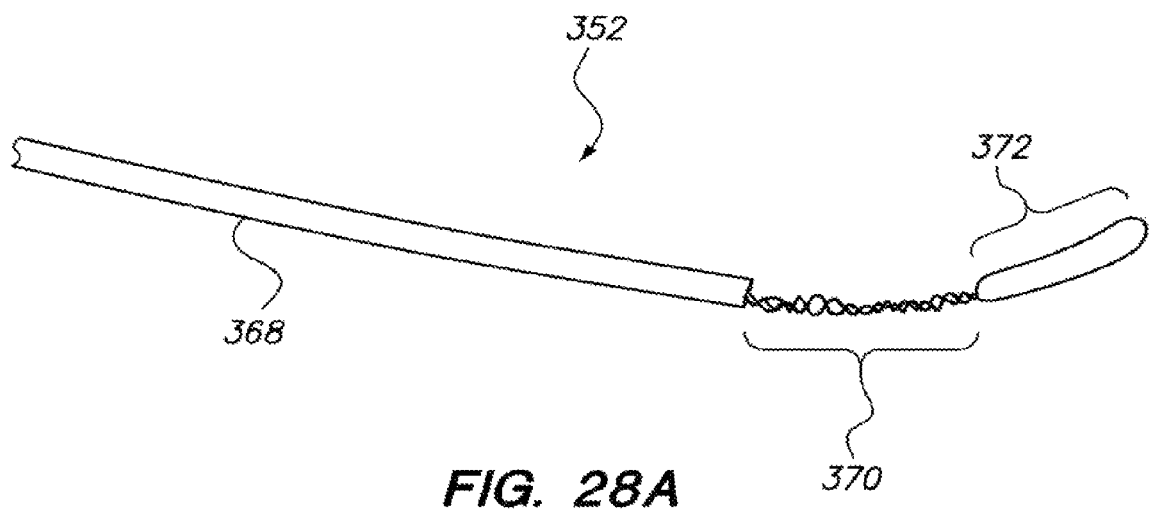
FIGS. 28A and 28B illustrate various details of a pre-shaped J-curve instrument embodiment.
Figure 28B:
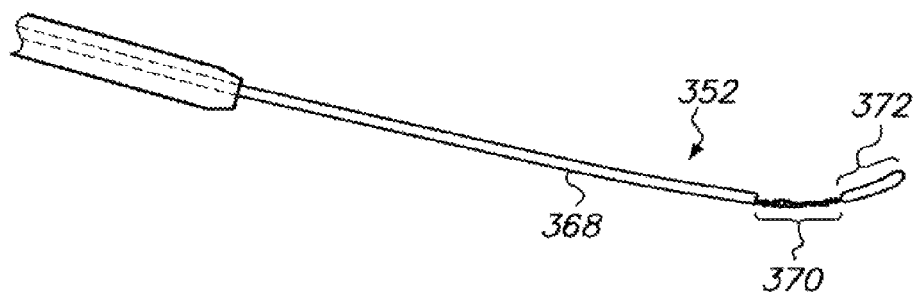

Referring to FIG. 28A, in one embodiment, a J-curve type arcuate instrument (352) may be formed by taking a J-curve-shaped insulated guidewire, such as those available from Terumo Corporation, and removing a portion of the polymeric outer insulation, for example, with a knife or other sharp instrument, to leave behind an exposed metallic core portion which may be utilized as a conductive electrode portion (370), and distal (372) and proximal (368) portions which remain insulated and generally nonconductive relative to the conductive electrode portion (370). A farther out perspective view is shown in FIG. 28B.

Referring to FIGS. 29-34, various process embodiments are illustrated wherein one or more minimally invasive instruments may be utilized in diagnostic and/or interventional medical procedures utilizing pre-shaped instruments as described above. Referring to FIG. 16, after a remotely steerable sheath catheter instrument is inserted into the aorta and navigated toward the renal artery (175), the renal artery may be cannulated, for example with a coaxially associated remotely steerable guide instrument that is movably coupled to the sheath instrument (174). An interactive imaging study, or steps thereof, may be conducted of the renal artery and associated neural anatomy using one or more minimally invasive imaging modalities, such as ultrasound, fluoroscopy, and/or OCT (176), as described above. The results of the imaging study may be utilized to create a mapping representation of the neural anatomy relative to the renal artery anatomy, for example, by stimulating one or more of the associated nerve fibers and observing resulting signal conduction (178). In other words, referring back to FIGS. 14E and 14F, in one embodiment, one or more of the proximal (i.e., closer to the aorta in the variation of FIG. 14E) circuit elements and/or associated probing portions (element 296 of FIG. 14F) may be used to stimulate or electrify adjacent nerve fiber (20) portions at such proximal position, and the conduction of such stimulation may be detected with each of the other circuit elements (294) to monitor or "map" the associated conduction pathways. The results of such mapping may be utilized in the selective denervation of portions of the renal plexus using a pre-shaped instrument such as a J-curved or spiral shaped instrument, for example, by transmitting current to heat and denervate such portions (324). The mapping configuration may then be utilized to confirm that the denervation was, indeed, successful, or to what extent, with further stimulation of the pertinent fibers and monitoring of the results. Further, renin levels, such as in the renal vein, may be monitored to determine a level of treatment success associated with the thermal denervation treatment. Similarly, alcohol and other fluids may be utilized and monitored for denervation. Ultimately, the pertinent instruments may be retracted and the vascular access closed (326).

Figure 29:
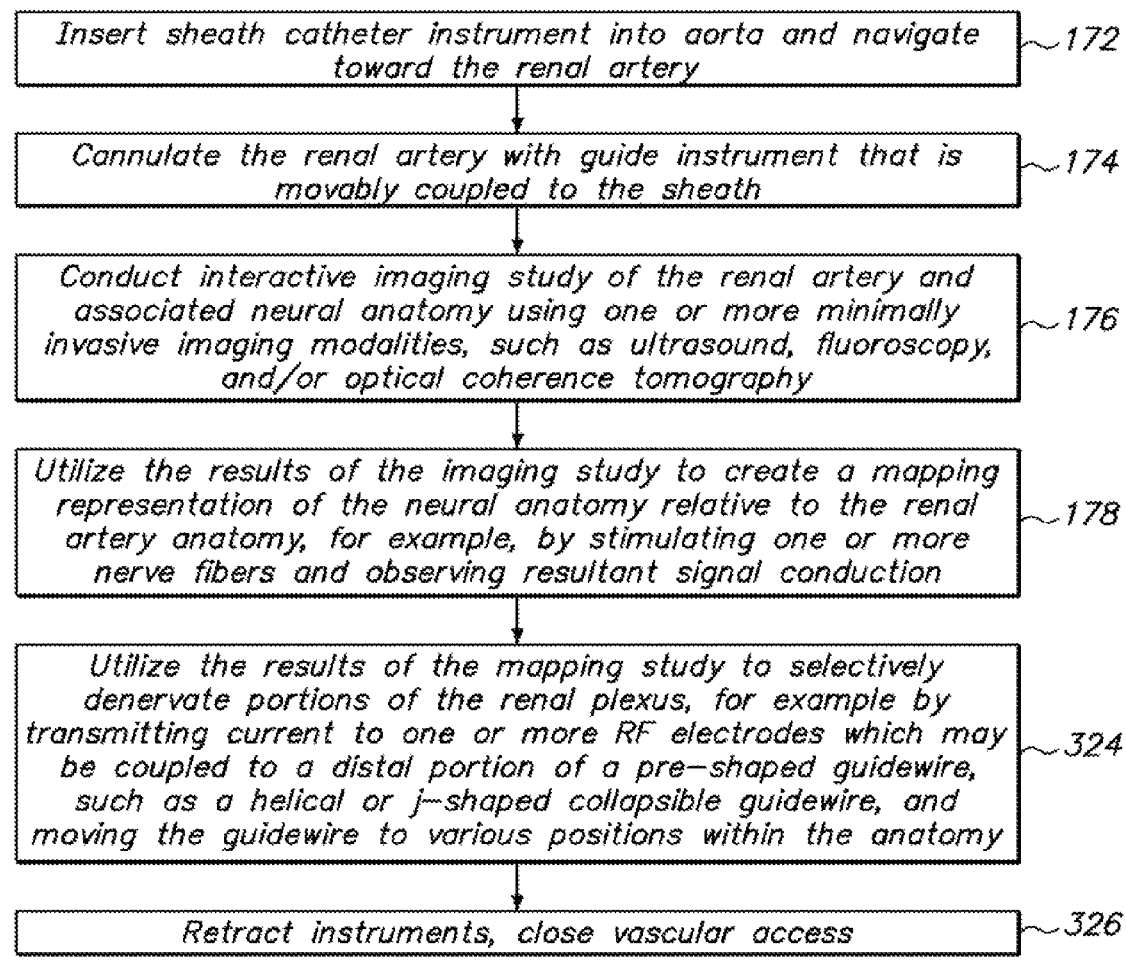
FIGS. 29-34 illustrate process embodiments in accordance with the present invention.
Figure 30:
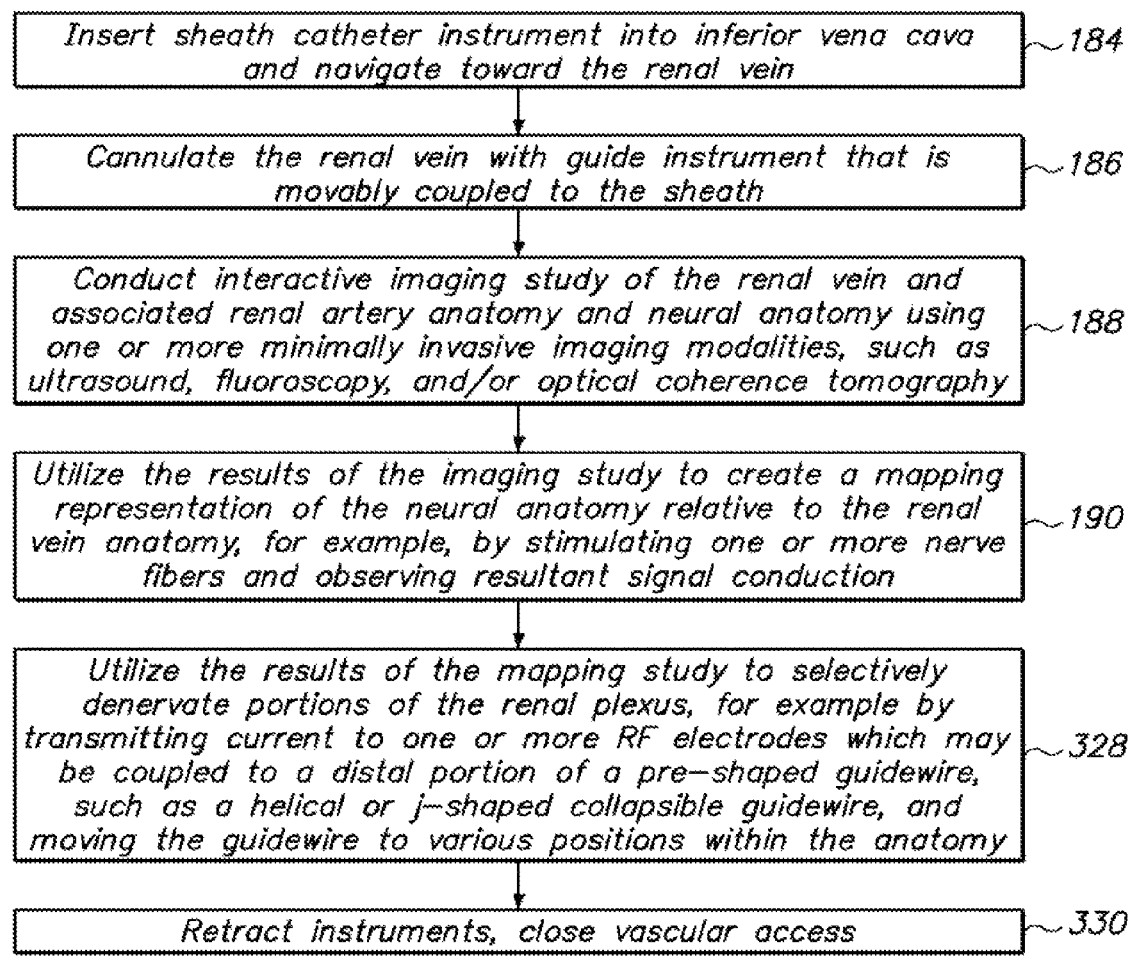

Referring to FIG. 30, a process similar to that of FIG. 29 is depicted, with the exception that a venous route is utilized to conduct denervation near the renal artery. This is believed to be less clinically complicated in certain scenarios. The catheter instrumentation is inserted into the inferior vena cava and navigated toward the renal vein (184). The renal vein is cannulated with a guide instrument movably coupled to the sheath instrument (186). The imaging study is conducted not only on the neural anatomy, but also on the renal vein anatomy and renal artery anatomy to understand the relationships of these three and other nearby tissue structures (188). The results of the imaging study may be utilized as inputs in a mapping subprocess, wherein one or more nerve fibers may be stimulated and the resulting signal conduction observed (190). The neural anatomy map resulting from the mapping efforts may be utilized for selective denervation treatment of the renal plexus using a pre-shaped instrument, such as a j-shaped or spiral-shaped guidewire containing one or more electrodes (328), as well as in generating feedback to an operator regarding the effectiveness of various denervation attempts (as described above, renin levels also may be monitored). Subsequently the instruments may be retracted and the vascular access closed (330).

Figure 31:
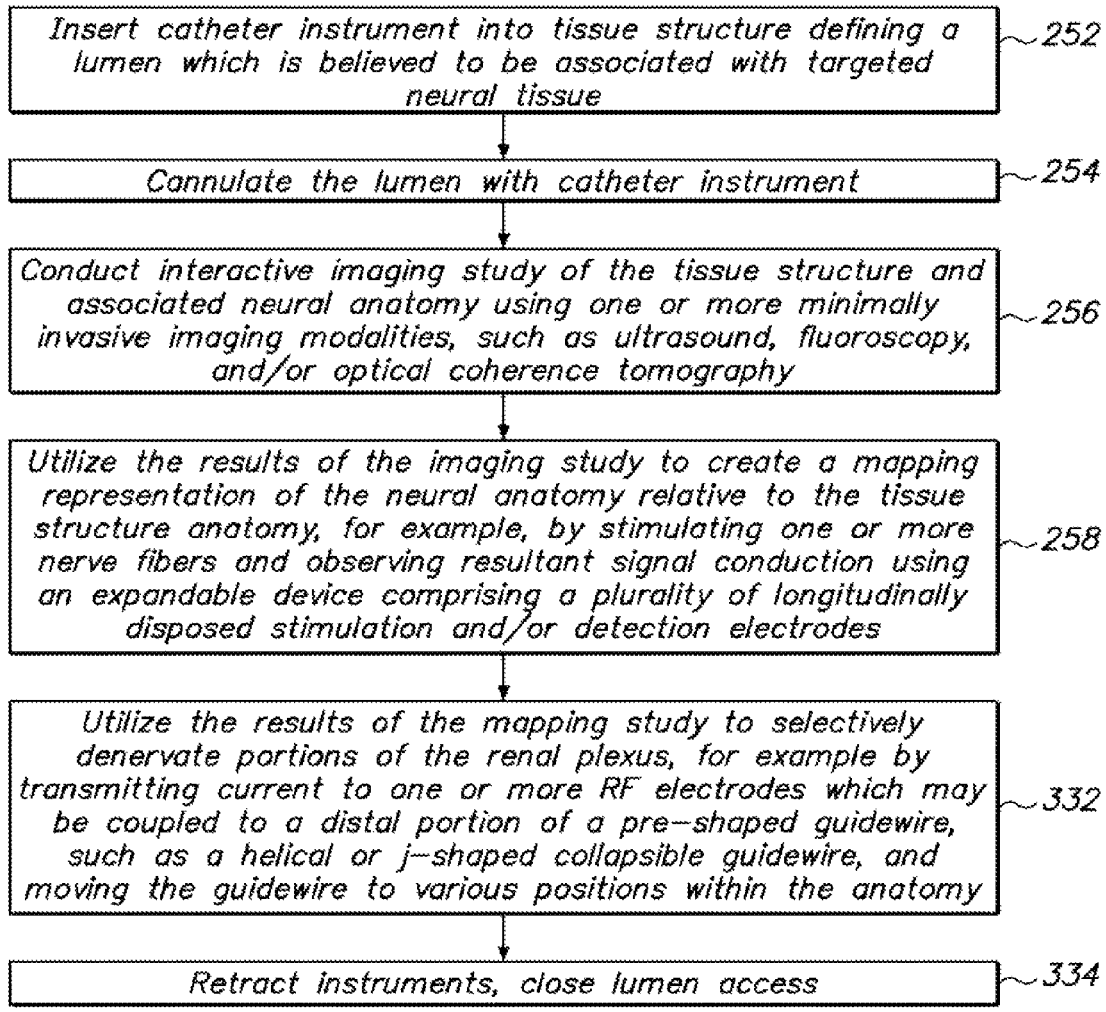

The embodiment of FIG. 31 illustrates that process configurations such as those described above in reference to FIGS. 29 and 30 may be broadly applied to many tissue structures that define one or more lumens through which the pertinent instrumentation may be advanced and utilized. Referring to FIG. 31, a catheter instrument may be inserted into the tissue structure defining a lumen believed to be associated with targeted neural tissue (252). The lumen may be cannulated with the catheter instrument (254). An interactive imaging study may be conducted to create an image-based anatomic mapping representation of the neural anatomy and other pertinent tissue structures (256), and an expandable device such as that described in reference to FIGS. 14E and 14F may be utilized to observe signal conduction (258) and create an electrical mapping which may be utilized to monitor the effectiveness of the treatment steps with the pre-shaped instrumentation (332). Subsequently the instrumentation may be removed and access to the pertinent lumens and/or tissue structures discontinued (334).

Figure 32:
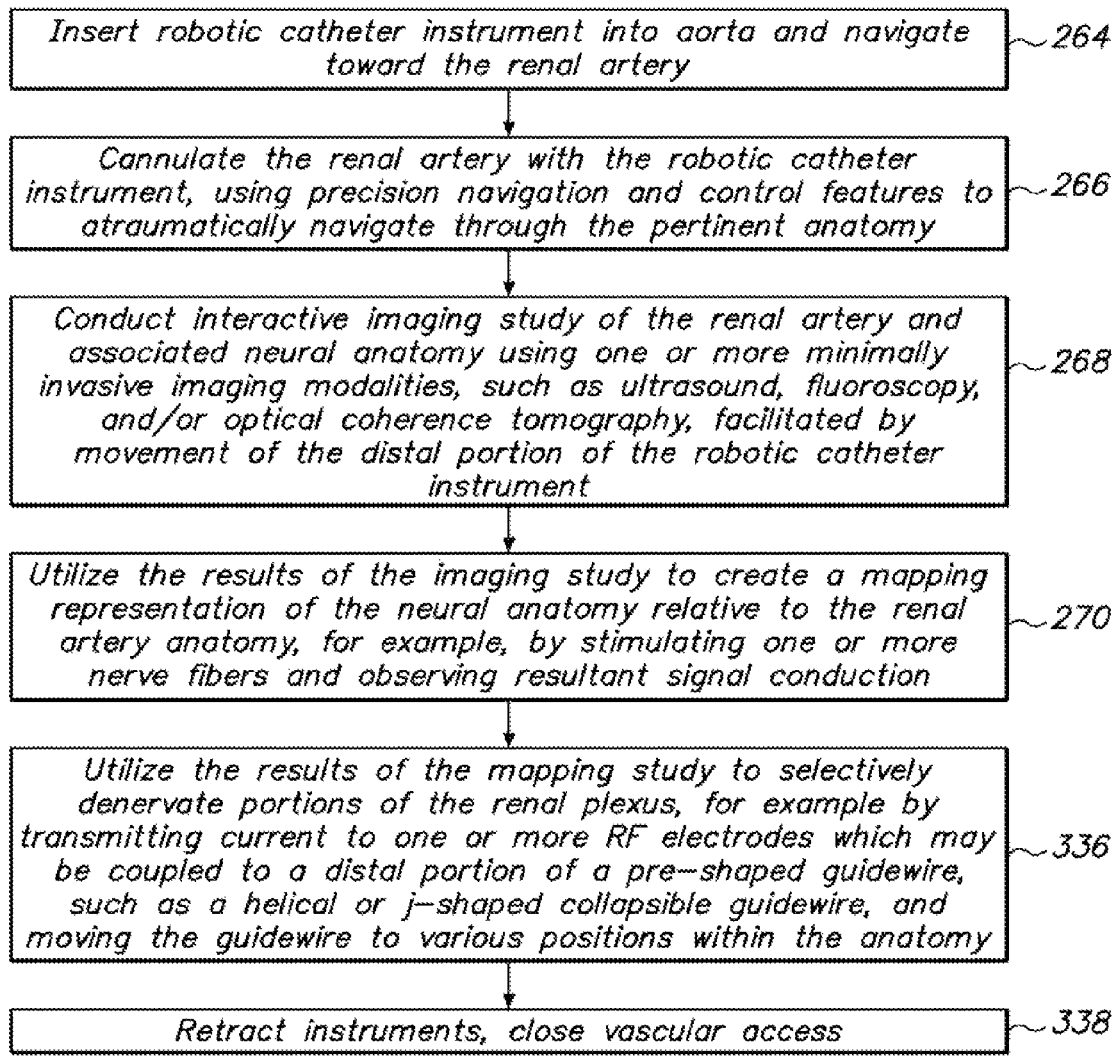
Figure 34:
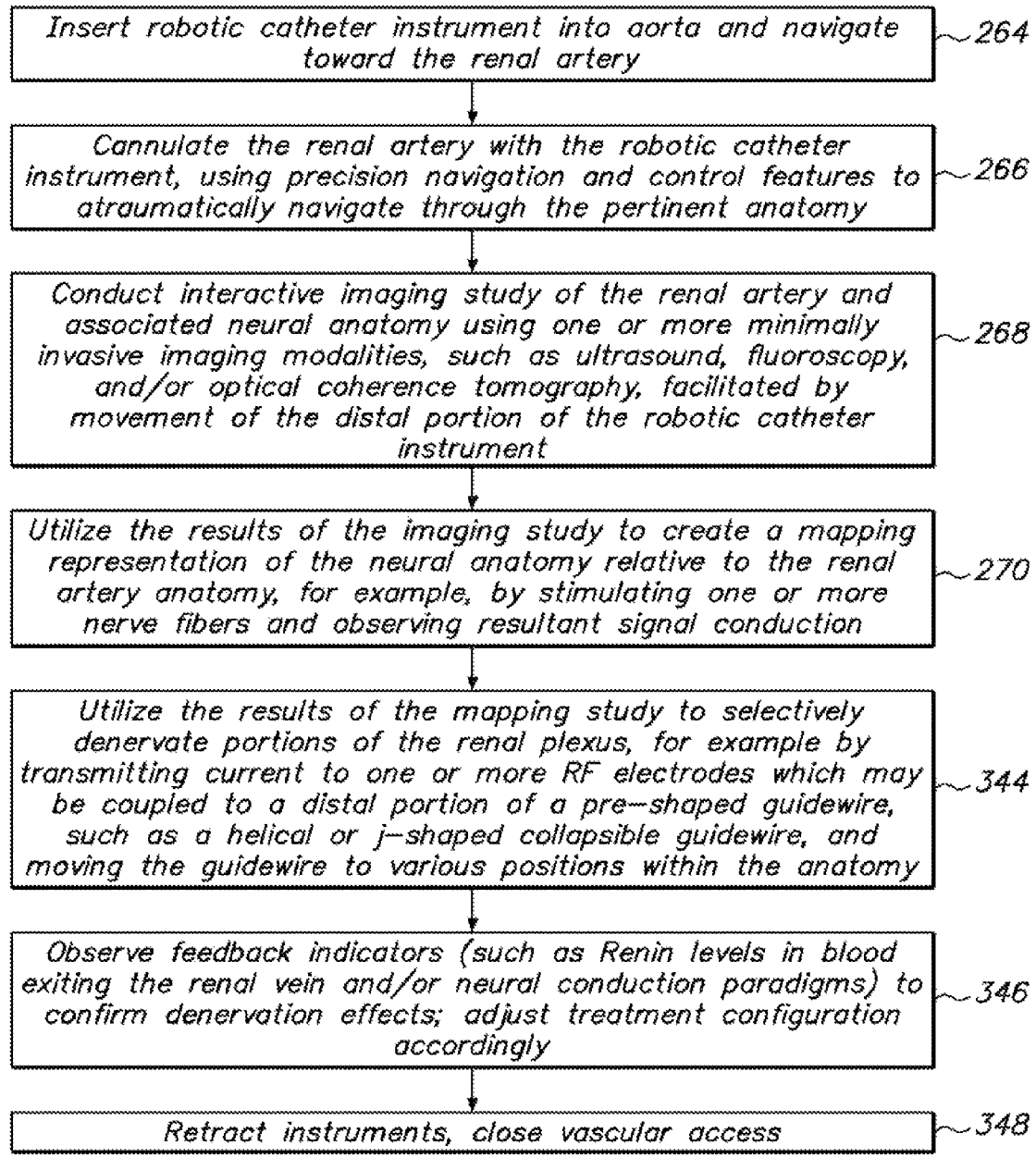

FIG. 32 illustrates aspects of an embodiment wherein a robotically-steerable catheter instrument specifically is utilized (as described above, the aforementioned catheter instruments may or may not be remotely electromechanically navigable). With the robotic catheter instrumentation inserted into the pertinent lumen, such as an aorta in this example (264), precision navigation and control features of the robotic instrument may be utilized during the insertional navigation (266), anatomic imaging may be conducted (268), electrical mapping may be conducted (270), and selective denervation may be conducted using pre-shaped instruments (336), followed by removal of the pertinent instrumentation and closure of the vascular access (338). FIG. 34 illustrates a related embodiment with the additional step depicted (346) of observing feedback indicators, such as renin levels in blood exiting the renal vein and/or neural conduction paradigms with the mapping configuration, as confirming techniques for monitoring and/or adjusting treatment in a closed loop type of configuration. Steps 344 and 348 of the embodiment of FIG. 34 are similar to steps 336 and 338 of the embodiment of FIG. 32.

Figure 33:
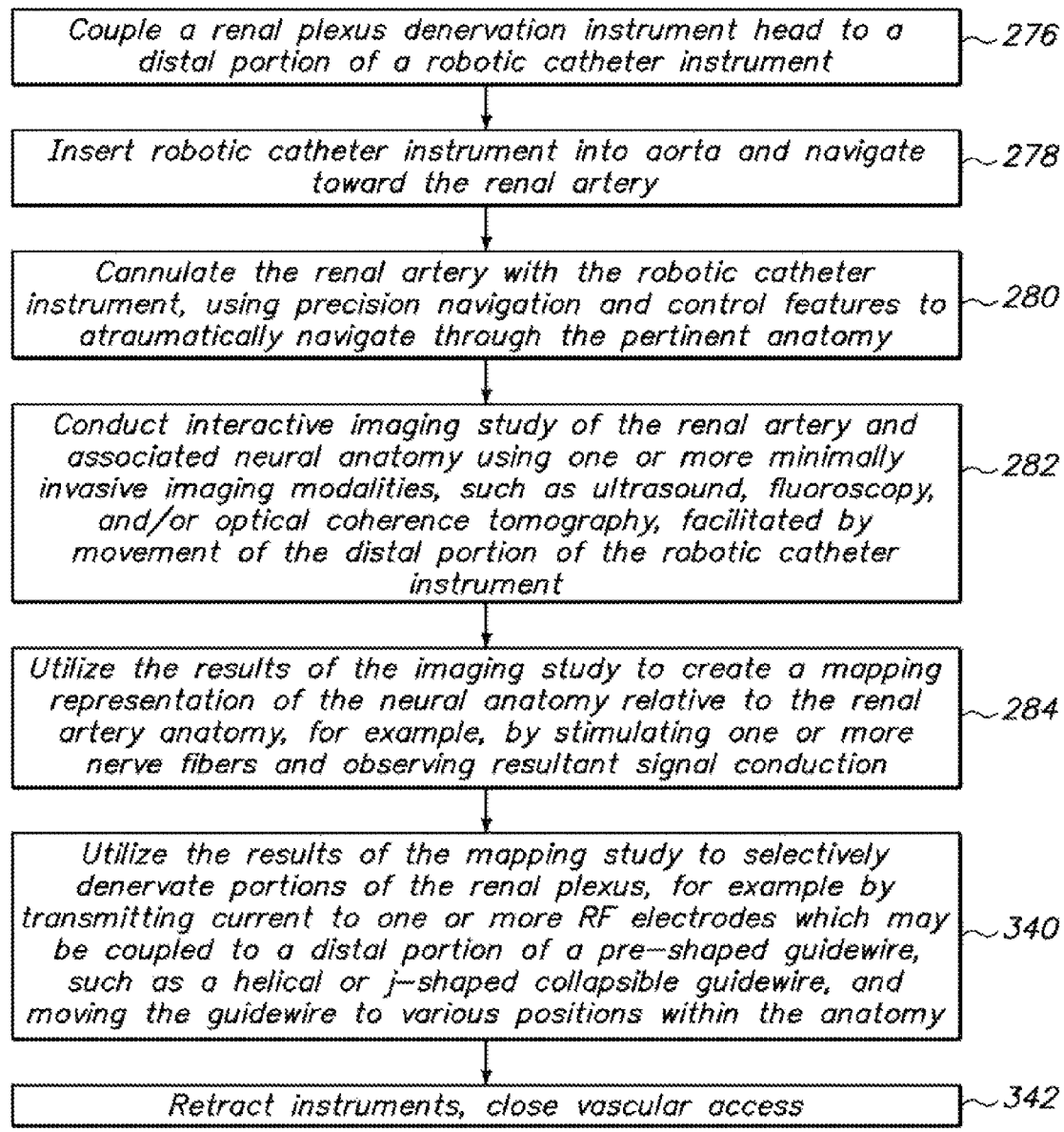

Referring to FIG. 33, a robotic catheter system such as that described and incorporated above may be utilized to operate an off-the-shelf treatment head such as those available on instruments from the Ardian division of Medtronic Corporation, to improve the navigability of such treatment head, and combine the treatment capabilities of such treatment head with additional diagnostic and treatment capabilities, such those described herein. As shown in FIG. 20, after a renal plexus denervation treatment head has been coupled to a distal portion of a robotic catheter instrument (276), the instrument may be inserted into an aorta or other lumen and navigated toward the renal artery or other targeted tissue structure (278). In the depicted renal intervention embodiment, the renal artery may be cannulated using the navigation control of the robotic instrumentation (280), after which an anatomic imaging study may be conducted (282), an electrical mapping study conducted (284), selective denervation attempted with feedback from the pre-shaped instrument mapping configuration (340), and subsequent removal of the instruments and closure of the access (342).

Any of the aforementioned deployed structures may comprise resorbable materials in addition to the aforementioned nonresorbable materials—to facilitate combinations and permutations which may be completely resorbed, leaving behind a biologically healed access wound.

Further, any of the aforementioned configurations may be applied to other tissue structure configurations involving natural lumens to be navigated, and nearby neural or other tissue structures to be targeted. For example, the techniques and configurations herein may be applied to other aspects of the cardiovascular and renal/urinary systems, as well as other anatomic subsystems including but not limited to the respiratory, upper gastric, and lower gastric subsystems.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject interventions may be provided in packaged combination for use in executing such interventions. These supply "kits" further may include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A method for ablating a nerve adjacent a renal artery, the method comprising:
   navigating a pre-shaped ablative element positioned at or near a distal end of a flexible, robotic, electromechanically steerable catheter into the renal artery in a collapsed configuration, using one or more control elements coupled to a proximal end of the steerable catheter;
   imaging targeted portions of the nerve from inside the renal artery to create an anatomic map of the targeted portions;
   using the anatomical map to create thereon an electrical map of the targeted portions relative to the renal artery, to assist in identification of selective denervation treatment locations within a renal plexus adjacent the renal artery;
   causing the pre-shaped ablative element to assume an expanded configuration within the renal artery to contact an inner wall of the renal artery in a pattern configured to address the targeted portions, based at least in part on the anatomic map and the electrical map;
   passing a current through the pre-shaped ablative element to ablate the nerve; and
   monitoring progress of ablation of the nerve, using the pre-shaped ablative element and the electrical map.

2. The method of claim 1, wherein the steerable catheter comprises a coaxially-associated catheter configured to move in response to control signals from a master input device configured to be manually operated by an operator.

3. The method of claim 1, wherein creating an electrical map comprises:
   stimulating a first portion of the nerve; and
   detecting conduction of the stimulation at a second portion of the nerve longitudinally displaced from the first portion.

4. The method of claim 3, further comprising associating a first nerve anatomical location with the first portion of the nerve and a second nerve anatomical location with the second portion of the nerve.

5. The method of claim 4, further comprising associating a renal artery anatomical location from the anatomic map with each of the nerve anatomical locations to form an electroanatomical map.

6. The method of claim 1, wherein the treatment pre-shaped ablative element comprises a radiofrequency electrode, and wherein passing the current through the ablative element comprises passing current through the electrode.

7. The method of claim 1, further comprising advancing the pre-shaped ablative element relative to the distal portion of the steerable catheter.

8. The method of claim 1, wherein creating an electrical map comprises stimulating a first portion of the nerve and detecting conduction of the stimulation in a portion of a neural plexus associated with the nerve.

9. The method of claim 1, further comprising moving the pre-shaped ablative element relative to the targeted portions while passing current through the pre-shaped ablative element to ablate an elongate portion of the nerve.

10. The method of claim 9, wherein the moving is actuated by manual or electromechanical pullback of the pre-shaped ablative element.

* * * * *